United States Patent
Watanabe et al.

(10) Patent No.: US 11,366,386 B2
(45) Date of Patent: *Jun. 21, 2022

(54) PATTERNING PROCESS

(71) Applicant: SHIN-ETSU CHEMICAL CO., LTD., Tokyo (JP)

(72) Inventors: Tsukasa Watanabe, Joetsu (JP); Tsutomu Ogihara, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 421 days.

This patent is subject to a terminal disclaimer.

(21) Appl. No.: 16/414,855

(22) Filed: May 17, 2019

(65) Prior Publication Data

US 2019/0354017 A1 Nov. 21, 2019

(30) Foreign Application Priority Data

May 21, 2018 (JP) ............................... JP2018-97445

(51) Int. Cl.
| | | |
|---|---|---|
| G03F 7/00 | (2006.01) | |
| G03F 7/20 | (2006.01) | |
| G03F 7/004 | (2006.01) | |
| G03F 7/32 | (2006.01) | |
| C07C 307/00 | (2006.01) | |
| C07C 309/10 | (2006.01) | |
| G03F 7/075 | (2006.01) | |
| G03F 7/09 | (2006.01) | |
| G03F 7/038 | (2006.01) | |

(52) U.S. Cl.
CPC .......... *G03F 7/0035* (2013.01); *C07C 307/00* (2013.01); *C07C 309/10* (2013.01); *G03F 7/0042* (2013.01); *G03F 7/0382* (2013.01); *G03F 7/0757* (2013.01); *G03F 7/094* (2013.01); *G03F 7/2004* (2013.01); *G03F 7/2022* (2013.01); *G03F 7/325* (2013.01)

(58) Field of Classification Search
None
See application file for complete search history.

(56) References Cited

U.S. PATENT DOCUMENTS

| | | | |
|---|---|---|---|
| 5,250,395 A | 10/1993 | Allen et al. | |
| 5,534,312 A | 7/1996 | Hill et al. | |
| 2005/0008864 A1 | 1/2005 | Ingen Schenau et al. | |
| 2009/0136869 A1 | 5/2009 | Ogihara et al. | |
| 2010/0086872 A1 | 4/2010 | Ogihara et al. | |
| 2012/0052685 A1* | 3/2012 | Ogihara | G03F 7/094 438/702 |
| 2013/0029270 A1 | 1/2013 | Hatakeyama | |
| 2014/0193757 A1 | 7/2014 | Ogihara et al. | |
| 2014/0273448 A1 | 9/2014 | Ogihara et al. | |
| 2015/0099228 A1 | 4/2015 | Hatakeyama et al. | |
| 2016/0231652 A1 | 8/2016 | Hatakeyama | |
| 2017/0299962 A1 | 10/2017 | Shiratani et al. | |

FOREIGN PATENT DOCUMENTS

| | | |
|---|---|---|
| EP | 2 172 808 A1 | 4/2010 |
| EP | 3 244 262 A1 | 11/2017 |
| JP | 2005-505691 A | 2/2005 |
| JP | 2009-126940 A | 6/2009 |
| JP | 5756134 B2 | 7/2015 |
| JP | 6119544 B2 | 4/2017 |
| KR | 10-2014-0113381 A | 9/2014 |
| KR | 10-2016-0098059 A | 8/2016 |
| WO | 2016/172737 A1 | 10/2016 |

OTHER PUBLICATIONS

Nov. 9, 2020 Office Action issued in Korean Patent Application No. 10-2019-0059027.
Hinsberg et al.; "Extendibility of Chemically Amplified Resists: Another Brick Wall?;" Advances in Resist Technology and Processing XX; Proceedings of SPIE; 2003; pp. 1-14; vol. 5039.
Itani et al.; "Alternative developer solutions for extreme ultraviolet resist;" J. Vac. Sci. Technol. B; 2009; pp. 2986-2989; vol. 27, No. 6.
Kishikawa et al.; "Assessment of trade-off between resist resolution and sensitivity for optimization of hyper-NA immersion lithography;" Optical Microlithography XX, Proc. of SPIE; 2007; p. 65203L-1-65203L-9; vol. 6520.
U.S. Appl. No. 16/414,826, filed May 17, 2019 in the name of Watanabe et al.
Oct. 22, 2019 extended Search Report issued in European Patent Application No. 19175549.5.
Oct. 23, 2019 extended Search Report issued in European Patent Application No. 19175551.1.
Jul. 7, 2021 Office Action issued in U.S. Appl. No. 16/414,826.
Oct. 4, 2021 Notice of Allowance Issued in U.S. Appl. No. 16/414,826.

* cited by examiner

*Primary Examiner* — Kathleen Duda
(74) *Attorney, Agent, or Firm* — Oliff PLC

(57) ABSTRACT

A patterning process, including: forming the first resist film from first resist material containing an acid generator and thermosetting compound having a hydroxy group and/or carboxy group protected by an acid-labile group; forming the second resist film on first resist film from a second resist material containing a metal compound (A) and a sensitizer; irradiating the first and second resist film with a high energy beam or an electron beam to perform pattern exposure to deprotect the hydroxy group and/or carboxy group in a pattern exposed portion of first resist film and to form a crosslinked portion of the component (A) with the deprotected hydroxy and/or carboxy group on the pattern exposed portion; and developing the second resist film with a developer to give a metal film pattern composed of the crosslinked portion. This provides a method for forming a thin film resist pattern with higher resolution and higher sensitivity.

22 Claims, 1 Drawing Sheet

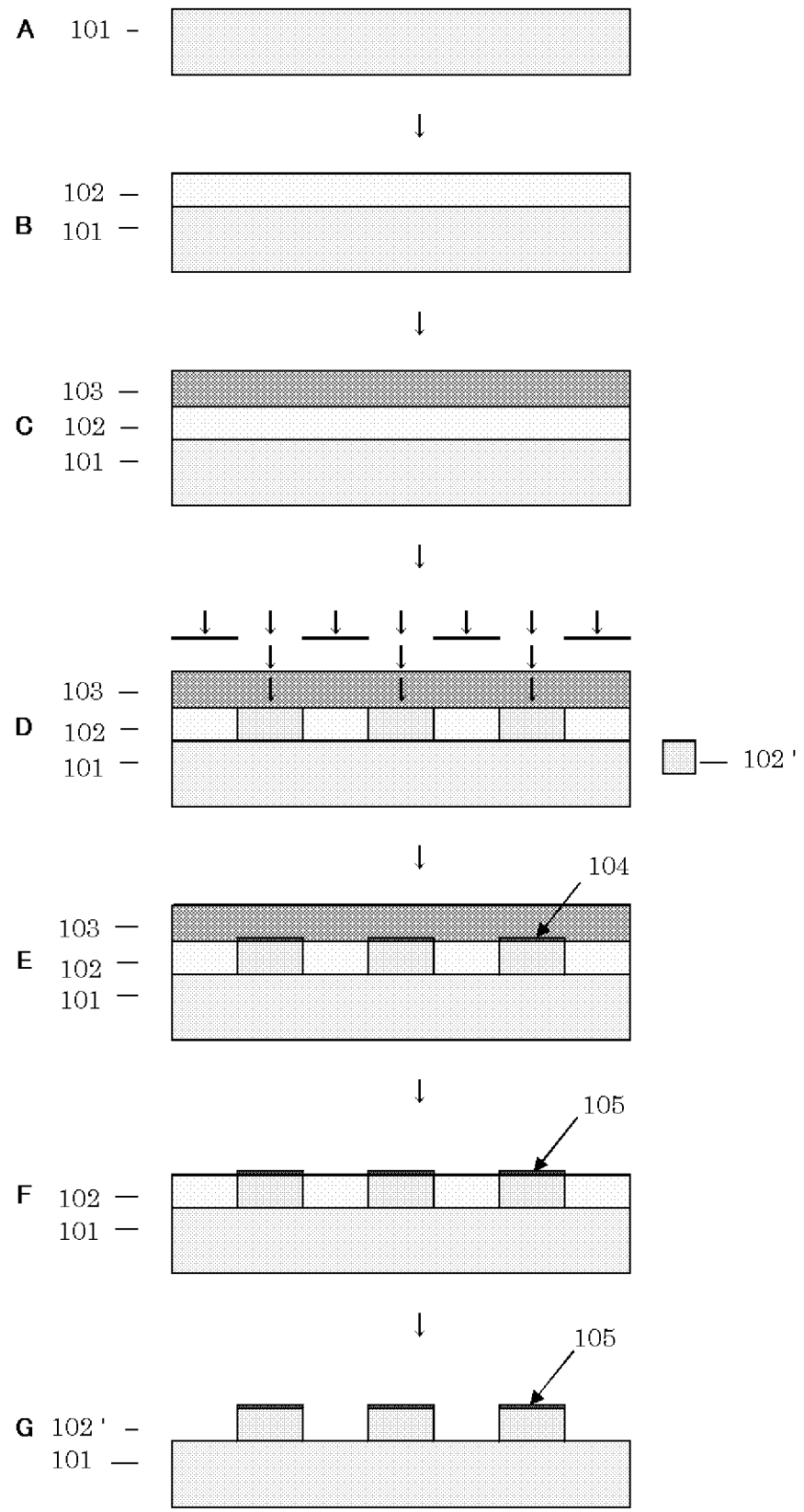

PATTERNING PROCESS

TECHNICAL FIELD

The present invention provides a method for forming a resist pattern that has thin film processability and etching resistance useful for microprocessing of a resist pattern.

BACKGROUND ART

As Large-Scale Integrated circuits (LSIs) advance toward higher integration and higher processing speed, miniaturization of a pattern rule has been required. In such a trend, in ordinary lithography using a photo-exposure, various technologies have been developed on how to process finer pattern more precisely with the light source used.

As the advanced miniaturization, image blurs due to acid diffusion have been regarded as a subject (Non-Patent Document 1). In order to ensure resolution for fine patterns with a post-45 nm size, the importance of controlling the acid diffusion is proposed not only enhancing dissolution contrast, which has been proposed previously (Non-Patent Document 2). In chemically amplified resist materials, however, the sensitivity and the contrast are enhanced by acid diffusion. Accordingly, an attempt to minimize acid diffusion by decreasing the temperature and time of post-exposure bake (PEB) lowers the sensitivity and contrast markedly.

It is effective to control the acid diffusion by adding an acid generator that generates a bulky acid. Accordingly, it has been proposed to copolymerize a polymer with an acid generator in the form of an onium salt having polymerizable olefin. In post-16 nm size patterning of resist films, however, it is considered that patterning is impossible for chemically amplified resist films in view of the acid diffusion. Accordingly, development of non-chemically amplified resist material has been required.

As a non-chemically amplified resist material, polymethyl methacrylate (PMMA) may be exemplified. The PMMA is a positive resist material which increases solubility in organic solvent developer through scission of the main chain by EUV irradiation to lower the molecular weight. Due to the lack of cyclic structure, however, it has the drawbacks of lower etching resistance.

Hydrogensilsesquioxane (HSQ) is a negative resist material which turns insoluble in alkaline developer through crosslinking by condensation reaction of silanol generated by EUV irradiation. Calixarene substituted with chlorine also functions as a negative resist material. These negative resist materials have a small molecular size prior to crosslinking and are free from causing blurs due to acid diffusion to exhibit smaller edge roughness and very high resolution. Accordingly, they have been used as a pattern transfer material to show the resolution limit of the exposure apparatus. These materials, however, are insufficient in sensitivity, and further improvement is required.

In miniaturization using EUV lithography, the resist is required to have higher sensitivity and higher resolution in the first place. In addition to that, it is also important to control line edge roughness (LER) that lowers dimensional precision. Another important subject is prevention of pattern collapse due to miniaturization. One of the reason for the pattern collapse is an increase of aspect ratio of a resist pattern. Accordingly, the resist material is required to be thinned, but this causes a sore subject to increase a burden in the subsequent etching process.

In photoresist materials for semiconductor lithography, it has been impossible as yet to use a resist material incorporated with metal because the metal atom can transfer to a substrate to cause malfunction of a semiconductor. In a use other than the semiconductor, such as a resist material for LCD (Non-Patent Document 3), however, zinc neodecanate has been used as a patterning material for forming a transparent electrode ZnO. Patent Document 1 exemplifies patterning with an acetylacetonato complex of silicon, titanium, zirconium, tantalum, barium, strontium, or hafnium. Additionally, Patent Document 2 exemplifies patterning using a copper, chromium, cerium, yttrium, barium, or aluminum salt of a ligand having a carboxy group or a ligand having an amino group. After the patterning, heat treatment is performed at 300° C. to form a pattern of metal oxide.

Patent Document 3 exemplifies a patterning using a positive resist material in which diol or triol coordinates to partly condensed alkoxide of titanium, zirconium, or hafnium. These materials make it possible to form a pattern with higher resolution and smaller edge roughness, but are insufficient in sensitivity and are required to be further improved.

Patent Document 4 shows a patterning process of forming a metal oxide-containing film onto a substrate to be processed using a composition for forming metal oxide, forming a resist upper layer film onto the metal oxide-containing film using a resist upper layer film material, followed by forming a resist pattern by exposing the resist upper layer film, transferring the resist pattern to the metal oxide-containing film, and etching the under layer of the substrate to be processed using the metal oxide-containing film having the transferred pattern as an etching mask. These patterning processes are excellent in etching selectivity and make it possible to form a pattern formed of the resist upper layer film onto a substrate to be processed without causing difference in size change, but have large number of steps for patterning and are insufficient in resolution of the resist upper layer, and further improvement is required thereby.

CITATION LIST

Patent Literature

Patent Document 1: Japanese Unexamined Patent Application Publication No. 2005-505691
Patent Document 2: U.S. Pat. No. 5,534,312
Patent Document 3: Japanese Patent No. 6119544
Patent Document 4: Japanese Patent No. 5756134

Non-Patent Literature

Non Patent Document 1: SPIE, Vol. 5039, p1 (2003)
Non Patent Document 2: SPIE, Vol. 6520, p65203L-1 (2007)
Non Patent Document 3: J. Vac. Sci. Technol., B27 (6), November/December, p2986-2989 (2009)

SUMMARY OF INVENTION

Technical Problem

In fine processing using EUV exposure, pattern collapse has been a subject due to increases in resolution, sensitivity, and aspect ratio of a pattern. In particular, one of the method to prevent the pattern collapse is thinning, which is difficult to achieve because of the insufficient etching resistance in the previous chemically amplified resists.

The present invention was accomplished in view of the above circumstances. It is an object of the present invention to provide a method for forming a thin film resist pattern with higher sensitivity while having higher resolution.

Solution To Problem

To solve the foregoing subjects, the present invention provides a patterning process to form a metal film pattern on a coated film having an exposure pattern formed thereon, comprising the steps of:

(1) coating a substrate to be processed with a first resist material containing an acid generator and a thermosetting compound having a hydroxy group and/or a carboxy group each protected by an acid-labile group, followed by baking treatment to form a first resist film being insoluble to an organic solvent;

(2) coating the first resist film with a second resist material containing a sensitizer and a component (A) of at least one element selected from the group consisting of a metal compound as well as a hydrolysate, a condensate, and a hydrolysis condensate of the metal compound, followed by baking treatment to form a second resist film;

(3) irradiating the first resist film and the second resist film with a high energy beam from a light source of an extreme ultraviolet ray with a wavelength of 3 to 15 nm or an electron beam to perform pattern exposure to deprotect the hydroxy group and/or the carboxy group in a pattern exposed portion of the first resist film and to form a crosslinked portion in which the component (A) and the deprotected hydroxy group and/or the deprotected carboxy group are crosslinked on the pattern exposed portion; and (4) developing the second resist film with a developer to give a metal film pattern composed of the crosslinked portion.

The patterning process like this makes it possible to form a thin film resist pattern with higher sensitivity while having higher resolution.

It is preferable that the baking treatment in the step (1) and/or the step (2) be performed at a temperature of 50° C. or more.

In such a temperature of baking treatment, the first resist film and the second resist film can be formed more efficiently.

It is preferable that the component (A) be at least one element selected from the group consisting of a metal compound shown by the following general formula (A-1) as well as a hydrolysate, a condensate, and a hydrolysis condensate of the metal compound, and/or at least one element selected from the group consisting of a condensate and a hydrolysis condensate of a metal compound shown by the following general formula (A-2) and the metal compound shown by the general formula (A-1):

$$M(OR^{1A})_4 \quad (A-1)$$

wherein M represents Ti, Zr, or Hf; and $R^{1A}$ represents a monovalent organic group having 1 to 20 carbon atoms and 0 or 1 hydroxy group;

$$M'X \quad (A-2)$$

wherein M' represents Ti, Zr, or Hf; and X represents a divalent or trivalent alcohol shown by the following general formula (A-3):

$$R^{2A}(OH)_m \quad (A-3)$$

wherein $R^{2A}$ represents an m-valent organic group having 2 to 20 carbon atoms and 0 or 1 hydroxy group; and "m" is an integer of 2 or 3.

Using the component (A) like this for a resist material, it is possible to form a fine pattern in a good shape.

It is preferable that the sensitizer be one or more elements selected from sensitizers shown by the following general formula (B-1):

$$M'^{n+}(Y^-)_n \quad (B-1)$$

wherein $M'^{n+}$ represents an ion of a metal selected from Mg, Ca, Ce, Zn, Cu, In, Fe, Yb, Y, Tm, Sn, Ni, Sc, Hf, Nb, Ti, Zr, Ba, Ho, Tb, Lu, La, Ag, Eu, Dy, Gd, Rb, Sr, and Cs; $Y^-$ represents an alkylsulfonate ion, an arylsulfonate ion, an alkylsulfonimidate ion, or an alkylsulfonmethidate ion each having at least one fluorine atom; and "n" is an integer satisfying $1 \leq n \leq 4$.

The sensitizer like this allows the second resist material to improve the sensitivity.

In this case, it is preferable that $Y^-$ in the general formula (B-1) be shown by any of the following general formulae (B-1-1) to (B-1-3):

$$R^{1B}-SO_3^- \quad (B-1-1)$$

$$R^{2B}-SO_2-N^--SO_2-R^{3B} \quad (B-1-2)$$

$$R^{4B}-SO_2-C^--SO_2-R^{5B} \quad (B-1-3)$$
$$\phantom{R^{4B}-SO_2-}\overset{|}{SO_2}$$
$$\phantom{R^{4B}-SO_2-}\overset{|}{R^{6B}}$$

wherein $R^{1B}$ represents a linear, branched, or cyclic alkyl group, alkenyl group, or alkynyl group having 5 to 30 carbon atoms, or an aryl group or aralkyl group having 6 to 30 carbon atoms, each having at least one fluorine atom and optionally having a halogen atom, an ether group, a thiol group, an ester group, a carbonate group, a carbonyl group, an amide group, an amino group, an azide group, a carbamate group, a nitro group, a cyano group, a hydroxy group, a carboxy group, a sulfo group, a sulfonate ester group, a sultone group, a lactone ring, or a lactam ring; $R^{2B}$, $R^{3B}$, $R^{4B}$, $R^{5B}$, and $R^{6B}$ each represent a fluorine atom, a trifluoromethyl group, a pentafluoroethyl group, a trifluoroethyl group, an octafluorobutyl group, or a nonafluorobutyl group, and $R^{2B}$ and $R^{3B}$ are optionally bonded with each other to form a ring.

The sensitizer like this allows the second resist material to further improve the sensitivity.

It is also preferable that the developer in the step (4) be an organic solvent.

Using such a developer, the second resist film can be developed more efficiently.

In this case, it is preferable that the organic solvent be one or more solvents selected from 2-octanone, 2-nonanone, 2-heptanone, 3-heptanone, 4-heptanone, 2-hexanone, 3-hexanone, diisobutyl ketone, methyl cyclohexanone, acetophenone, methylacetophenone, propyl acetate, butyl acetate, isobutyl acetate, amyl acetate, butenyl acetate, isoamyl acetate, propyl formate, butyl formate, isobutyl formate, amyl formate, isoamyl formate, methyl valerate, methyl pentenoate, methyl crotonate, ethyl crotonate, methyl lactate, ethyl lactate, propyl lactate, butyl lactate, isobuthyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

Using such a developer, the second resist film can be developed further efficiently.

Advantageous Effects of Invention

The inventive patterning process provides a fine pattern in a good shape with higher sensitivity and higher resolution, together with excellent thin film processability. In particular, a resist film containing a thermosetting compound having a hydroxy group and/or a carboxy group undergoes crosslinking reaction with a metal resist to form a pattern having both of thin film processability and etching resistance, which have been difficult to achieve by previous methods. The resist material used for patterning is excellent in storage stability such that the properties are unchanged even in a period when it is connected to a production apparatus, thereby being a negative resist material that is suitable as a material for producing a very LSI, a material for fine patterning of a photomask, and a material for patterning of EUV exposure.

BRIEF DESCRIPTION OF DRAWINGS

FIG. 1 is a flowchart showing an embodiment of a patterning process of the present invention.

DESCRIPTION OF EMBODIMENTS

As described above, it has been demanded to develop a method for forming a thin film resist pattern with higher sensitivity while having higher resolution.

The present inventors have diligently investigated to solve the above subjects to find that it is possible to form a good pattern with excellent etching resistance and thin film processability, together with excellent dissolution contrast in organic solvent development, by the patterning process of forming a film of a thermosetting compound on a substrate to be processed, additionally applying a metal compound having a particular structure thereonto, followed by EUV exposure or EB illumination to generate a hydroxy group and/or a carboxy group in the thermosetting compound film, and then causing crosslinking reaction of the generated acidic functional group with the metal compound.

That is, the present invention is a patterning process to form a metal film pattern on a coated film having an exposure pattern formed thereon, comprising the steps of:

(1) coating a substrate to be processed with a first resist material containing an acid generator and a thermosetting compound having a hydroxy group and/or a carboxy group each protected by an acid-labile group, followed by baking treatment to form a first resist film being insoluble to an organic solvent;

(2) coating the first resist film with a second resist material containing a sensitizer and a component (A) of at least one element selected from the group consisting of a metal compound as well as a hydrolysate, a condensate, and a hydrolysis condensate of the metal compound, followed by baking treatment to form a second resist film;

(3) irradiating the first resist film and the second resist film with a high energy beam from a light source of an extreme ultraviolet ray with a wavelength of 3 to 15 nm or an electron beam to perform pattern exposure to deprotect the hydroxy group and/or the carboxy group in a pattern exposed portion of the first resist film and to form a crosslinked portion in which the component (A) and the deprotected hydroxy group and/or the deprotected carboxy group are crosslinked on the pattern exposed portion; and (4) developing the second resist film with a developer to give a metal film pattern composed of the crosslinked portion.

Hereinafter, the present invention will be described specifically, but the present invention is not limited thereto.

[Patterning Process]

The inventive patterning process will be described more specifically using FIG. 1. First, the first resist material is applied onto the substrate to be processed 101, and subjected to baking treatment to form the first resist film 102, which is insoluble in an organic solvent (A, B). Then, the second resist material is applied onto the first resist film 102, subjected to baking treatment to form the second resist film 103 (C). Subsequently, the first resist film 102 and the second resist film 103 are irradiated with a high energy beam or an electron beam (pattern exposure) to form the pattern exposed portion 102' in the first resist film 102 (D). In the pattern exposed portion 102', a deprotected hydroxy group and/or carboxy group is formed. Whereat, the component (A) in the second resist film 103 undergoes crosslinking reaction with the deprotected hydroxy group and/or the deprotected carboxy group in the pattern exposed portion 102' to form the crosslinked portion 104 on (the surface of) the pattern exposed portion 102' (E). Then, the second resist film 103 is removed by organic solvent development, for example, and the protective groups eliminated through the deprotection reaction are removed optionally by heating in accordance with needs, making the crosslinked portion 104 left alone to be the metal film pattern 105 (F). Subsequently, the first resist film 102 is removed by etching, and a desired pattern can be formed (G).

Hereinafter, the first resist material and the second resist material used for the inventive patterning process will be described in more detail.

[First Resist Material]

The first resist material contains a thermosetting compound having a hydroxy group and/or a carboxy group each protected by an acid-labile group, together with an acid generator.

<Thermosetting Compound>

The thermosetting compound contains a unit having a hydroxy group and/or a carboxy group each protected by an acid-labile group (a unit protected by an acid-labile group, the protective group of which is eliminated by an action of acid generated by exposure to form a hydroxy group and/or a carboxy group, which are acidic functional groups). Illustrative examples of the most preferable unit include the repeating unit shown by the following general formula (1) or (2).

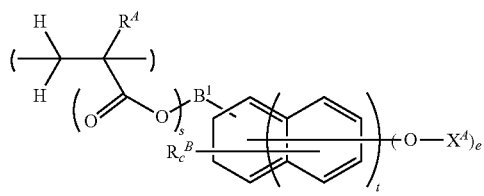

(2)

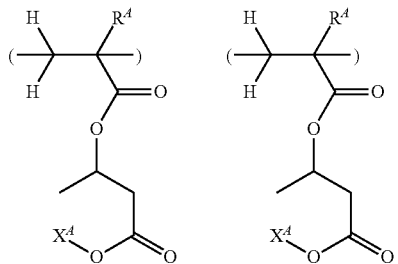

In the formulae, $R^A$ represents a hydrogen atom, a fluorine atom, a methyl group, or a trifluoromethyl group; $Z^A$ represents a single bond, a phenylene group, a naphthylene group, or —C(=O)—O—Z'—; Z' represents a linear, branched, or cyclic alkylene group having 1 to 10 carbon atoms, a phenylene group, or a naphthylene group, each may have a hydroxy group, an ether bond, an ester bond, or a lactone ring; "s" is 0 or 1; "t" is an integer of 0 to 2; each $R^B$ independently represents a hydrogen atom or an alkyl group having 1 to 6 carbon atoms; $B^1$ represents a single bond or an alkylene group having 1 to 10 carbon atoms optionally having an ether bond; "c" is an integer satisfying c≤5+2t−e; "e" is an integer of 1 to 3; $X^A$ represents an acid labile group when "e" is 1 and represents a hydrogen atom or an acid labile group when "e" is 2 or more, provided that one or more of them represents an acid labile group.

In the unit shown by the general formula (1) or (2), at least one of hydroxy group and carboxy group is/are protected by an acid-labile group. The acid-labile group may be, basically, any group that is eliminated by acid to provide an acidic functional group, as previously used in many known chemically amplified resist compositions, and is preferably an alkyl group. As the unit shown by the general formula (1), the ones shown by the following formulae (A-10) are preferable, and as the unit shown by the general formula (2), the ones shown by the following formulae (B-10) are preferable.

(A-10)

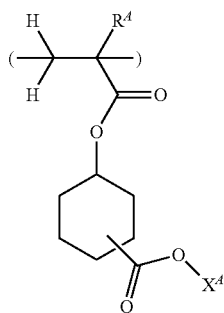
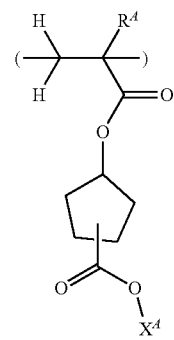

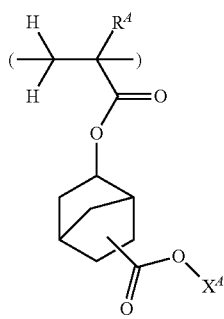
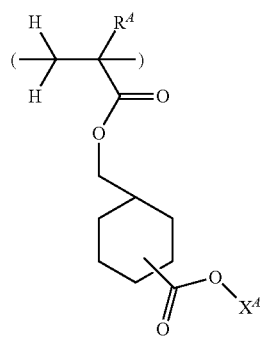

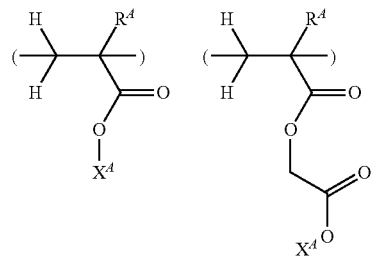

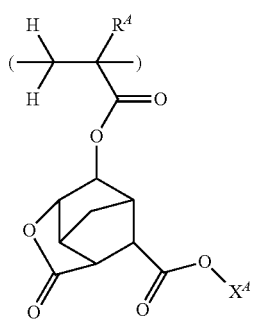
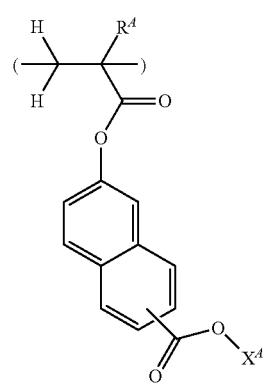

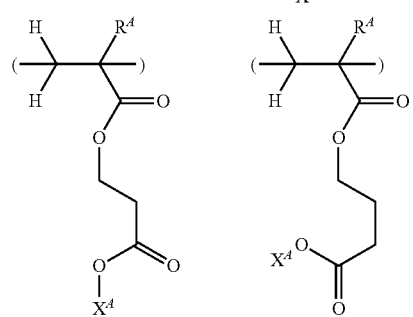

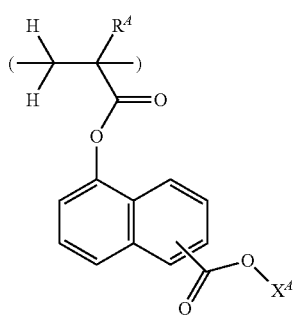

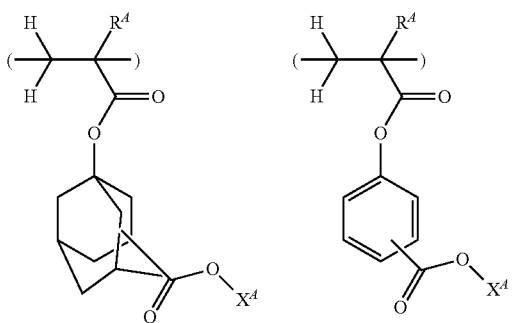

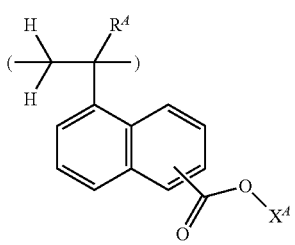

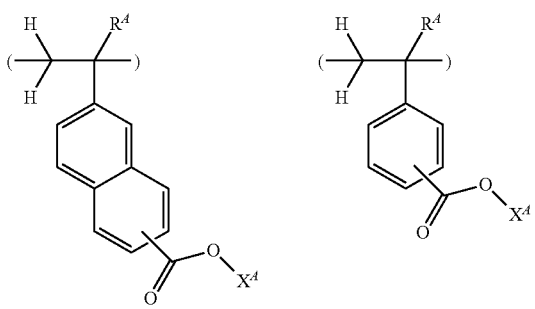

(B-10)

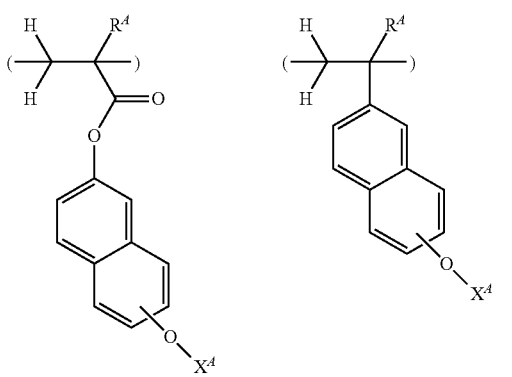

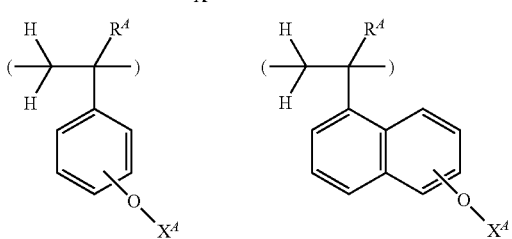

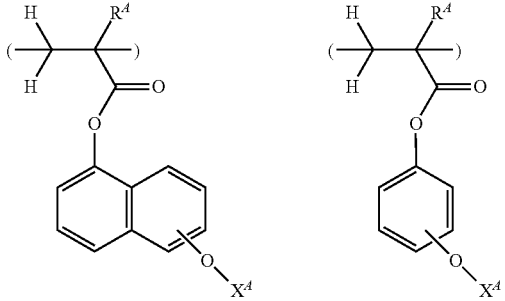

As the acid labile group X$^A$, a primary, secondary, or tertiary alkyl group is preferable. In each case of the phenolic hydroxy group and the carboxy group, distillation is the way for obtaining the polymerizable monomer to give a unit protected by a tertiary alkyl group, and accordingly, the tertiary alkyl group preferably has 4 to 18 carbon atoms. The tertiary carbon atom of the tertiary alkyl group may have an alkyl substituent including a linear, branched, or cyclic alkyl group with 1 to 15 carbon atoms optionally having an oxygen-containing functional group such as an ether bond or a carbonyl group, in which the alkyl substituents on the tertiary carbon atom may bond with each other to form a ring.

Illustrative examples of the preferable primary and secondary alkyl substituents include a methyl group, an ethyl group, a propyl group, an amyl group, an adamantyl group, a norbornyl group, a tetrahydrofuran-2-yl group, a 7-oxanorbornan-2-yl group, a cyclopentyl group, a 2-tetrahydrofuryl group, a tricyclo[5.2.1.0$^{2,6}$]decyl group, a 8-ethyl-8-tricyclo[5.2.1.0$^{2,6}$]decyl group, a 3-methyl-3-tetracyclo[4.4.0.1$^{2,5}$,1$^{7,10}$]dodecyl group, a tetracyclo[4.4.0.1$^{2,5}$,1$^{7,10}$]dodecyl group, and a 3-oxo-1-cyclohexyl group; illustrative examples of the tertiary alkyl group include a tert-butyl group, a tert-pentyl group, a 1-ethyl-1-methylpropyl group, a 1,1-diethylpropyl group, a 1,1,2-trimethylpropyl group, a 1-adamantyl-1-methylethyl group, a 1-methyl-1-(2-norbornyl)ethyl group, a 1-methyl-1-(tetrahydrofuran-2-yl)ethyl group, a 1-methyl-1-(7-oxanorbornan-2-yl)ethyl group, a 1-methylcyclopentyl group, a 1-ethylcyclopentyl group, a 1-propylcyclopentyl group, a 1-cyclopentylcyclopentyl group, a 1-cyclohexylcyclopentyl group, a 1-(2-tetrahydrofuryl)cyclopentyl group, a 1-(7-oxanorbornan-2-yl)cyclopentyl group, a 1-methylcyclohexyl group, a 1-ethylcyclohexyl group, a 1-cyclopentylcyclohexyl group, a 1-cyclohexylcyclohexyl group, a 2-methyl-2-norbornyl group, a 2-ethyl-2-norbornyl group, a 8-methyl-8-tricyclo[5.2.1.0$^{2,6}$]decyl group, a 8-ethyl-8-tricyclo[5.2.1.0$^{2,6}$]decyl group, a 3-methyl-3-tetracyclo[4.4.0.1$^{2,5}$,1$^{7,10}$]dodecyl group, a 3-ethyl-3-tetracyclo[4.4.0.1$^{2,5}$,1$^{7,10}$]dodecyl group, a 2-methyl-2-adamantyl group, a 2-ethyl-2-adamantyl group, a 1-methyl-3-oxo-1-cyclohexyl group, a 1-methyl-1-(tetrahydrofuran-2-yl)ethyl group, a 5-hydroxy-2-methyl-2-adamantyl group, and a 5-hydroxy-2-ethyl-2-adamantyl group; although not limited thereto.

<Acid Generator>

As the acid generator formulated to the first resist material used in the present invention, illustrative examples thereof include an acid generator shown by the following general formula (Z1), (Z2), or (Z3). Among these acid generators, the photo-acid generator shown by the following general formula (Z3) is particularly preferable to be contained.

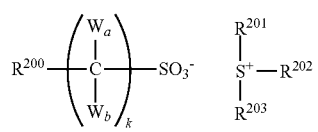  (Z1)

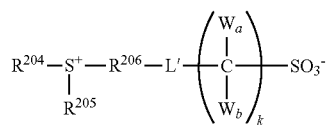  (Z2)

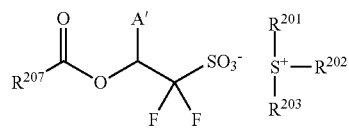  (Z3)

In the formulae, $R^{200}$ represents a hydrogen atom, a fluorine atom, or a linear, branched, or cyclic monovalent hydrocarbon group having 1 to 35 carbon atoms optionally containing a hetero atom; $W_a$ and $W_b$ each independently represent any of a hydrogen atom, a fluorine atom, and a trifluoromethyl group; "k" is an integer of 1 to 4; $R^{201}$, $R^{202}$, and $R^{203}$ each independently represent any of a substituted or unsubstituted linear or branched alkyl group, alkenyl group, and oxoalkyl group having 1 to 10 carbon atoms or any of a substituted or unsubstituted aryl group, aralkyl group, and aryloxoalkyl group having 6 to 18 carbon atoms, and alternatively, any two or more of $R^{201}$, $R^{202}$, and $R^{203}$ may be bonded with each other to form a ring with the sulfur atom in the formula; $R^{204}$ and $R^{205}$ each independently represent a linear, branched, or cyclic monovalent hydrocarbon group having 1 to 20 carbon atoms that may be substituted with a hetero atom or intervened with a hetero atom; $R^{206}$ represents a linear, branched, or cyclic divalent hydrocarbon group having 1 to 20 carbon atoms that may be substituted with a hetero atom or intervened with a hetero atom; $R^{207}$ represents a linear, branched, or cyclic monovalent hydrocarbon group having 1 to 35 carbon atoms that may contain a hetero atom; alternatively, any two or more of $R^{204}$, $R^{205}$, and $R^{206}$ may be bonded with each other to form a ring with the sulfur atom in the formula; L' represents a single bond or a linear, branched, or cyclic divalent hydrocarbon group having 1 to 20 carbon atoms that may be substituted with a hetero atom or intervened with a hetero atom; and A' represents a hydrogen atom or a trifluoromethyl group.

As the above acid generator that can be formulated, the ones having the following structures are exemplified, but the present invention is not limited thereto.

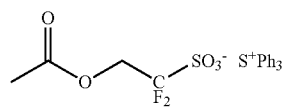

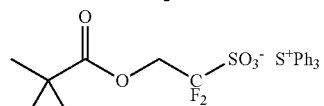

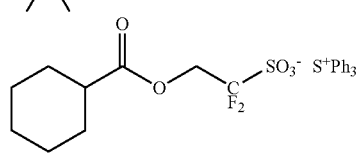

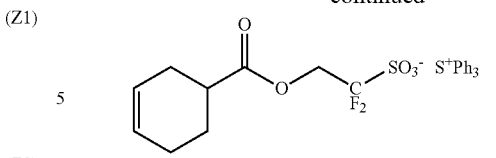

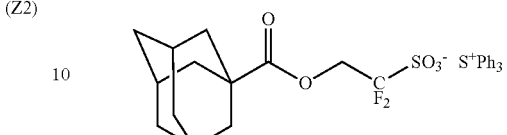

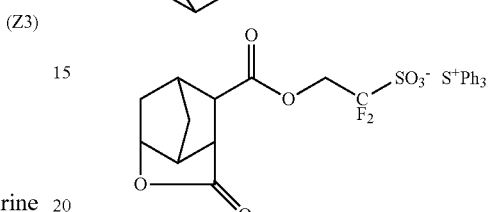

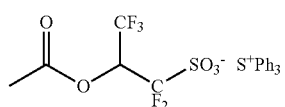

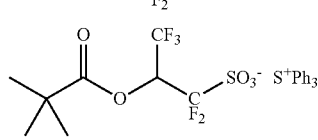

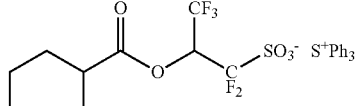

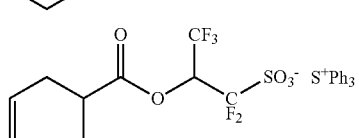

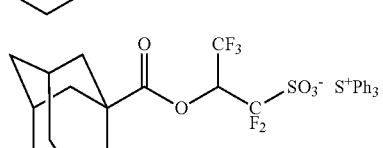

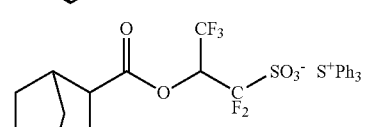

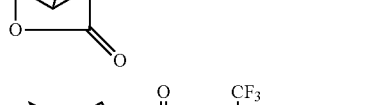

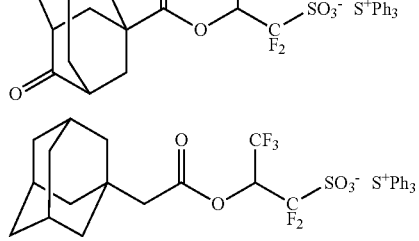

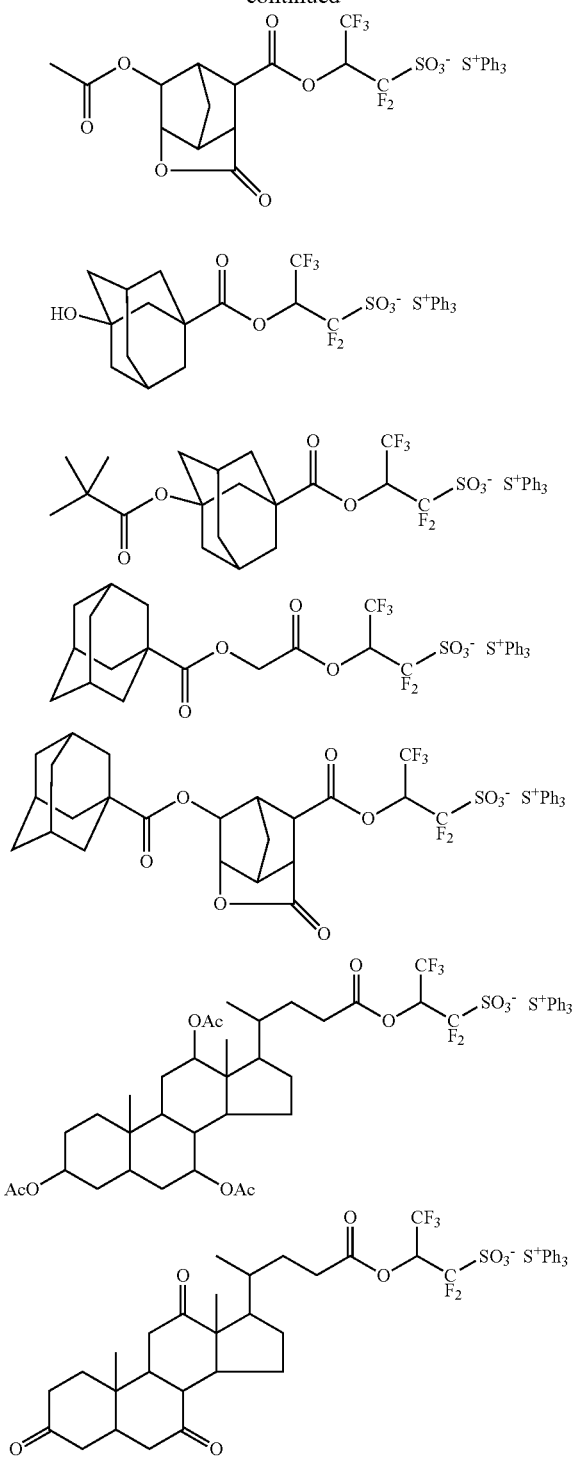
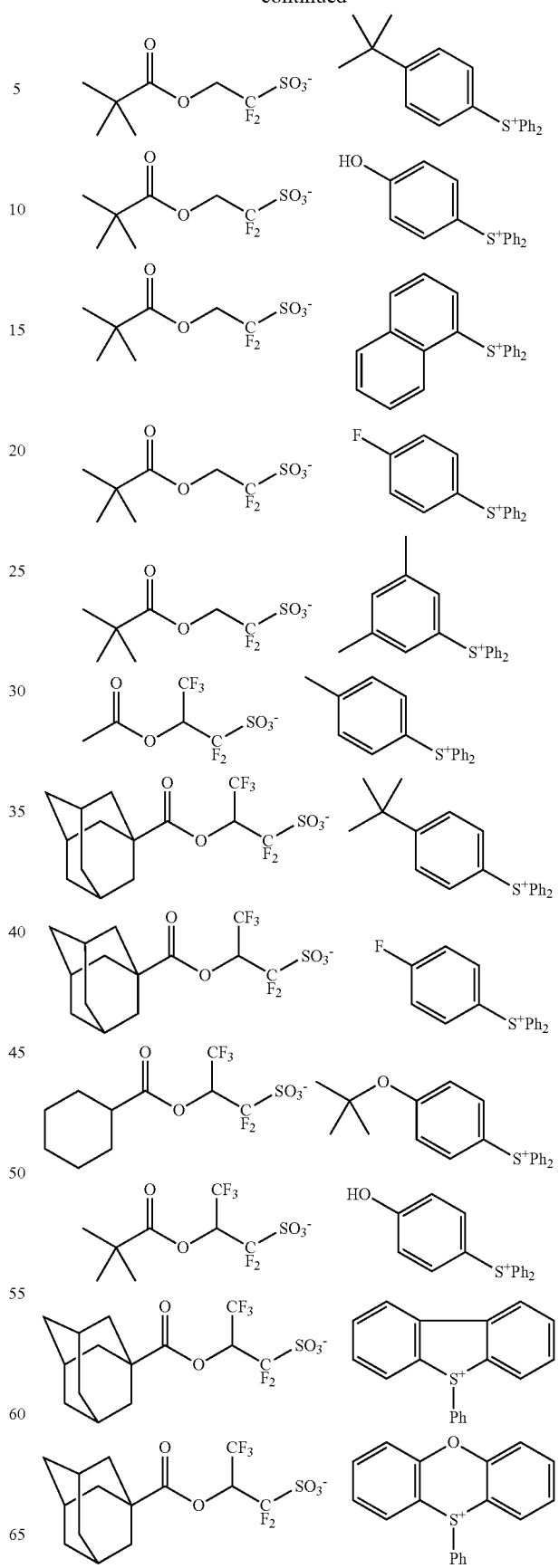
In the formulae, Ac represents an acetyl group, and Ph represents a phenyl group.

-continued
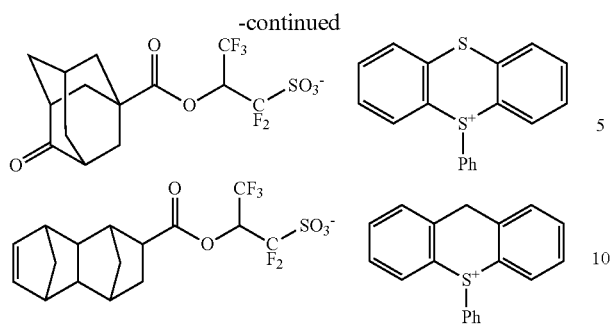 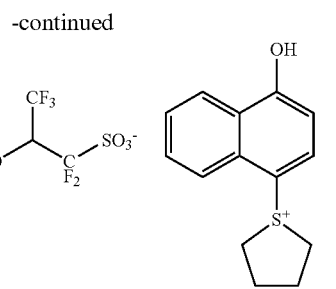
In the formulae, Ph represents a phenyl group.
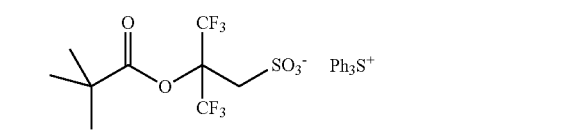
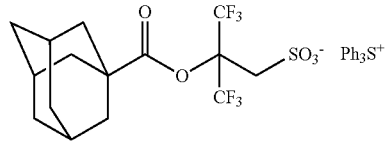
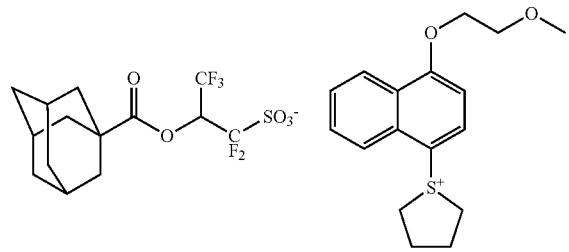
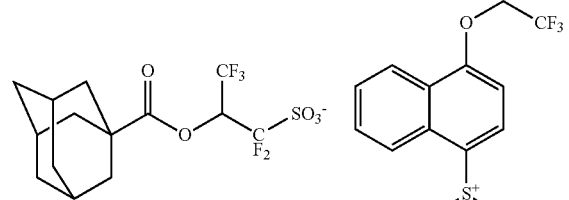
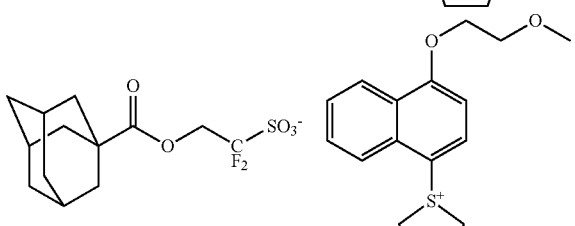
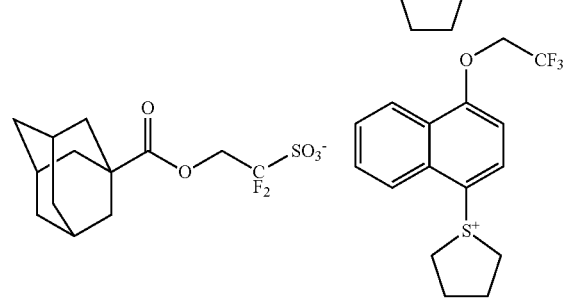
-continued
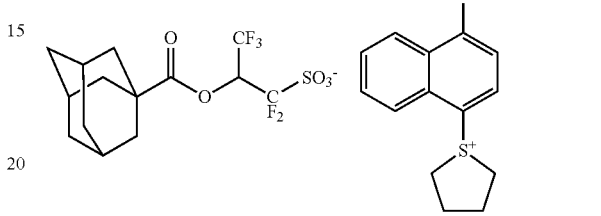
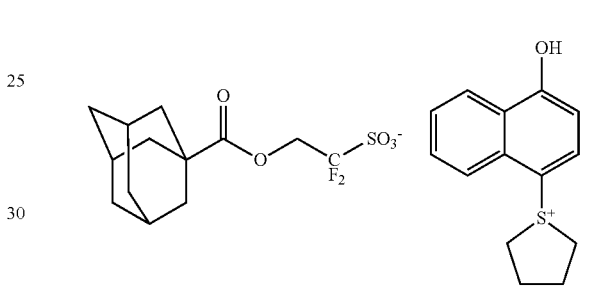
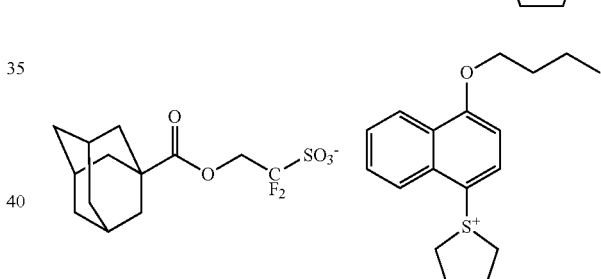
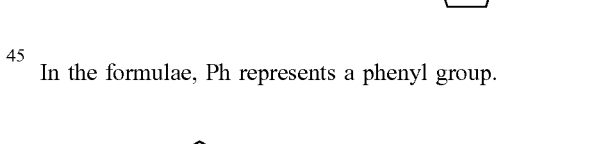
In the formulae, Ph represents a phenyl group.
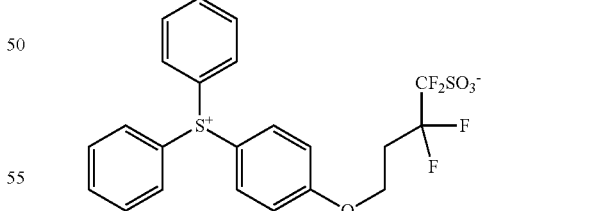
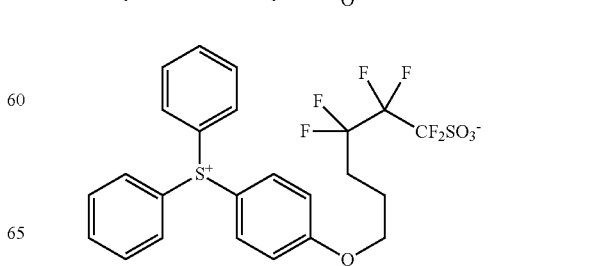

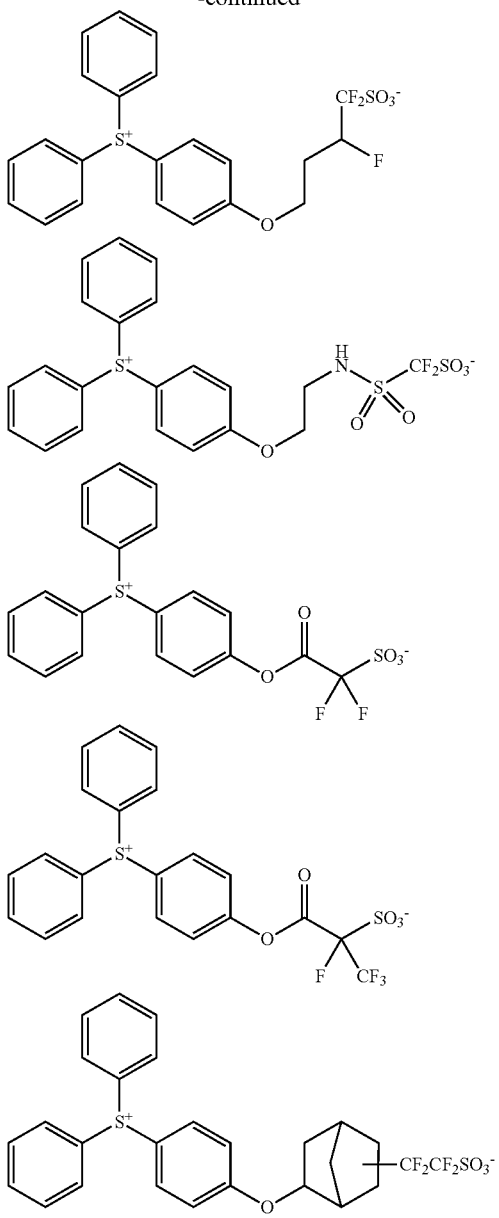

The formulation amount of the acid generator (photo-acid generator) is preferably 0 to 30 parts by mass, particularly 0 to 20 parts by mass relative to 100 parts by mass of the base resin (thermosetting compound).

[Second Resist Material]

The second resist material contains a component (A) of at least one element selected from the group consisting of a metal compound as well as a hydrolysate, a condensate, and a hydrolysis condensate of the metal compound, together with a sensitizer.

<Component (A)>

The component (A) is preferably at least one element selected from a metal compound shown by the following general formula (A-1) as well as a hydrolysate, a condensate, and a hydrolysis condensate of the metal compound, and/or at least one element selected from a condensate and a hydrolysis condensate of a metal compound shown by the following general formula (A-2) and the metal compound shown by the general formula (A-1).

$$M(OR^{1A})_4 \quad (A\text{-}1)$$

In the formula, M represents Ti, Zr, or Hf; and $R^{1A}$ represents a monovalent organic group having 1 to 20 carbon atoms and 0 or 1 hydroxy group.

$$M'X \quad (A\text{-}2)$$

In the formula, M' represents Ti, Zr, or Hf; and X represents a divalent or trivalent alcohol shown by the following general formula (A-3).

$$R^{2A}(OH)_m \quad (A\text{-}3)$$

In the formula, $R^{2A}$ represents an m-valent organic group having 2 to 20 carbon atoms and 0 or 1 hydroxy group; and "m" is an integer of 2 or 3.

The monovalent organic group $R^{1A}$ in the general formula (A-1) may be any form of linear, branched, and cyclic, and illustrative examples thereof include monovalent saturated hydrocarbon groups such as a methyl group, an ethyl group, an n-propyl group, an isopropyl group, a cyclopropyl group, an n-butyl group, an isobutyl group, a sec-butyl group, a tert-butyl group, a cyclobutyl group, an n-pentyl group, an isopentyl group, a sec-pentyl group, a tert-pentyl group, a neopentyl group, a cyclopentyl group, an n-hexyl group, a cyclohexyl group, an n-heptyl group, a cycloheptyl group, an n-octyl group, a cyclooctyl group, an n-nonyl group, a cyclononyl group, an n-decyl group, a cyclodecyl group, an adamantyl group, and a norbornyl group; monovalent unsaturated hydrocarbon groups such as a cyclohexenyl group, a cyclohexenylmethyl group, a cyclohexenylethyl group, a cycloheptenyl group, and a cyclopentadienyl group; aryl groups such as a phenyl group, a tolyl group, a xylyl group, a methoxyphenyl group, and a naphthyl group; aralkyl groups such as a benzyl group, a phenethyl group, and a methoxybenzyl group; and a monovalent group containing a heterocycle such as a tetrahydrofurfuryl group.

The monovalent organic group may have one hydroxy group. As the monovalent organic group having a hydroxy group, the ones having tertiary alcohol structure are particularly preferable.

When M is titanium, illustrative examples of the metal compound shown by the general formula (A-1) include titanium methoxide, titanium ethoxide, titanium propoxide, titanium isopropoxide, titanium butoxide, titanium pentoxide, titanium hexyloxide, titanium cyclopentoxide, titanium cyclohexyloxide, titanium allyloxide, titanium phenoxide, titanium methoxyethoxide, titanium ethoxyethoxide, titanium 2-ethyl-1,3-hexandiolate, titanium 2-ethylhexoxide, titanium tetrahydrofurfuryloxide, titanium bis(triethanolaminato)diisopropoxide, titanium dipropoxy bis(ethyl acetoacetato), titanium dibutoxy bis(ethyl acetoacetato), titanium dipropoxy bis(2,4-pentanedionato), and titanium dibutoxy bis(2,4-pentanedionato).

When M is zirconium, illustrative examples of the metal compound shown by the general formula (A-1) include methoxy zirconium, ethoxy zirconium, propoxy zirconium, butoxy zirconium, phenoxy zirconium, zirconium dibutoxide bis(2,4-pentanedionate), and zirconium dipropoxide bis (2,2,6,6-tetramethyl-3,5-heptanedionate).

When M is hafnium, illustrative examples of the metal compound shown by the general formula (A-1) include hafnium methoxide, hafnium ethoxide, hafnium propoxide, hafnium butoxide, hafnium pentoxide, hafnium hexyloxide, hafnium cyclopentoxide, hafnium cyclohexyloxide, hafnium allyloxide, hafnium phenoxide, hafnium methoxyethoxide, hafnium ethoxyethoxide, hafnium dipropoxy bis (ethyl acetoacetate), hafnium dibutoxy bis(ethyl acetoacetate), hafnium dipropoxy bis(2,4-pentanedionato), and hafnium dibutoxy bis(2,4-pentanedionato).

In the general formula (A-3), $R^{24}$ represents an m-valent organic group having 2 to 20 carbon atoms, and "m" is 2 or 3. The m-valent organic group is preferably a group obtained by removing m-number of hydrogen atoms from a hydrocarbon having 2 to 20 carbon atoms. The m-valent organic group may be any form of linear, branched, and cyclic, and illustrative examples thereof include groups derived from aliphatic hydrocarbon such as alkane, alkene, and alkyne as well as aromatic hydrocarbon. The group is particularly preferably a group derived from alkane selected from ethane, propane, butane, pentane, hexane, heptane, octane, nonane, decane, undecane, dodecane, tridecane, tetradecane, pentadecane, hexadecane, heptadecane, octadecane, nonadecane, and icosane.

The divalent or trivalent alcohol shown by the formula (A-3) includes the following, but is not limited thereto.

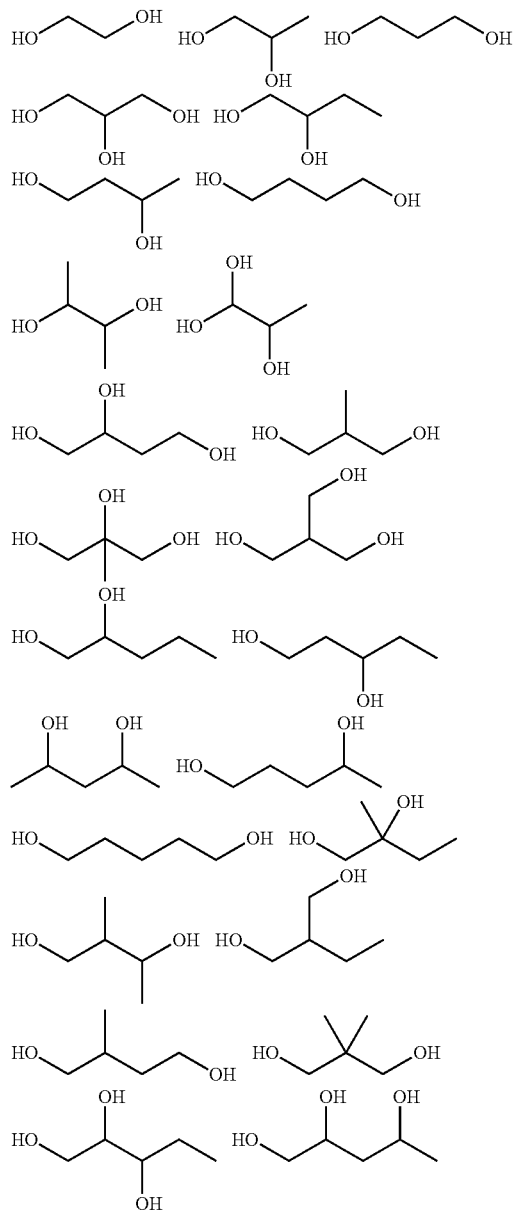

-continued

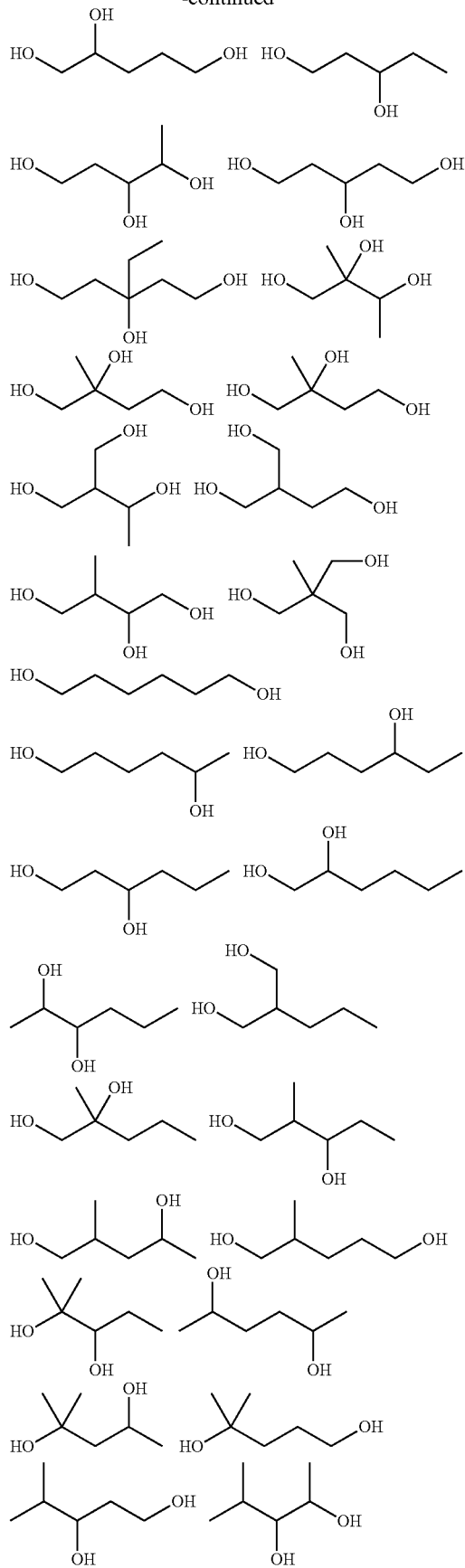

-continued
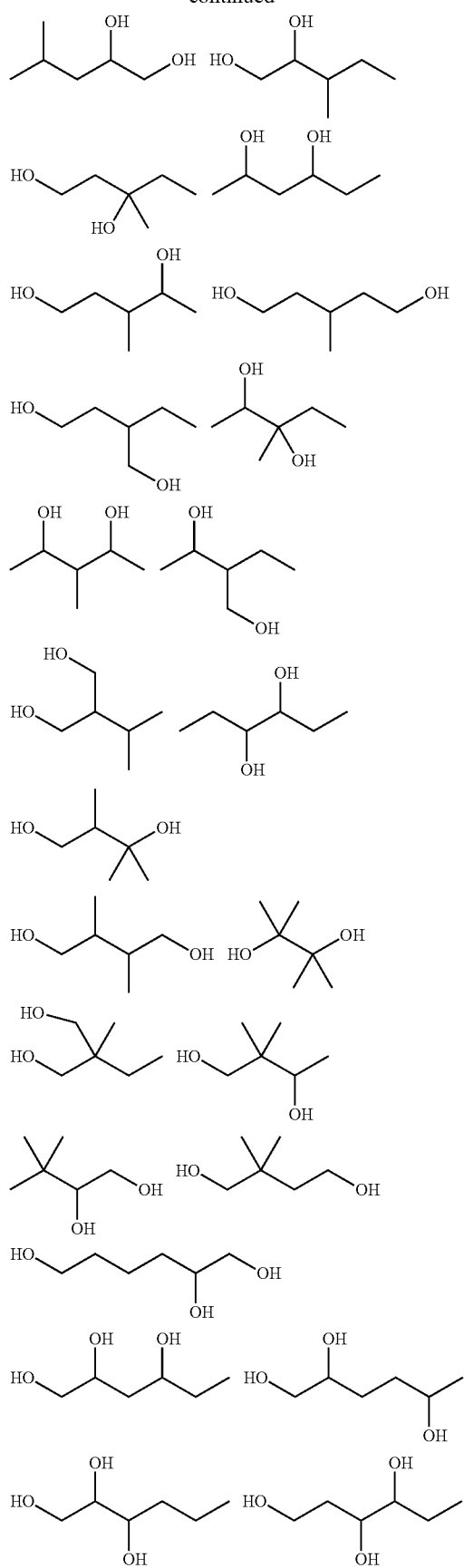
-continued
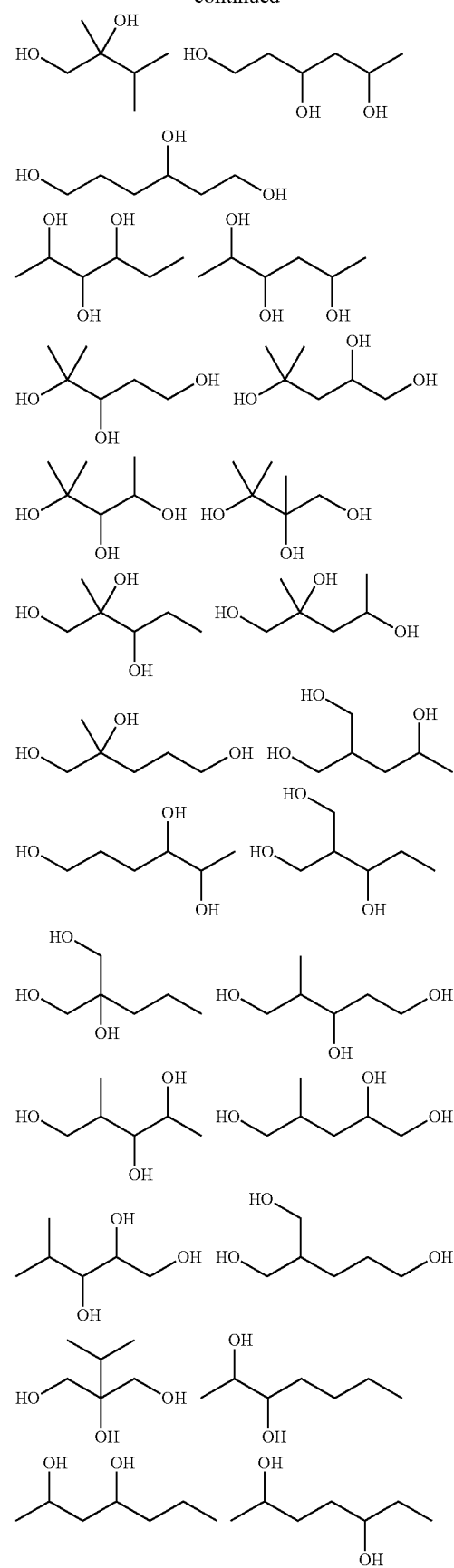

-continued
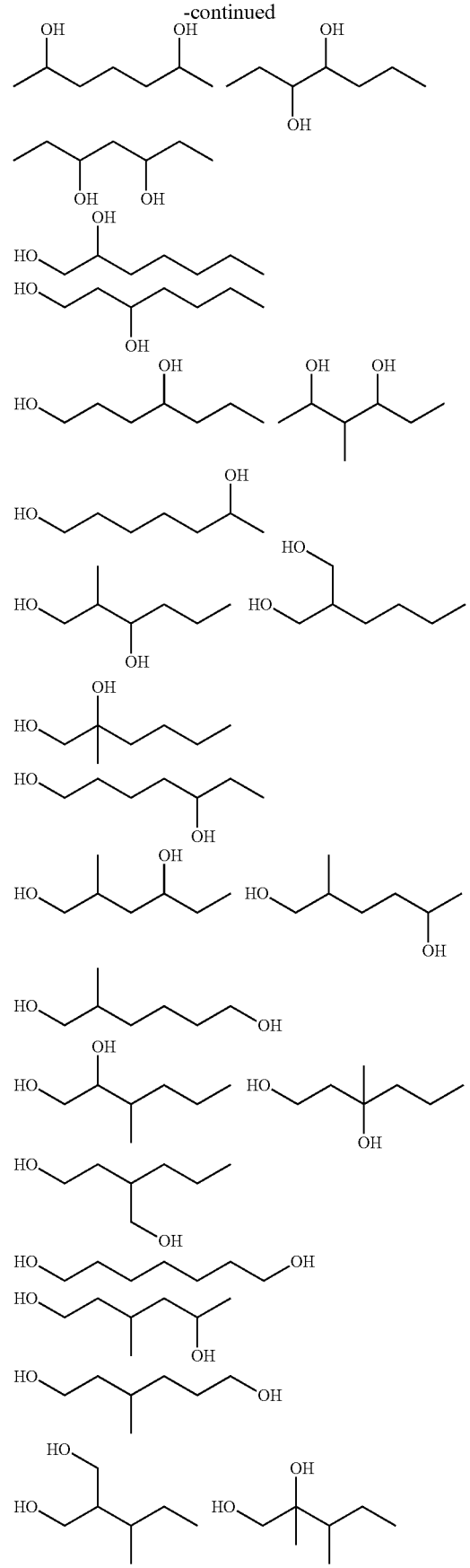
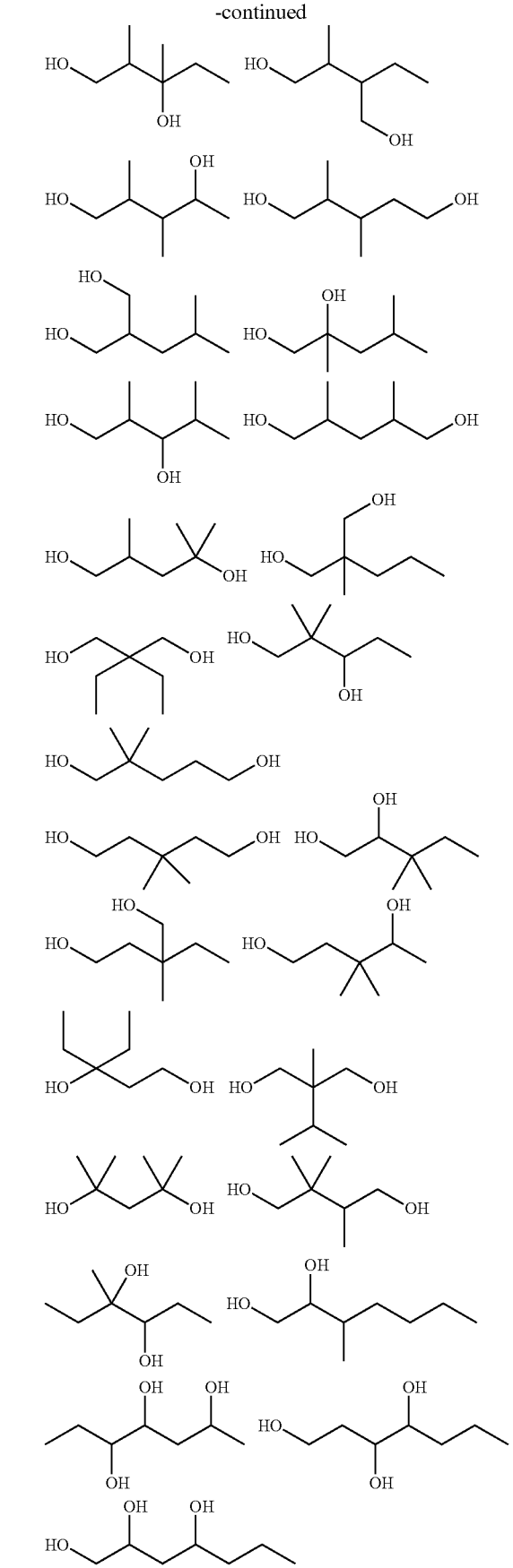

-continued
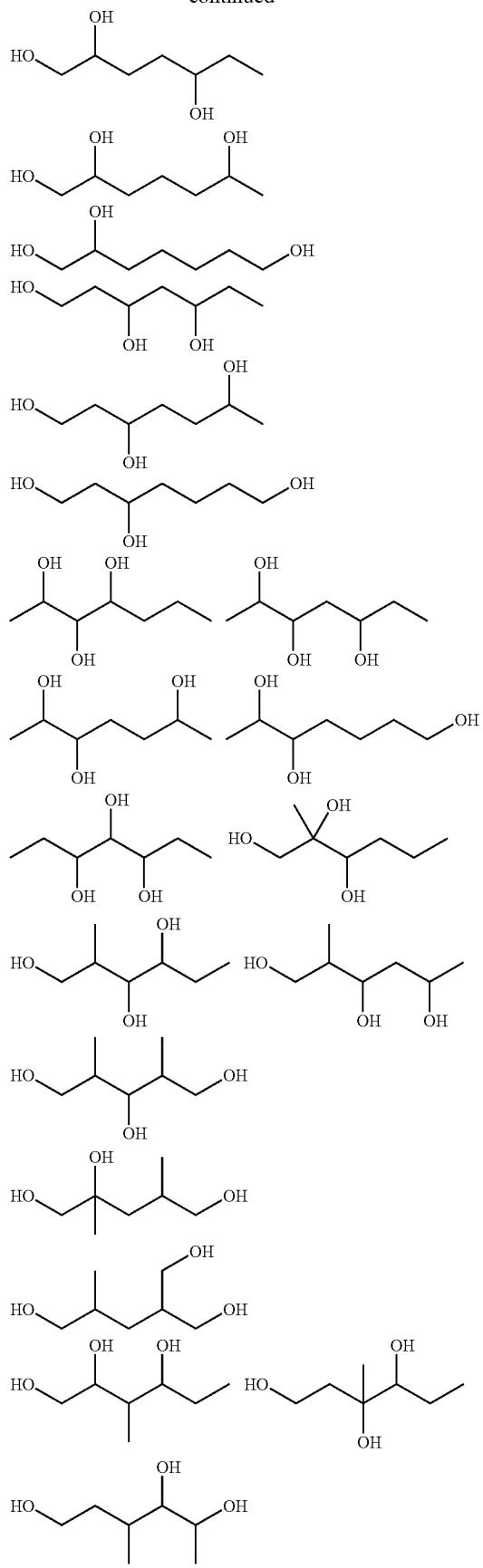
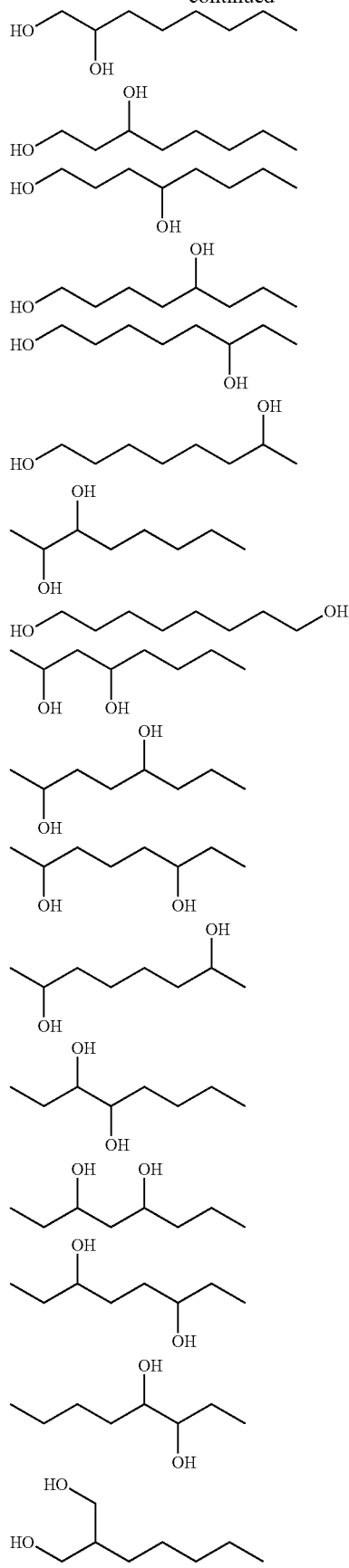

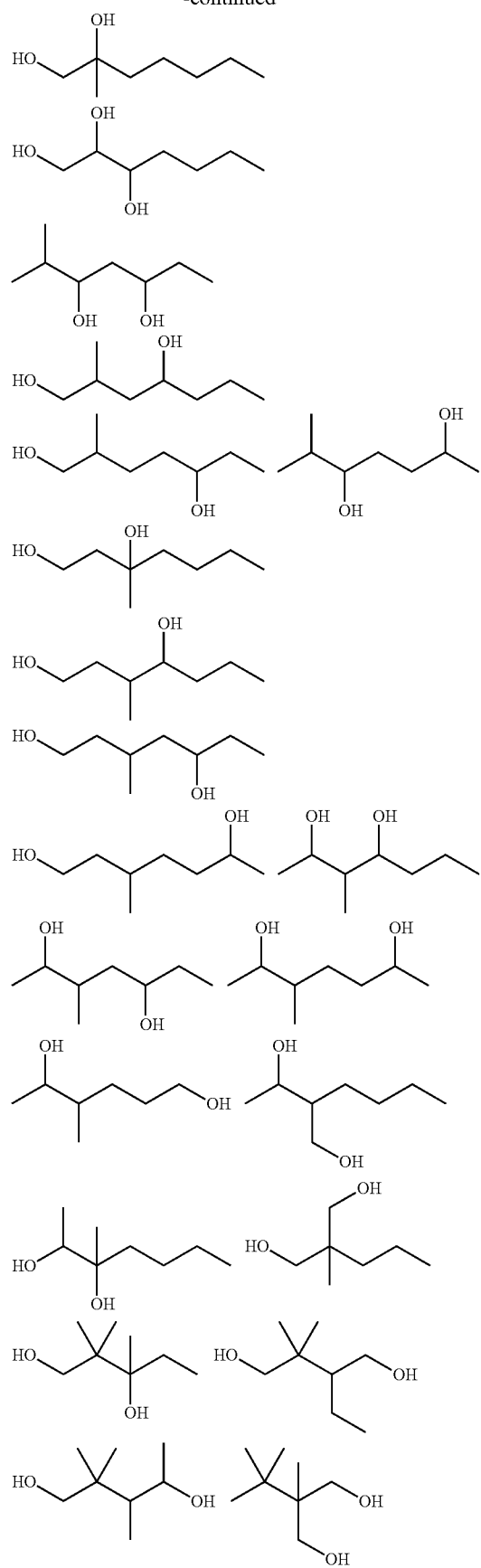
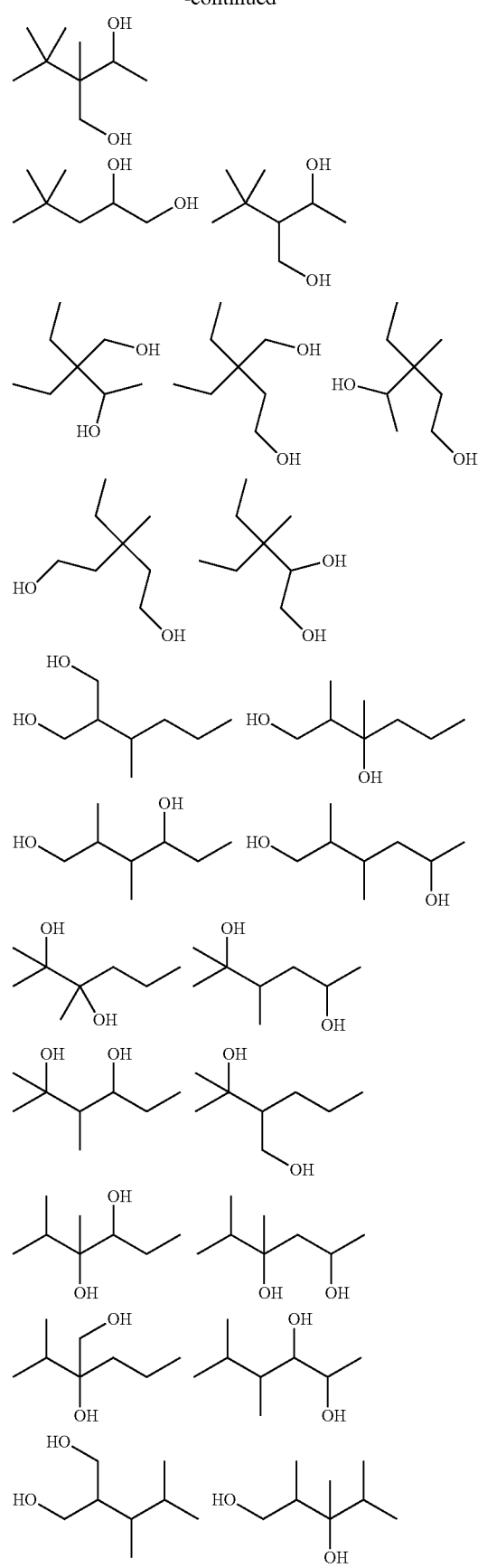

-continued
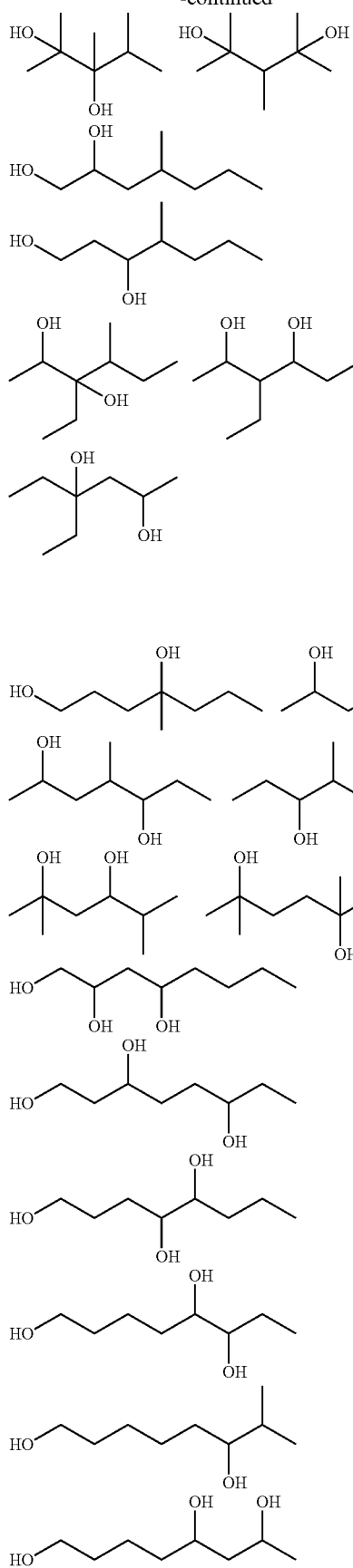
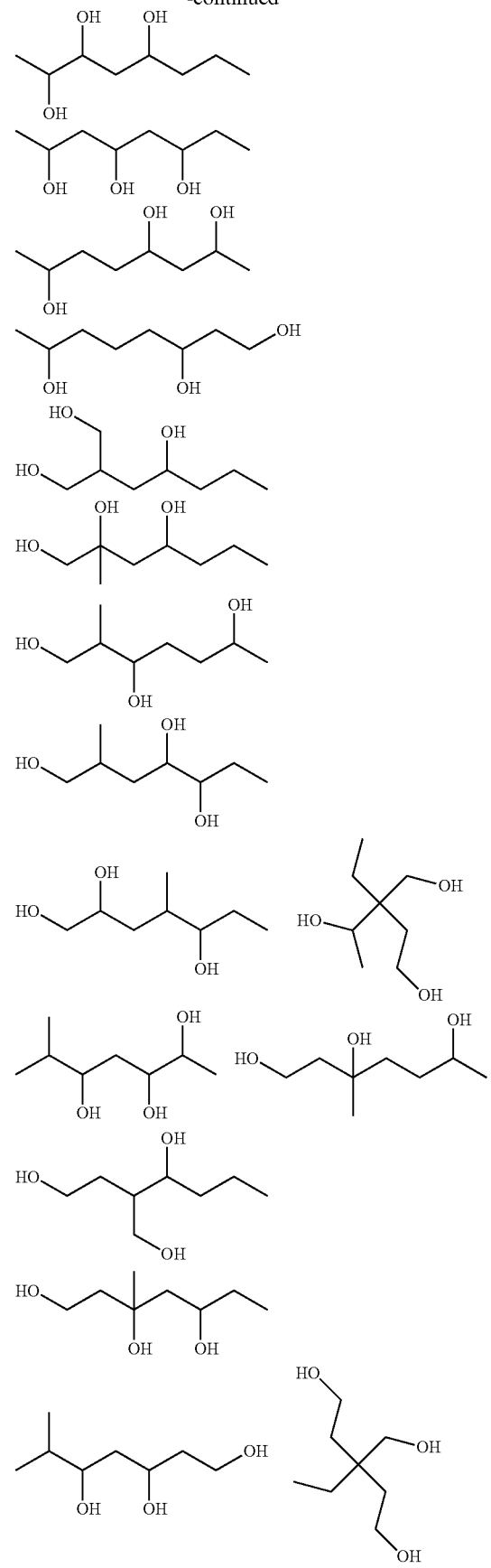

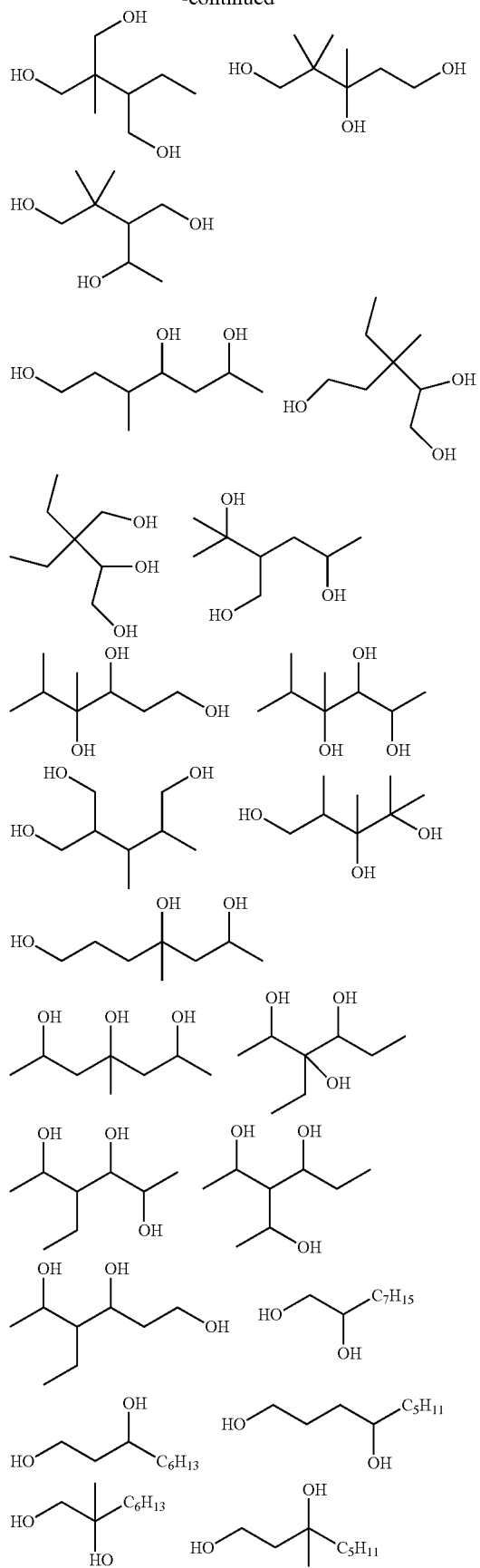
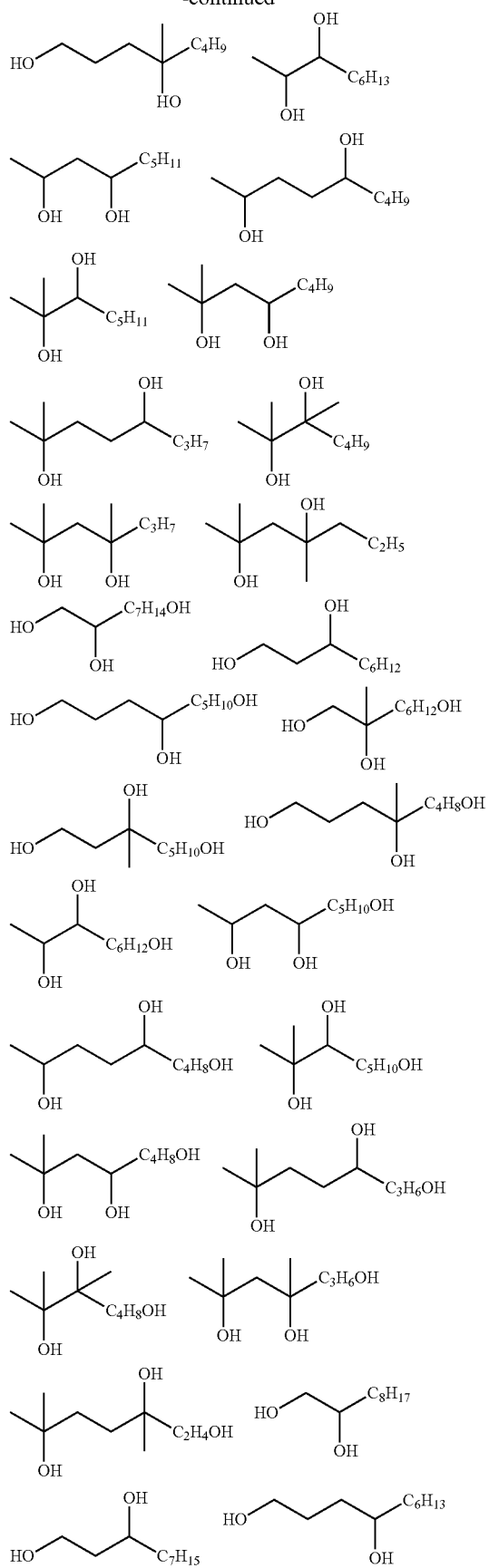

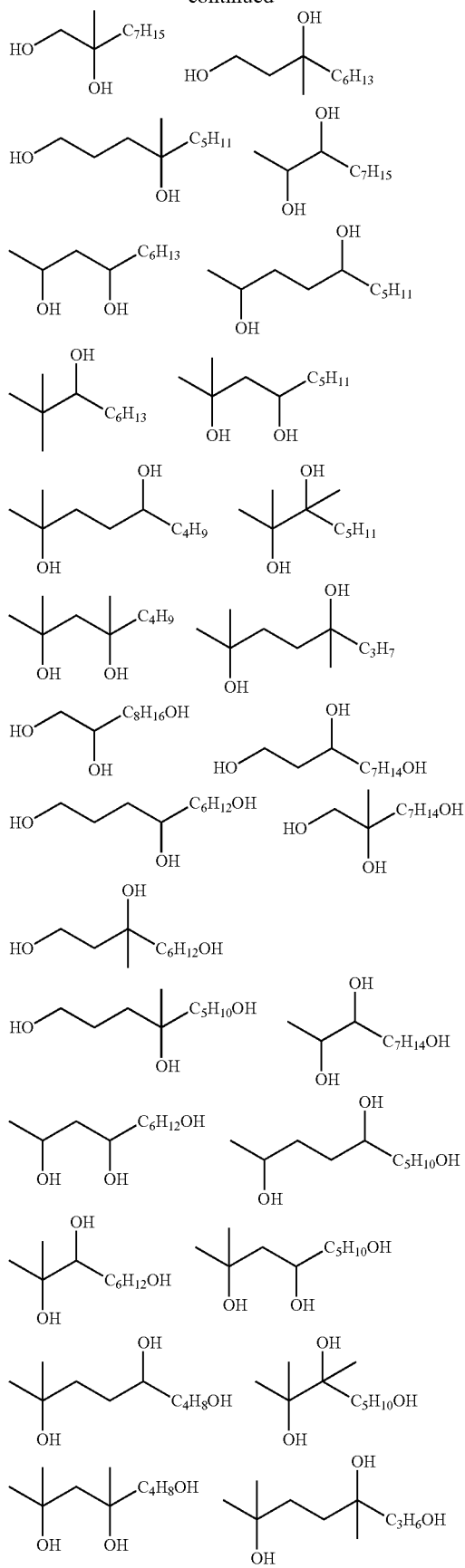
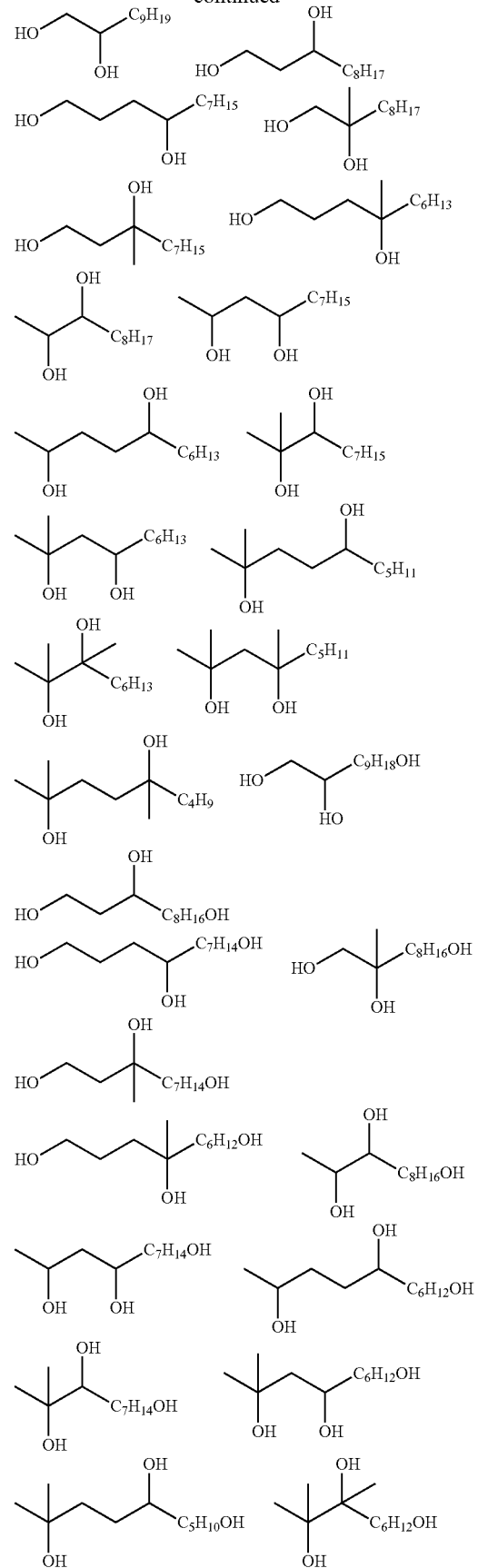

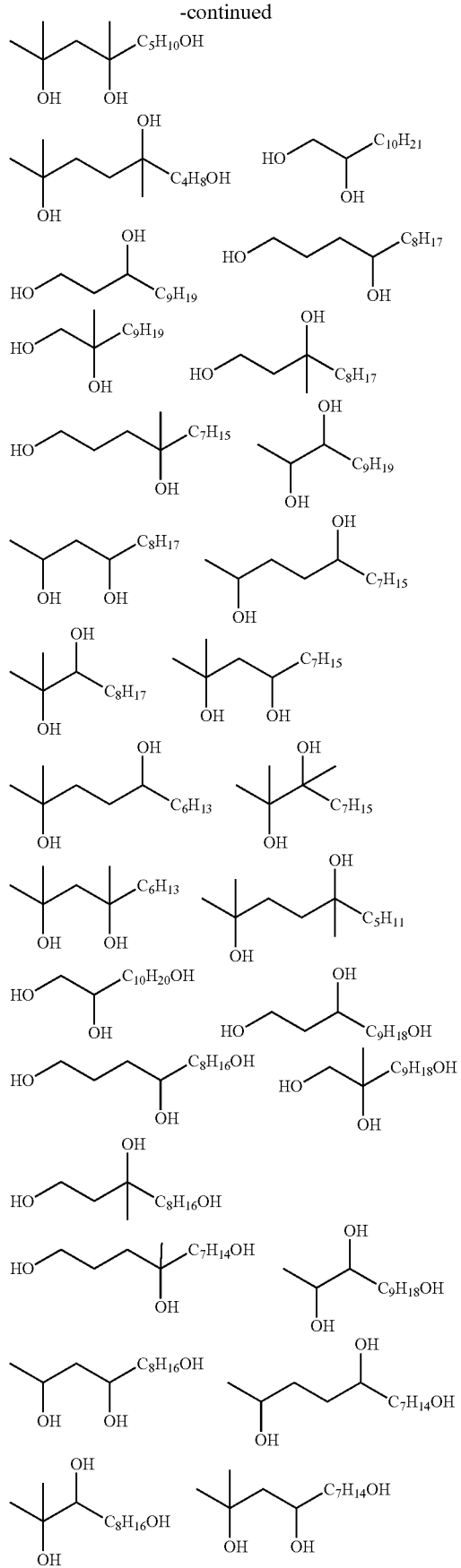
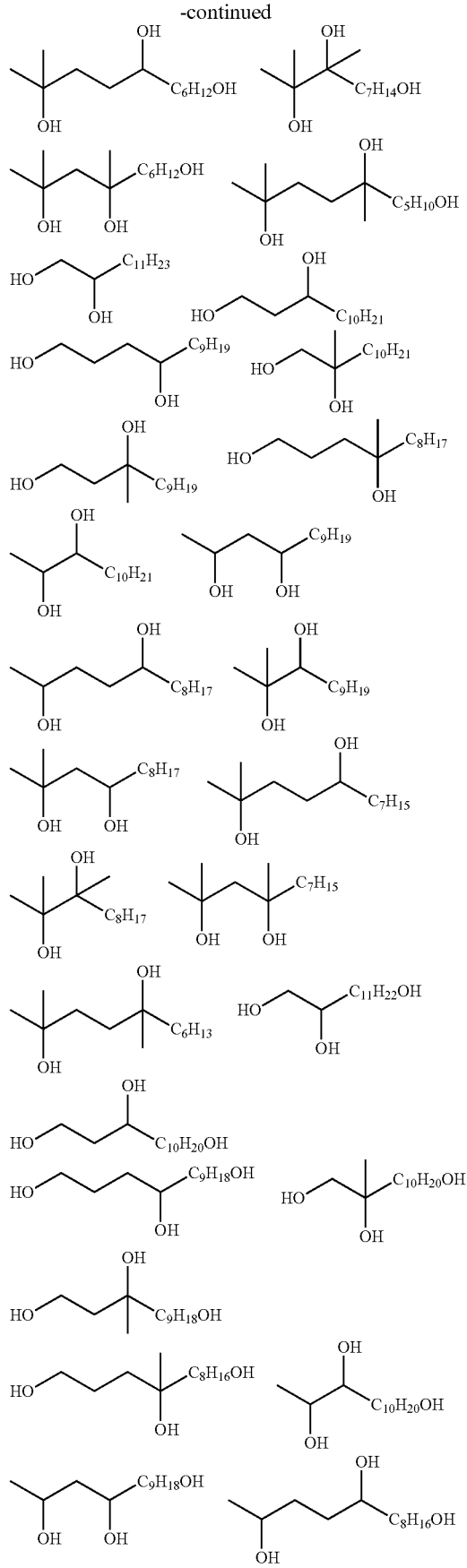

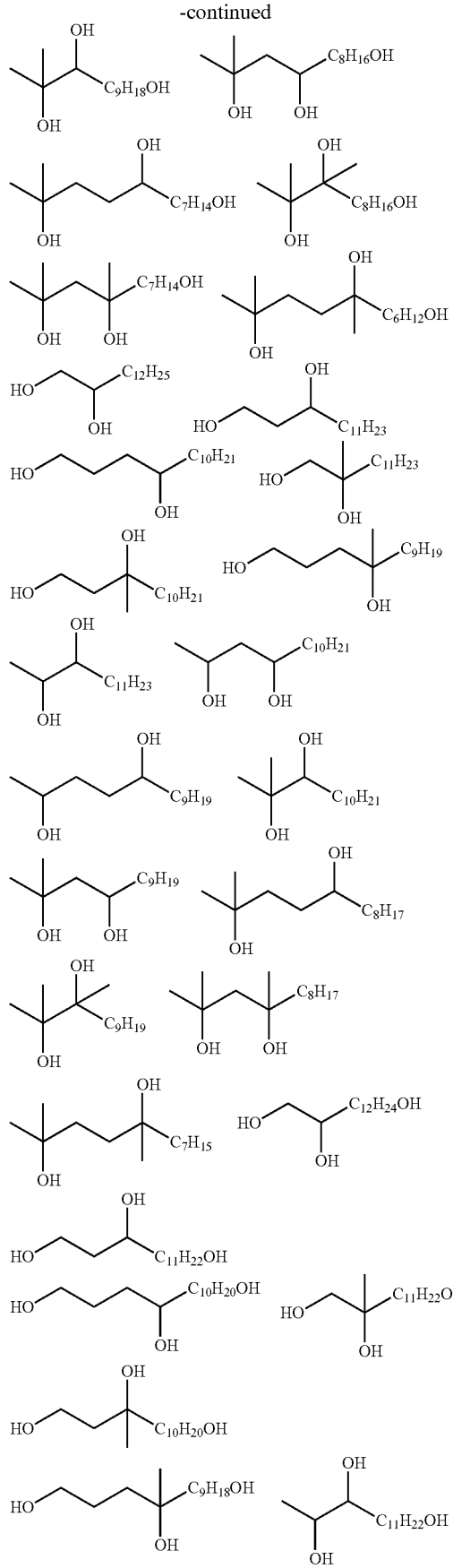

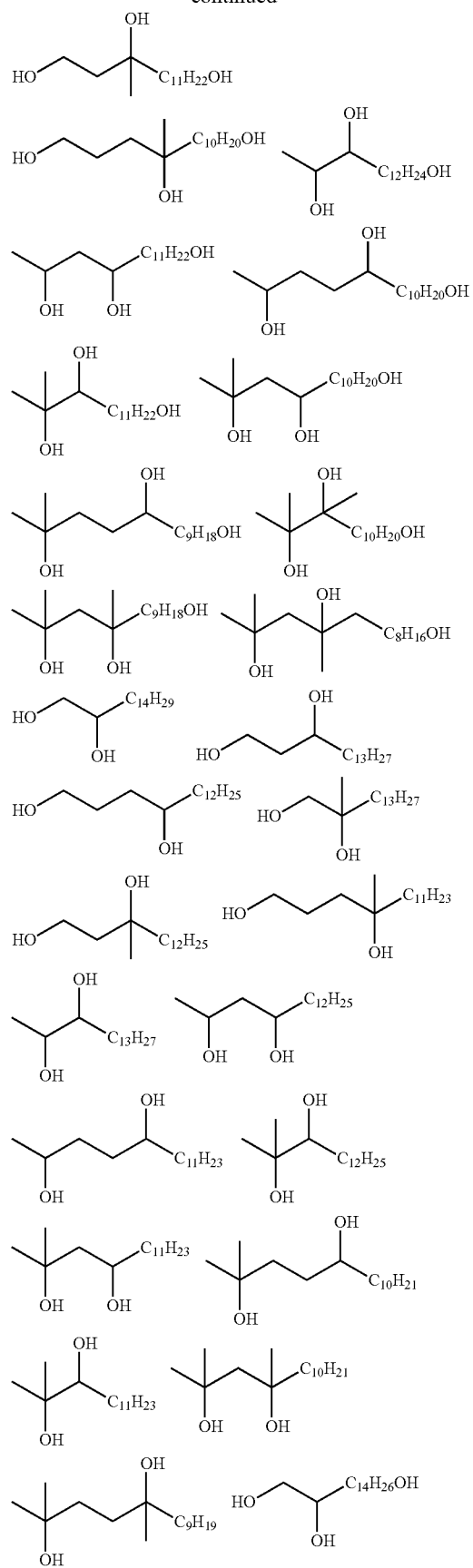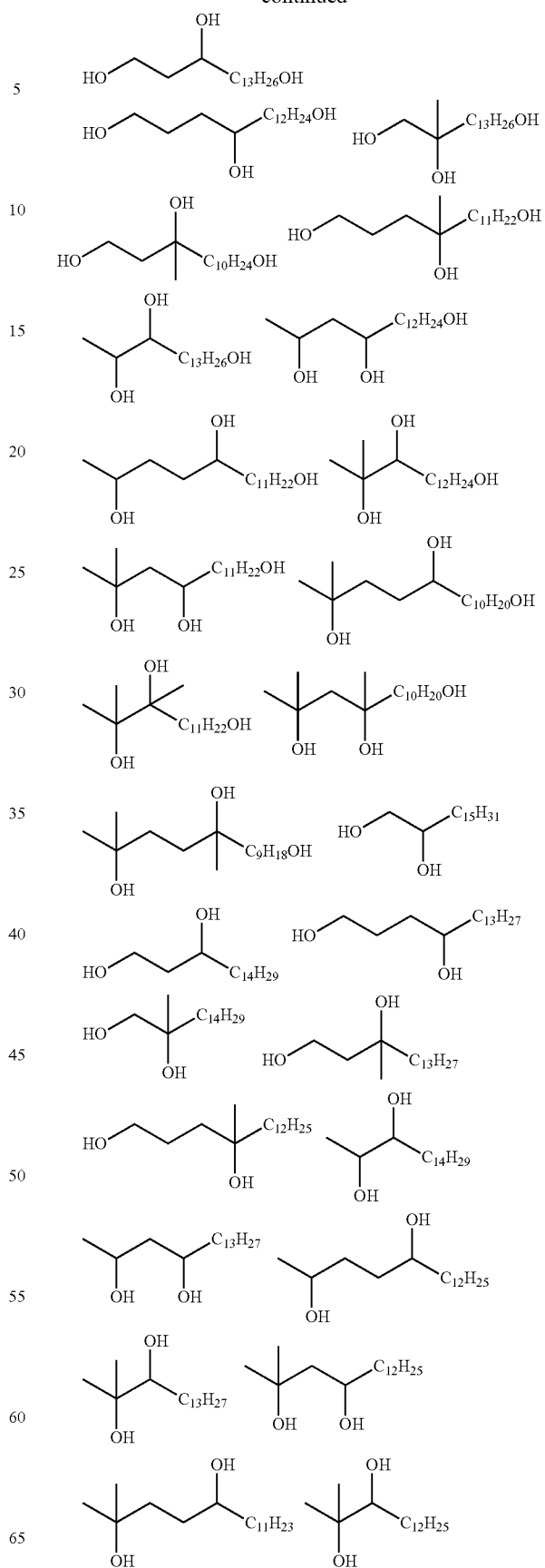

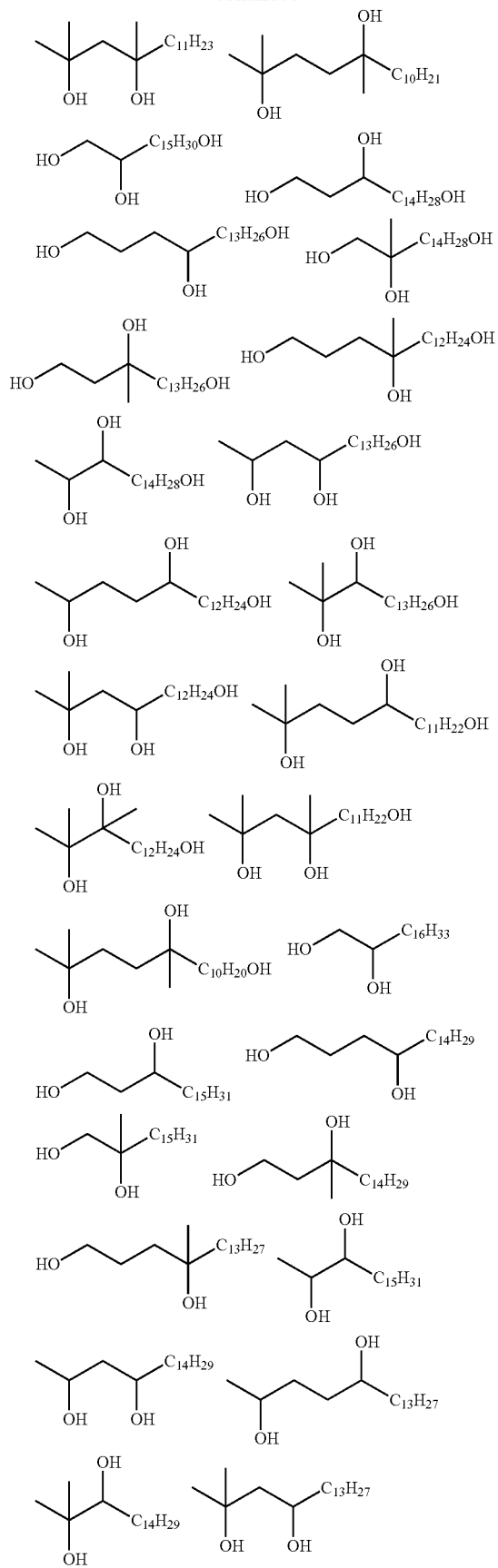
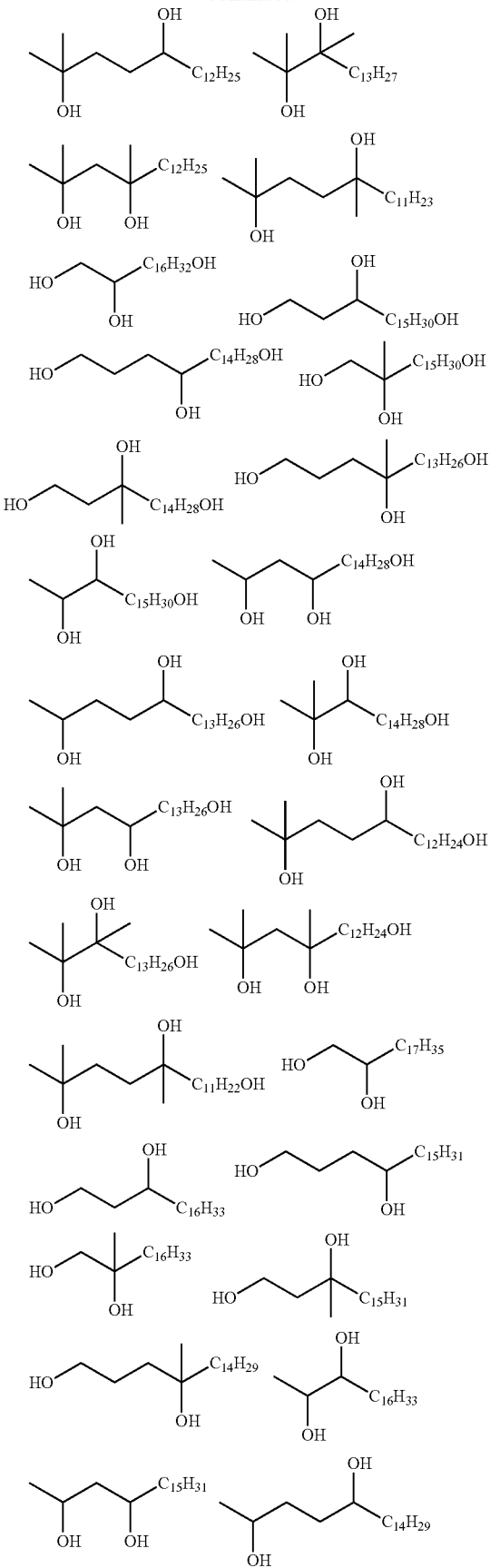

-continued
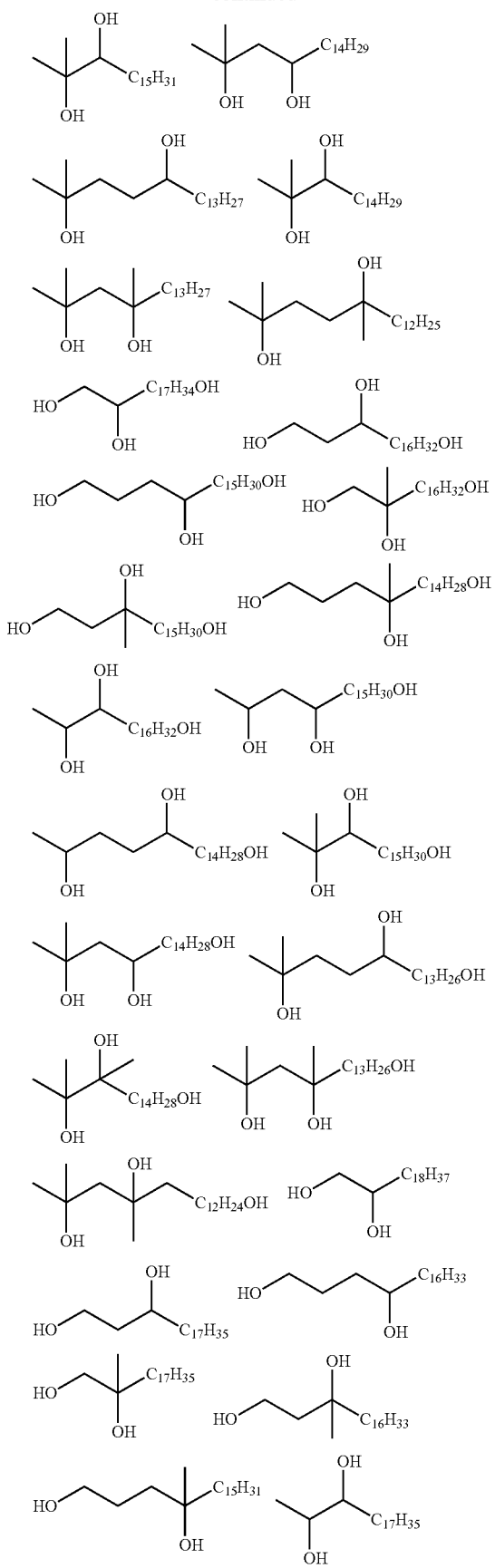
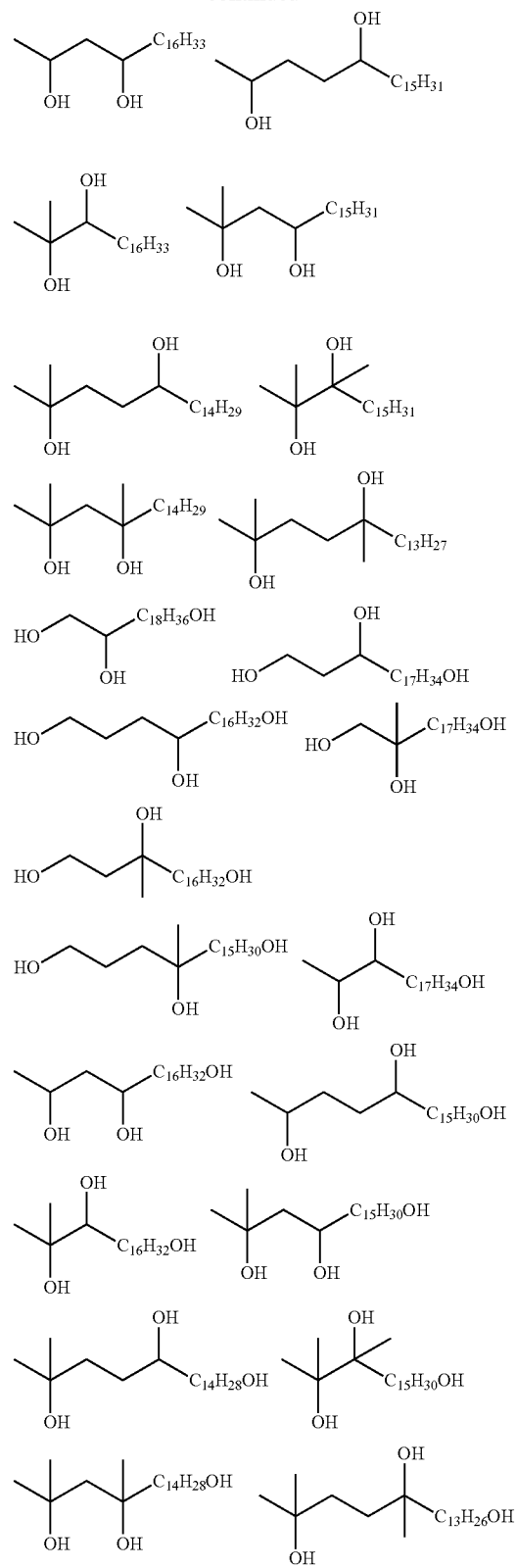
Among them, as the divalent or trivalent alcohol shown by the general formula (A-3), the ones having a tertiary alcohol structure is preferable. Illustrative examples of the particularly preferable one include the following.

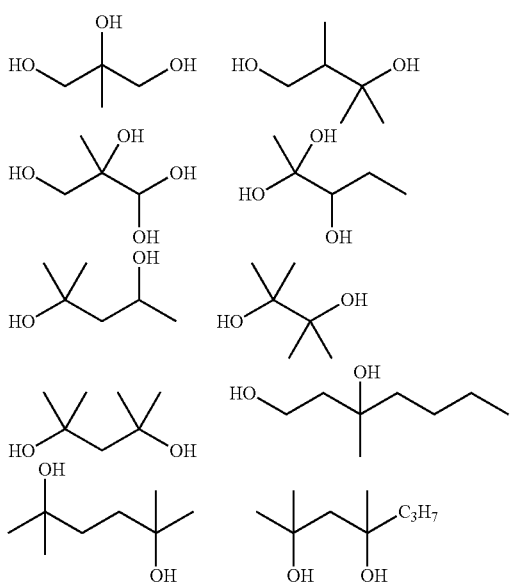

In view of the storage stability of a resist material, it is preferable that one or more tertiary alcohol structure be contained in either or both of the metal compound shown by the formula (A-1) and the divalent or trivalent alcohol shown by the formula (A-3). In each organic group bonding to a metal atom through its oxygen atom, the carbon atom ordinarily varies the solubility in solvents and heat stability depending on the surrounding skeleton structure. The solubility of metal compounds in solvents (particularly, organic solvents) becomes higher in the order of the skeleton structure of a carbon atom contained in the organic group or a carbon atom in the reactant alcohol such that the solubility becomes higher as the structure shifts from a primary alcohol structure to a secondary alcohol structure, and to a tertiary alcohol structure. Having a tertiary alcohol structure introduced thereto, the metal compound shows increased solubility in organic solvents, thereby making it possible to prevent precipitation of metal compound and so on more effectively. The thermal decomposition temperature of the metal compound becomes lower in the order of the skeleton structure of a carbon atom such that the thermal decomposition temperature becomes lower as the structure shifts from a primary alcohol structure to a secondary alcohol structure, and to a tertiary alcohol structure. The tertiary alcohol structure introduced thereto makes it possible to form a film more certainly in a temperature range of 100 to 350° C., which is usable for an ordinary process of forming a semiconductor device.

The hydrolysate or the hydrolysis condensate of a metal compound shown by the general formula (A-1) can be produced by hydrolysis or hydrolysis and condensation (hereinafter referred to as hydrolysis condensation) of the metal compound shown by the general formula (A-1) without using a catalyst or in the presence of an acid or alkaline catalyst.

The reaction product of a metal compound shown by the general formula (A-1) and a metal compound shown by the general formula (A-2) can be obtained as a reaction product of the metal compound shown by the general formula (A-1) or a hydrolysate or a hydrolysis condensate of the metal compound, together with a divalent or trivalent alcohol shown by the general formula (A-3). Such a reaction product can be produced by hydrolysis or hydrolysis and condensation (hereinafter referred to as hydrolysis condensation) of the metal compound shown by the general formula (A-1) or a hydrolysate or a hydrolysis condensate of the metal compound, together with the divalent or trivalent alcohol shown by the general formula (A-3), without using a catalyst or in the presence of an acid or alkaline catalyst.

As the acid catalyst, one or more compound can be used selected from inorganic acid, aliphatic sulfonic acid, aromatic sulfonic acid, aliphatic carboxylic acid, and aromatic carboxylic acid. Illustrative examples of the acid catalyst include hydrofluoric acid, hydrochloric acid, hydrobromic acid, sulfuric acid, nitric acid, perchloric acid, phosphoric acid, methanesulfonic acid, benzenesulfonic acid, toluenesulfonic acid, formic acid, acetic acid, propionic acid, oxalic acid, malonic acid, maleic acid, fumaric acid, and benzoic acid. The amount of the acid catalyst to be used is, preferably $10^{-6}$ to 10 mol, more preferably $10^{-3}$ to 5 mol, still more preferably $10^{-4}$ to 1 mol, for example, relative to 1 mol of titanium monomer.

Illustrative examples of the alkaline catalyst include methylamine, ethylamine, propylamine, butylamine, ethylene diamine, hexamethylene diamine, dimethylamine, diethylamine, ethylmethylamine, trimethylamine, triethylamine, tripropylamine, tributylamine, cyclohexylamine, dicyclohexylamine, monoethanolamine, diethanolamine, dimethyl monoethanolamine, monomethyl diethanolamine, triethanolamine, diazabicyclooctane, diazabicyclocyclononene, diazabicycloundecene, hexamethylene tetramine, aniline, N,N-dimethylaniline, pyridine, N,N-dimethyl ethanolamine, N,N-diethyl ethanolamine, N-(β-aminoethyl)ethanolamine, N-methyl ethanolamine, N-methyl diethanolamine, N-ethyl ethanolamine, N-n-butyl ethanolamine, N-n-butyl diethanolamine, N-tert-butyl ethanolamine, N-tert-butyl diethanolamine, N,N-dimethylaminopyridine, pyrrole, piperazine, pyrrolidine, piperidine, picoline, tetramethylammonium hydroxide, corrin hydroxide, tetrapropylammonium hydroxide, tetrabutylammonium hydroxide, ammonia, lithium hydroxide, sodium hydroxide, potassium hydroxide, barium hydroxide, and calcium hydroxide. The amount of the alkaline catalyst to be used is, preferably $10^{-6}$ to 10 mol, more preferably $10^{-5}$ to 5 mol, still more preferably $10^{-4}$ to 1 mol, for example, relative to 1 mol of titanium monomer.

In each of the hydrolysis and the hydrolysis condensation to obtain an intended compound from the raw material compound described above, the amount of water is preferably 0.01 to 10 mol, more preferably 0.05 to 5 mol, still more preferably 0.1 to 3 mol relative to 1 mol of the hydrolysable substituent bonded to the raw material compound. The addition of 10 mol or less is economical because the reaction does not necessitate a too large apparatus and is preferable because the stability of the metal compound is not impaired.

The hydrolysis condensation reaction may be started by an operation method of adding a raw material compound to aqueous catalyst solution. In this case, an organic solvent may be added to the aqueous catalyst solution, the raw material compound may be previously diluted with an organic solvent, or the both operation may be conducted. The reaction temperature is preferably 0 to 200° C., more preferably 5 to 150° C. The reaction time is preferably 0.5 to 24 hours, more preferably 1 to 12 hours. The reaction is preferably conducted by the method of adding a raw material compound dropwise while keeping the temperature at 5 to 150° C., followed by aging at 20 to 150° C. for 1 to 12 hours.

In another operation of the reaction, the hydrolysis reaction is started by adding water or an organic solvent containing water to a raw material compound or an organic solvent containing the raw material compound. In this case, the catalyst may be added to the raw material compound, may be added to an organic solvent containing the raw material compound, or may be previously added to water or an organic solvent containing water. The reaction temperature is preferably 0 to 200° C., more preferably 5 to 150° C. The reaction is preferably conducted by the method of adding a raw material compound dropwise while keeping the temperature at 5 to 150° C., followed by aging at 20 to 150° C. for 1 to 12 hours.

As the organic solvent that can be added to the aqueous catalyst solution or that can dilute the metal compound, preferable examples include methanol, ethanol, 1-propanol, 2-propanol, 1-butanol, 2-butanol, 2-methyl-1-propanol, acetone, acetonitrile, tetrahydrofuran, toluene, hexane, ethyl acetate, cyclohexanone, methyl pentyl ketone, butanediol monomethyl ether, propylene glycol monomethyl ether, ethylene glycol monomethyl ether, butanediol monoethyl ether, propylene glycol monoethyl ether, ethylene glycol monoethyl ether, propylene glycol dimethyl ether, diethylene glycol dimethyl ether, propylene glycol monomethyl ether acetate, propylene glycol monoethyl ether acetate, ethyl pyruvate, butyl acetate, methyl 3-methoxypropionate, ethyl 3-ethoxypropionate, tert-butyl acetate, tert-butyl propionate, propylene glycol mono-tert-butyl ether acetate, γ-butyrolactone, acetylacetone, methyl acetoacetate, ethyl acetoacetate, propyl acetoacetate, butyl acetoacetate, methyl pivaloylacetate, methyl isobutyloylacetate, methyl caproylacetate, methyl lauroylacetate, 1,2-ethanediol, 1,2-propanediol, 1,2-butanediol, 1,2-pentanediol, 2,3-butanediol, 2,3-pentanediol, glycerin, diethylene glycol, hexylene glycol, and a mixture thereof.

The organic solvent is preferably used in an amount of 0 to 1,000 mL, more preferably 0 to 500 mL relative to 1 mol of the metal compound. The use of organic solvent in an amount of 1,000 mL or less is economical because the reaction vessel is not too large.

Subsequently, the catalyst is subjected to neutralization reaction in accordance with needs. In this case, the acid or alkali for the neutralization is preferably used in an amount of 0.1 to 2 equivalents relative to the acid or alkali used as a catalyst, and may be any material to neutralize the catalyst.

Then, the by-products such as alcohol formed by the hydrolysis condensation reaction is preferably removed from the reaction solution. In this operation, the reaction solution is preferably heated to the temperature, which depends on the added organic solvent and the type of the by-products formed through the reaction, in a range of 0 to 200° C., more preferably 10 to 150° C., still more preferably 15 to 150° C. In this operation, the pressure varies depending on the organic solvent and by-products to be removed, the exhauster, the condenser, and the heating temperature, and is preferably reduced to atmospheric pressure or less, more preferably an absolute pressure of 80 kPa or less, still more preferably an absolute pressure of 50 kPa or less. Though it is difficult to know the precise amount of by-product removed in this operation, it is desirable to remove about 80 mass % or more of the formed by-products.

As a solvent finally added to the reaction solvent after removing the by-products, preferable examples include butanediol monomethyl ether, propylene glycol monomethyl ether, ethylene glycol monomethyl ether, butanediol monoethyl ether, propylene glycol monoethyl ether, ethylene glycol monoethyl ether, butanediol monopropyl ether, propylene glycol monopropyl ether, ethylene glycol monopropyl ether, ethylene glycol monobutyl ether, diethylene glycol monomethyl ether, diethylene glycol monoethyl ether, diethylene glycol monopropyl ether, diethylene glycol monobutyl ether, propylene glycol monobutyl ether, 1-butanol, 2-butanol, 2-methyl-1-propanol, 4-methyl-2-pentanol, acetone, tetrahydrofuran, toluene, hexane, ethyl acetate, cyclohexanone, methyl pentyl ketone, propylene glycol dimethyl ether, diethylene glycol dimethyl ether, dipentyl ether, propylene glycol monomethyl ether acetate, propylene glycol monoethyl ether acetate, ethyl pyruvate, butyl acetate, methyl 3-methoxypropionate, ethyl 3-ethoxypropionate, tert-butyl acetate, tert-butyl propionate, propylene glycol mono-tert-butyl ether acetate, γ-butyrolactone, methyl isobutyl ketone, cyclopentyl methyl ether, etc.

It is possible to control the molecular weight of a hydrolysis condensate of a metal compound shown by the general formula (A-1) or a reaction product thereof with a divalent or trivalent alcohol shown by the general formula (A-3) by adjusting the reaction conditions in the hydrolysis condensation not only by selecting the metal compound. The obtained compound preferably has a weight average molecular weight (Mw) of 100,000 or less, more preferably 200 to 50,000, still more preferably 300 to 30,000. When the Mw is 100,000 or less, foreign mattes or uneven coating are prevented from forming. Incidentally, the Mw in this invention is a value measured by gel permeation chromatography (GPC) in terms of polystyrene standard using RI as a detector and tetrahydrofuran as an elutriant.

Using such a component (A) for a resist material, the resist material excels in storage stability without changing the properties in a long period of time and it is possible to form a fine pattern in a good shape. The resist film formed from such a resist material is allowed to perform the reaction, when it is accelerated, by heating at a temperature in a lower range.

<Sensitizer>

As a sensitizer contained in the second resist material used for the present invention, illustrative examples thereof include a sensitizer of metal salt shown by the following general formula (B-1). This allows the second resist material to improve the sensitivity.

$$M^{m+}(Y^-) \quad (B-1)$$

In the formula, $M^{m+}$ represents an ion of a metal selected from Mg, Ca, Ce, Zn, Cu, In, Fe, Yb, Y, Tm, Sn, Ni, Sc, Hf, Nb, Ti, Zr, Ba, Ho, Tb, Lu, La, Ag, Eu, Dy, Gd, Rb, Sr, and Cs; $Y^-$ represents an alkylsulfonate ion, an arylsulfonate ion, an alkylsulfonimidate ion, or an alkylsulfonmethidate ion each having at least one fluorine atom; and "n" is an integer satisfying 1≤n≤4.

As $Y^-$, the ones shown by any of the following formulae (B-1-1) to (B-1-3) are preferable.

(B-1-1)
$$R^{1B}-SO_3^-$$

(B-1-2)
$$R^{2B}-SO_2-N^--SO_2-R^{3B}$$

(B-1-3)
$$R^{4B}-SO_2-C^--SO_2-R^{5B}$$

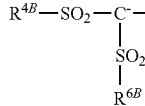
$$\begin{array}{c} | \\ SO_2 \\ | \\ R^{6B} \end{array}$$

In the formula (B-1-1), $R^{1B}$ represents a linear, branched, or cyclic alkyl group, alkenyl group, or alkynyl group having 5 to 30 carbon atoms, or an aryl group or aralkyl group having 6 to 30 carbon atoms, each having at least one fluorine atom and may have a halogen atom, an ether group, a thiol group, an ester group, a carbonate group, a carbonyl group, an amide group, an amino group, an azide group, a carbamate group, a nitro group, a cyano group, a hydroxy group, a carboxy group, a sulfo group, a sulfonate ester group, a sultone group, a lactone ring, or a lactam ring.

Illustrative examples of the sulfonate ion shown by the formula (B-1-1) include the following, but not limited thereto.

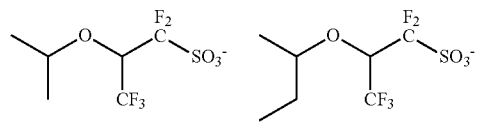

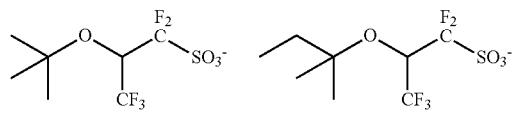

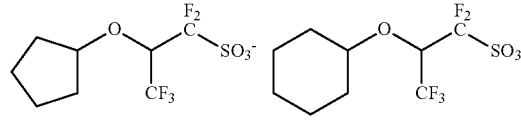

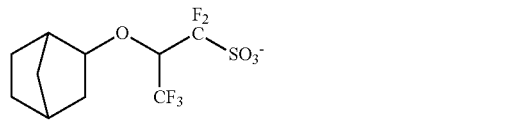

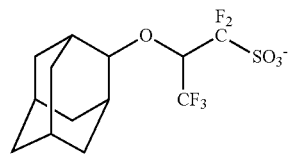

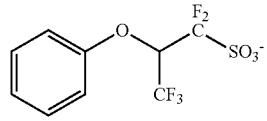

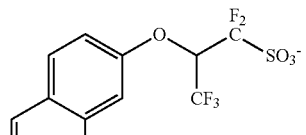

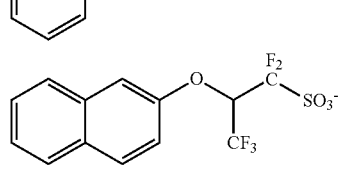

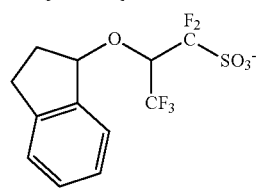

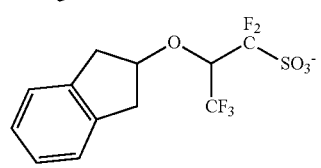

-continued

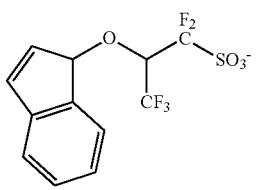

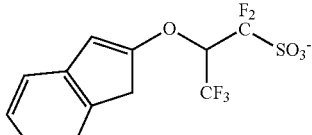

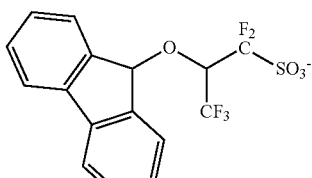

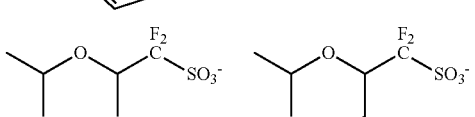

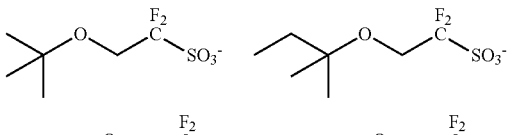

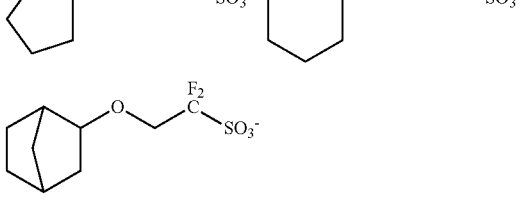

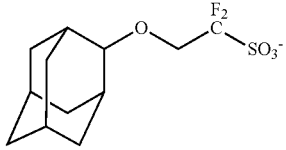

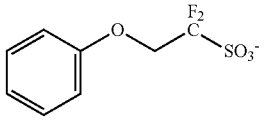

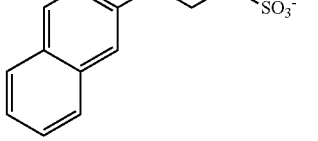

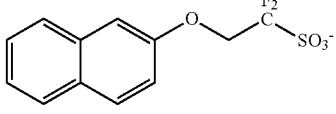

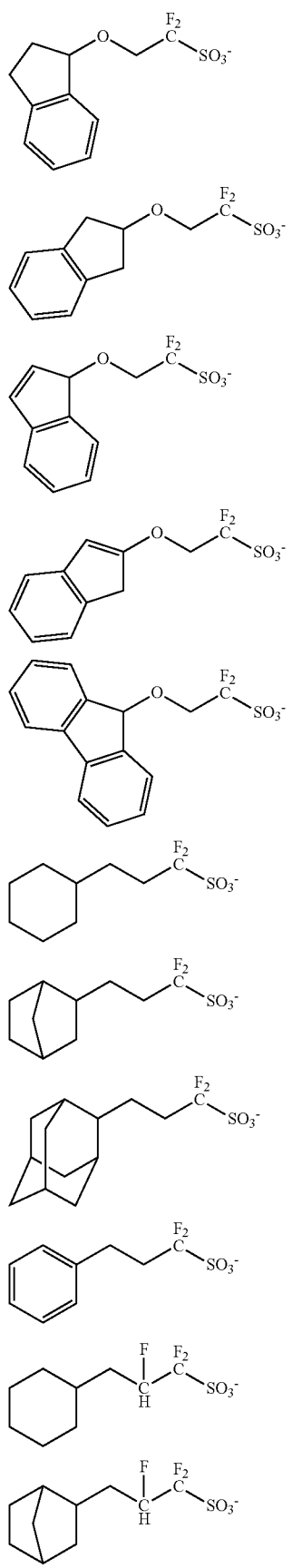
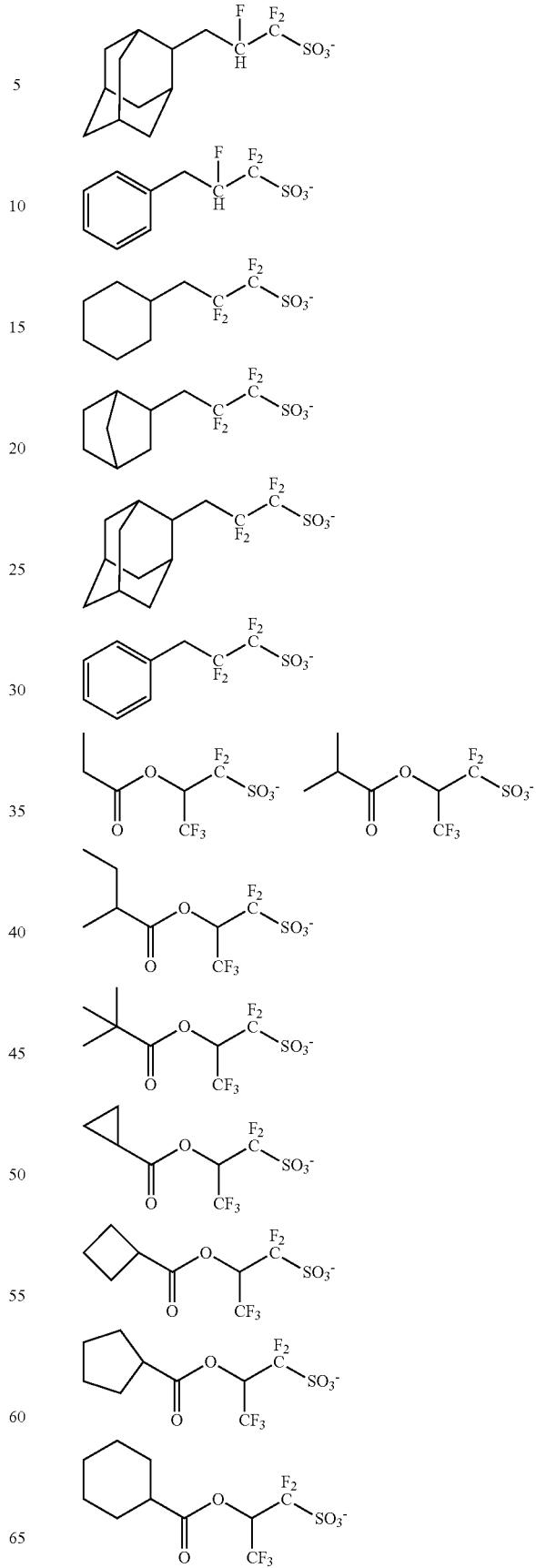

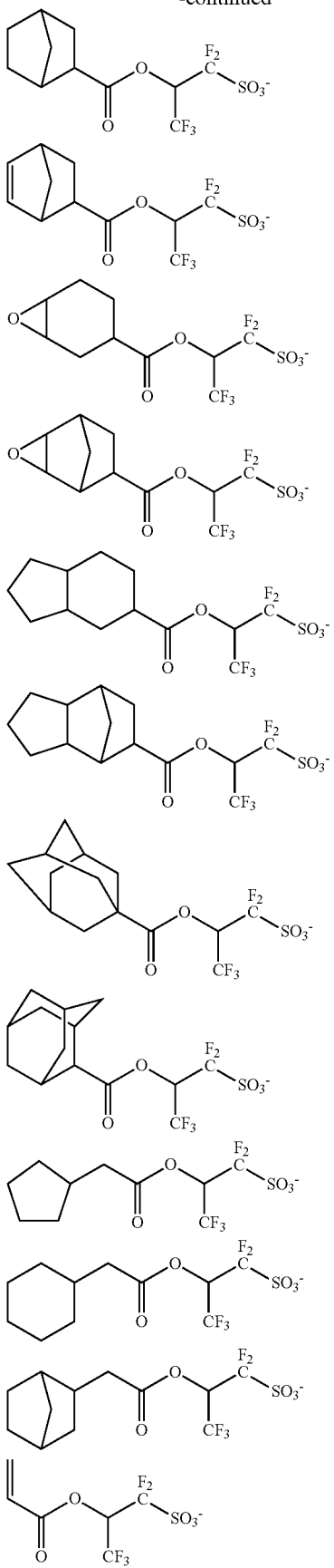
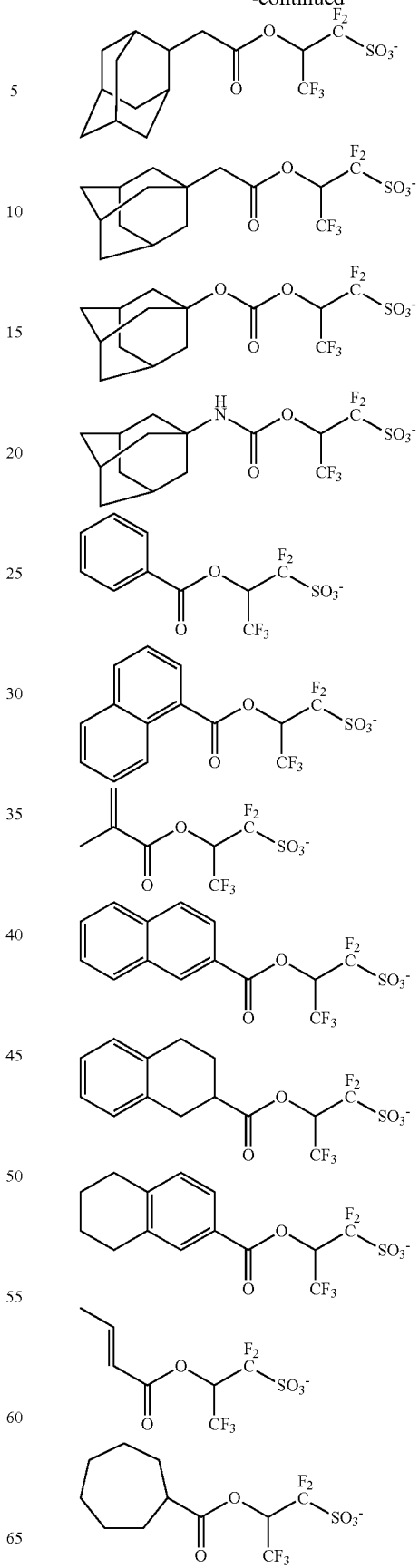

55
-continued
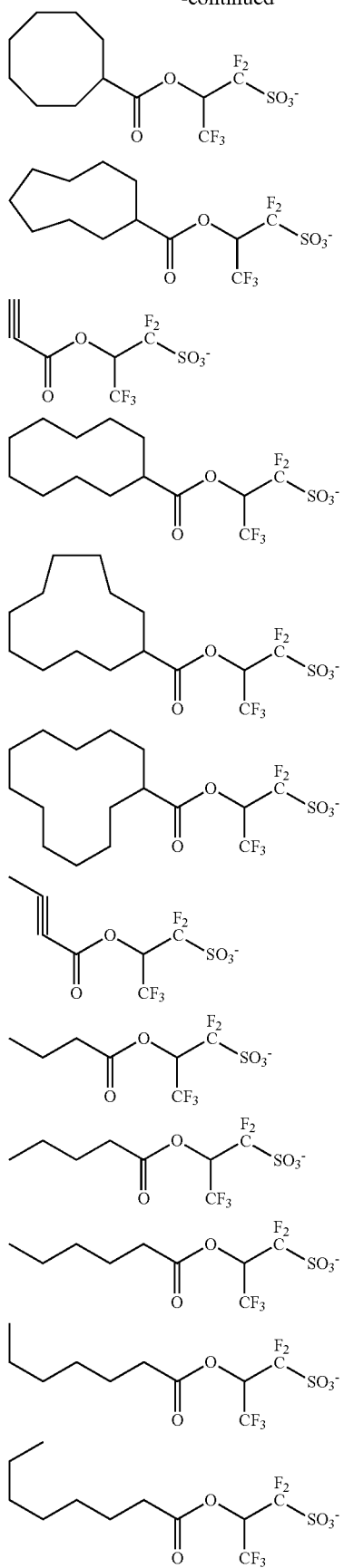
56
-continued
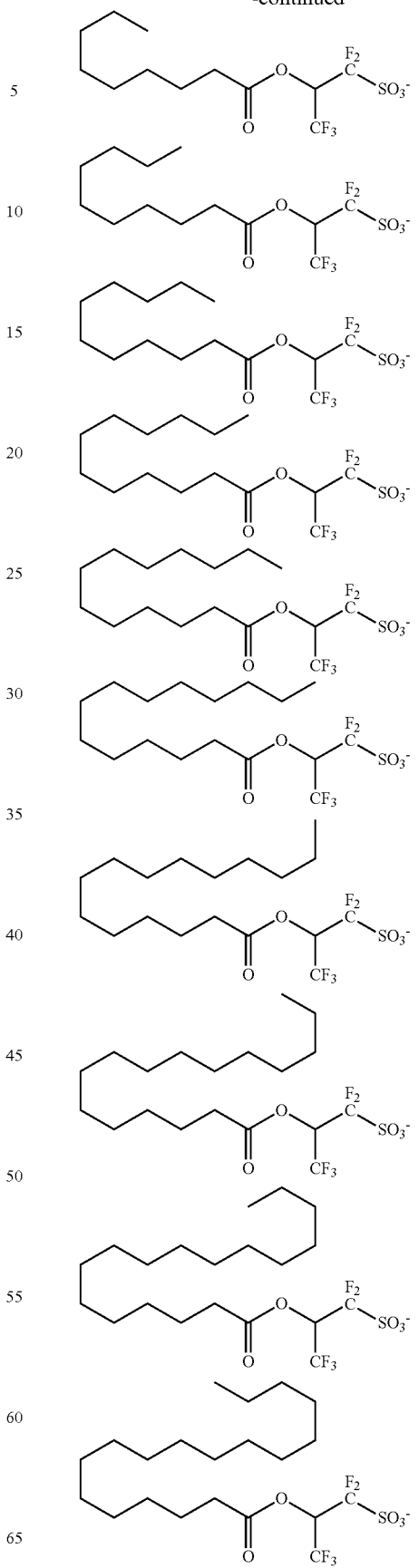

57
-continued
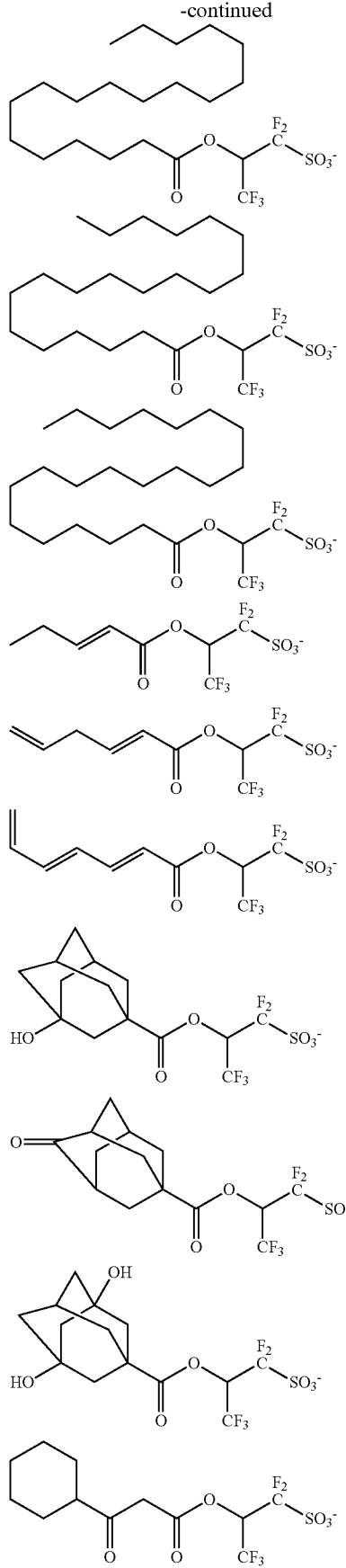
58
-continued
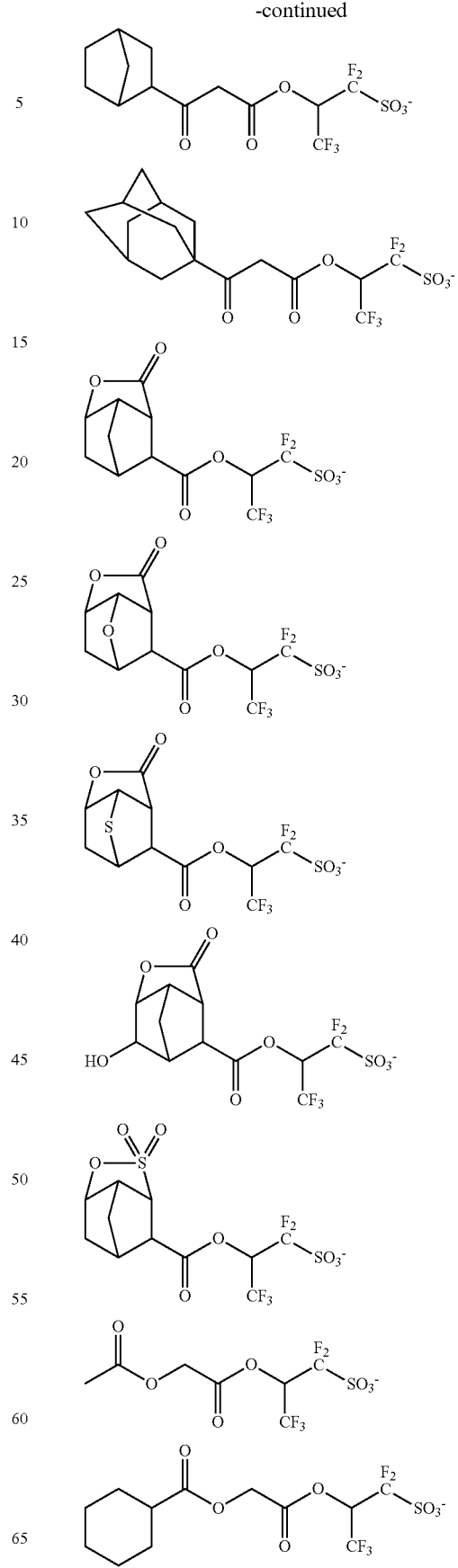

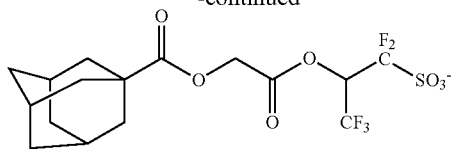
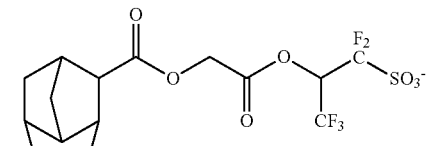
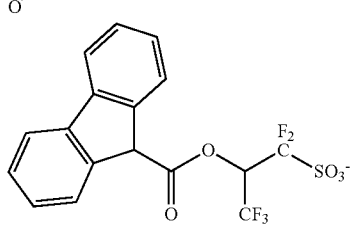
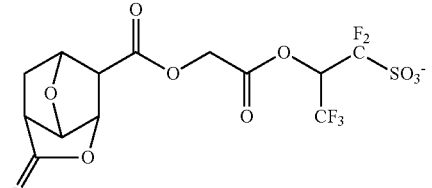
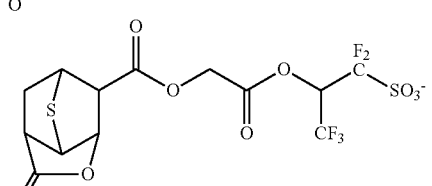
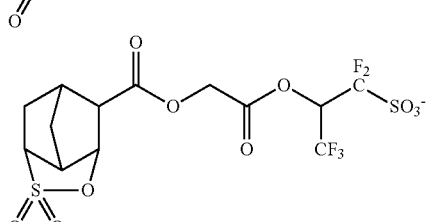
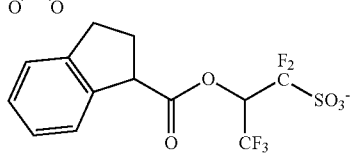
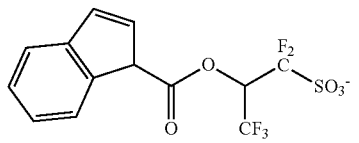
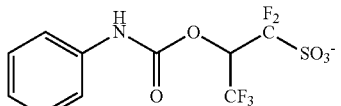
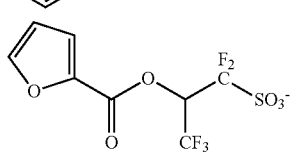
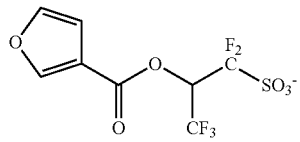
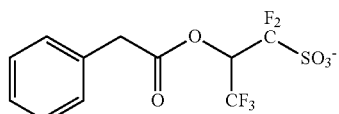
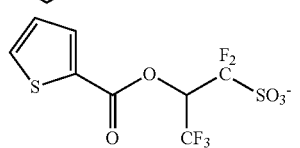
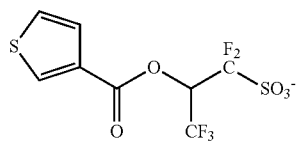
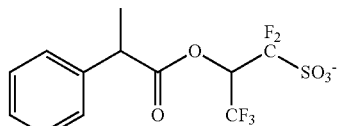
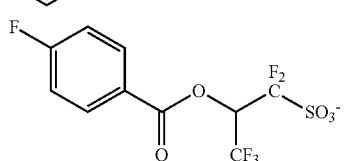
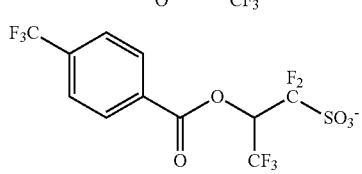
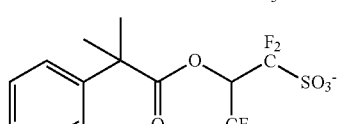
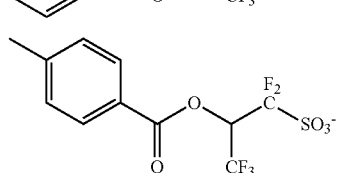
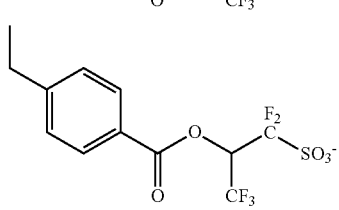
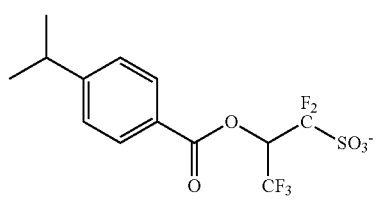

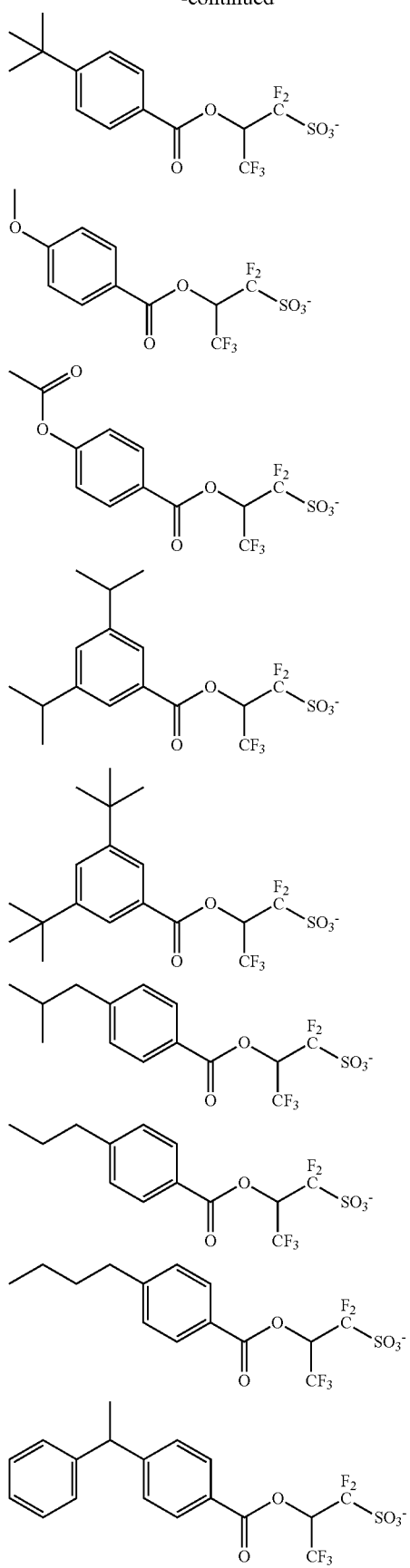
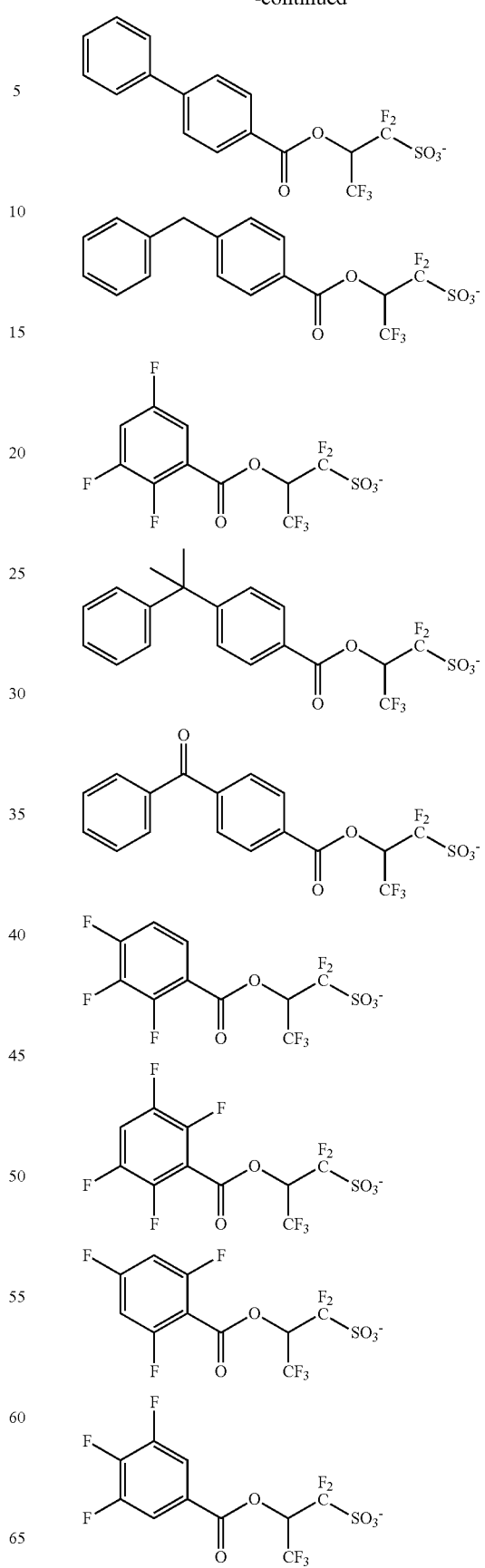

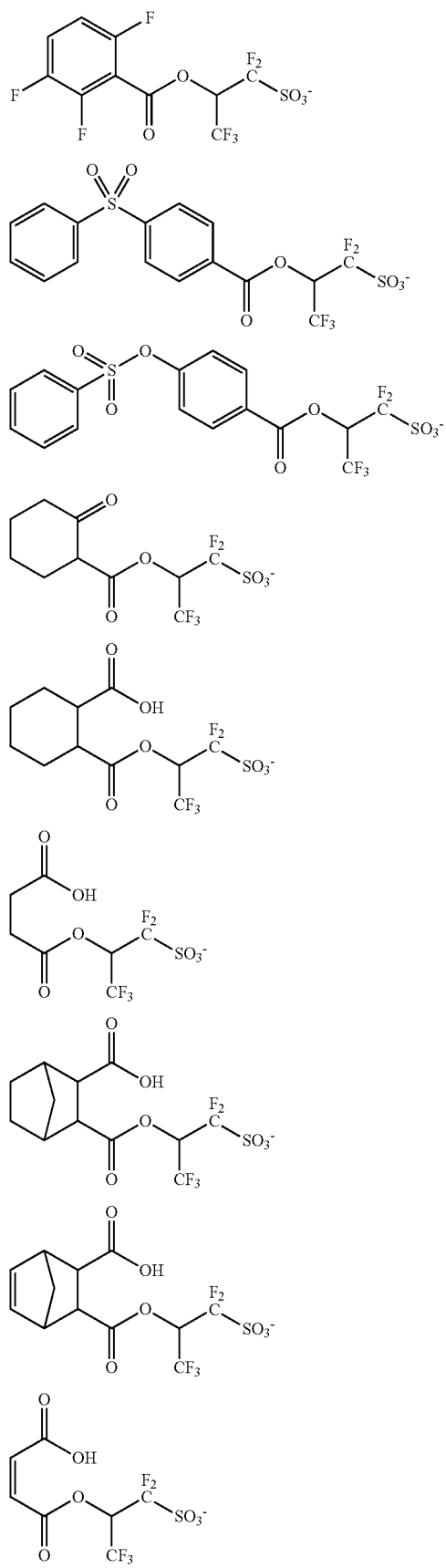
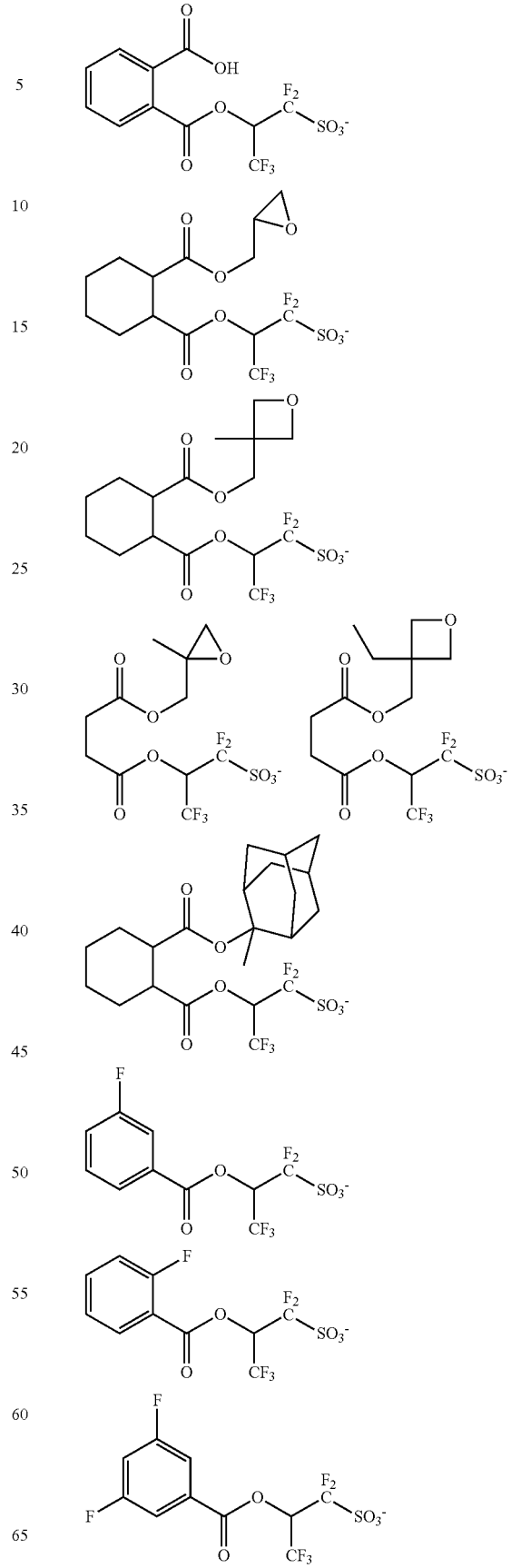

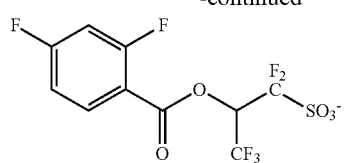
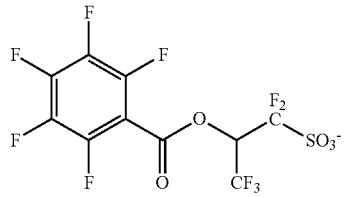
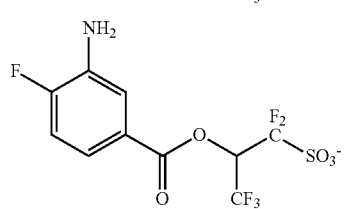
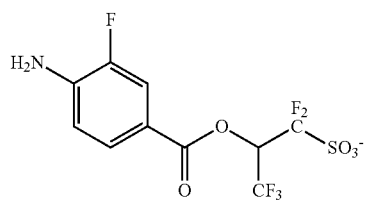
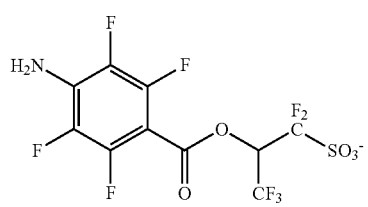
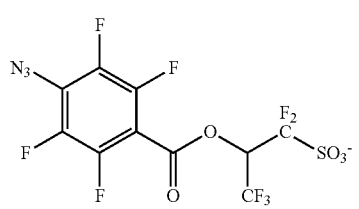
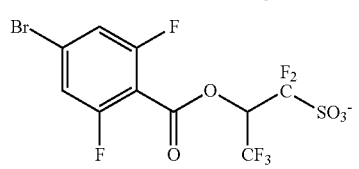
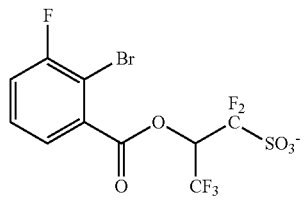
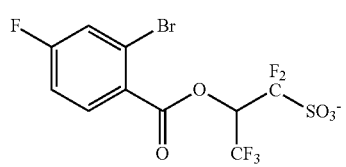
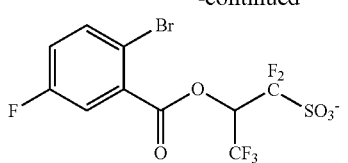
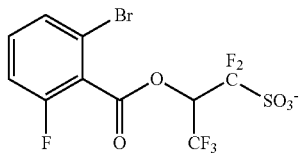
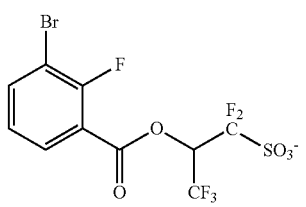
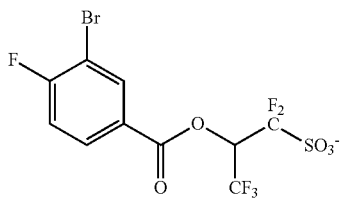
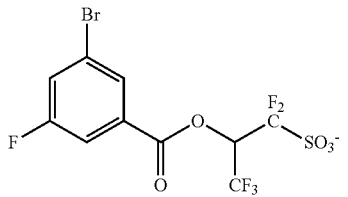
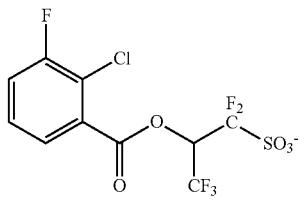
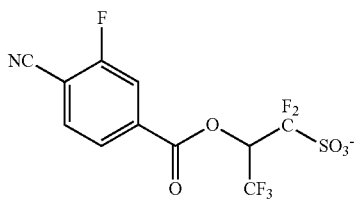
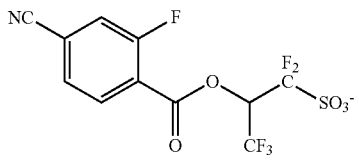
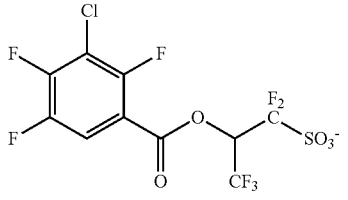

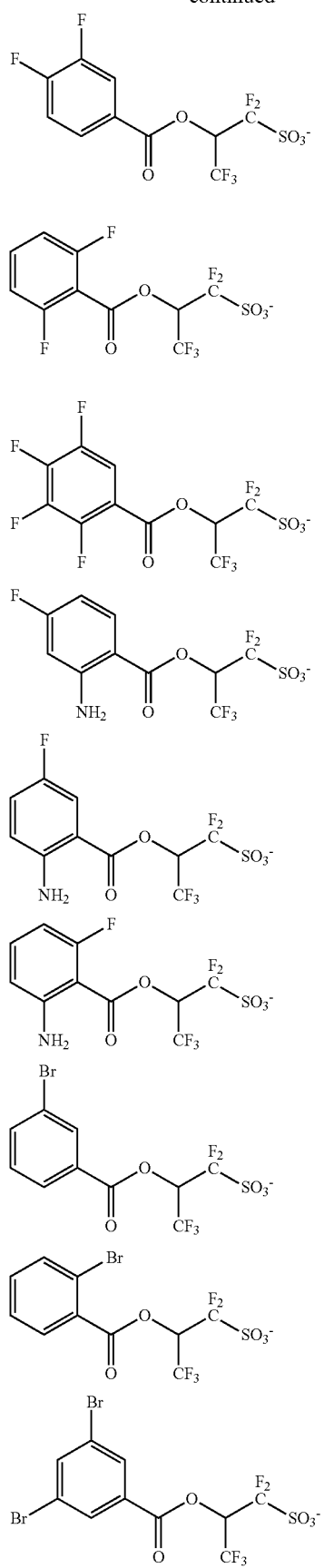
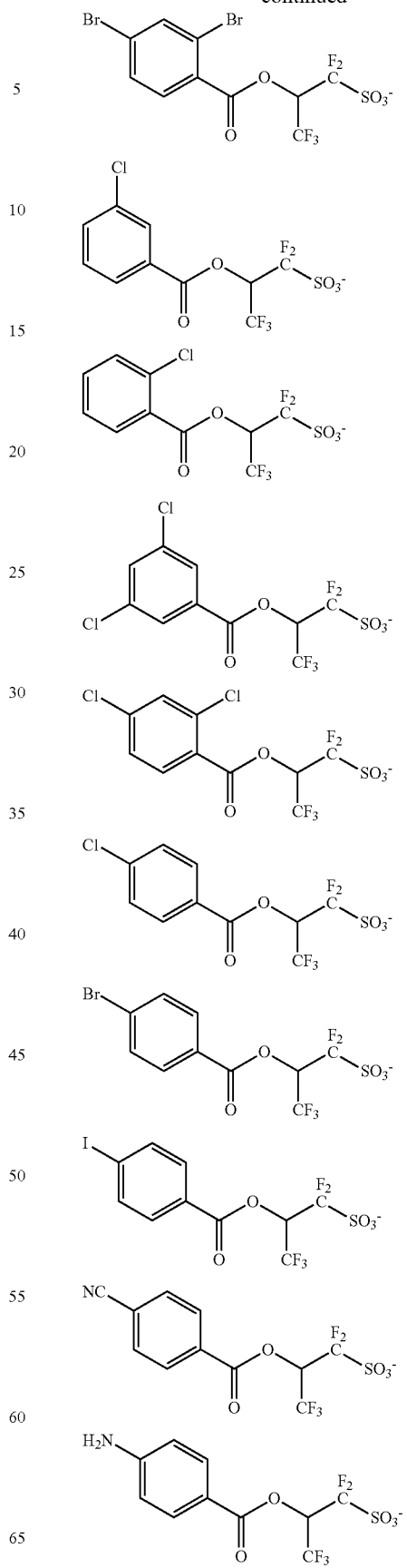

-continued
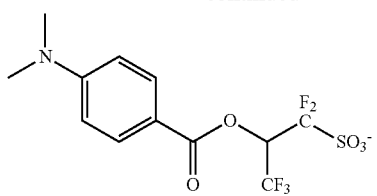
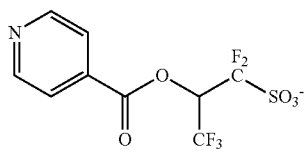
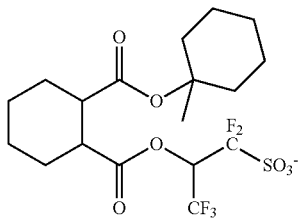
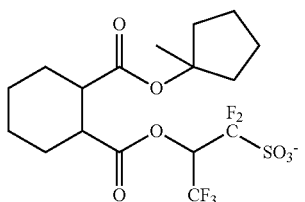
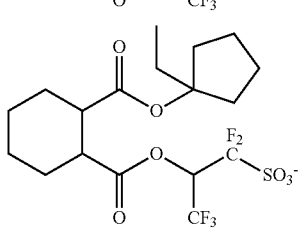
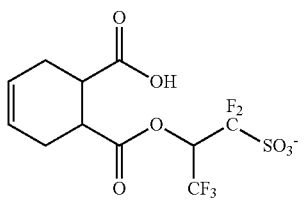
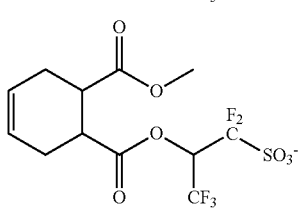
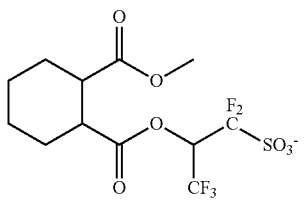
-continued
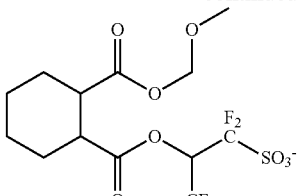
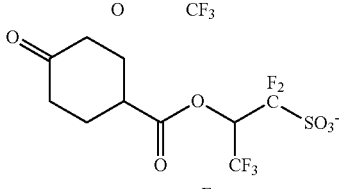
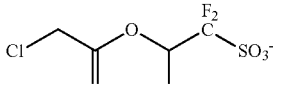
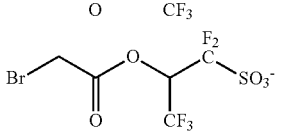
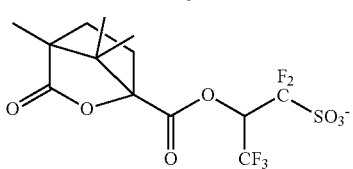
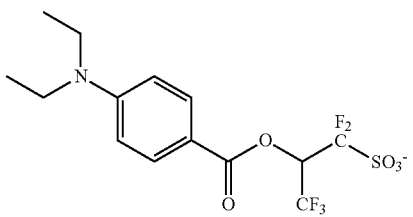
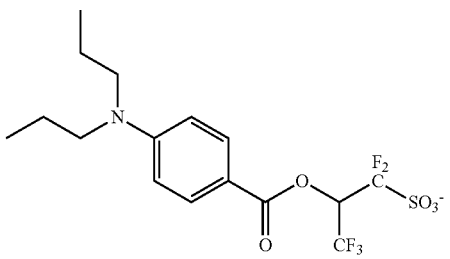
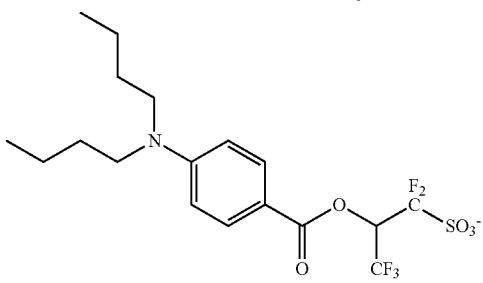
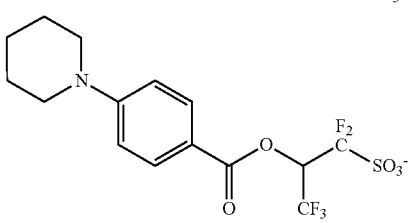

71
-continued
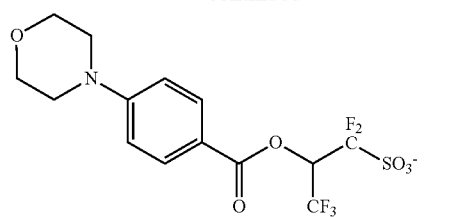
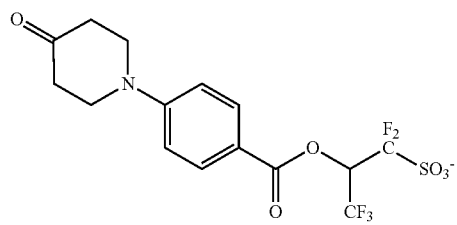
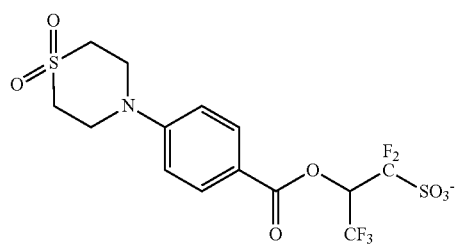
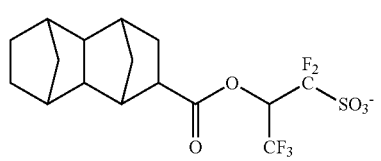
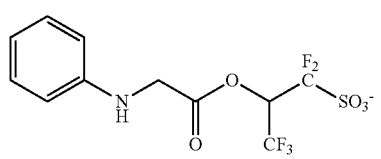
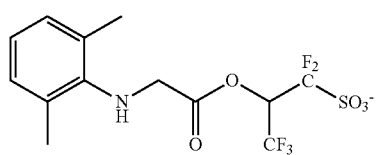
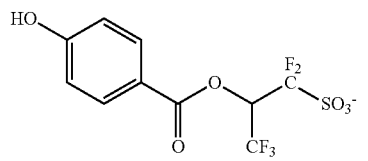
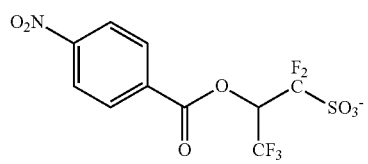
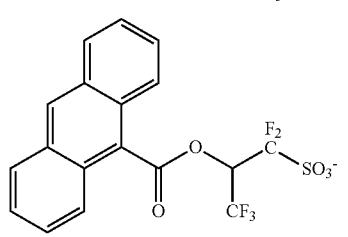
72
-continued
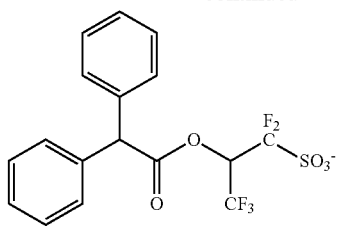
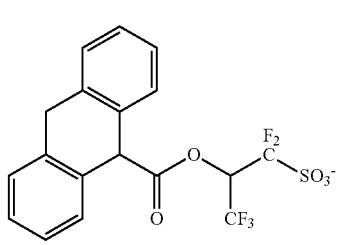
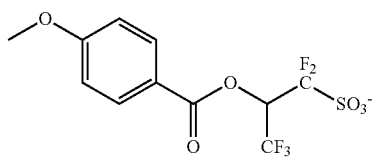
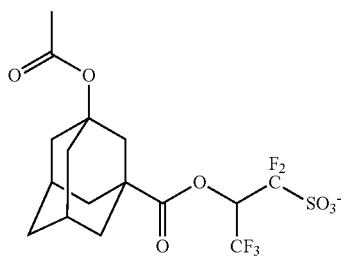
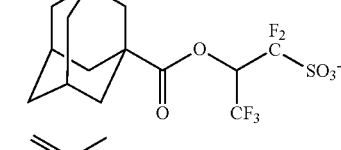
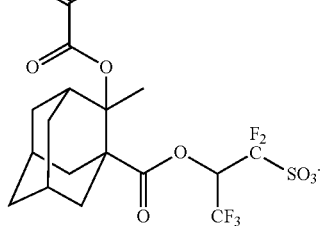
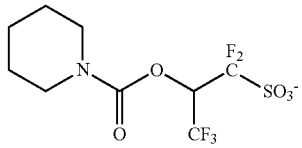

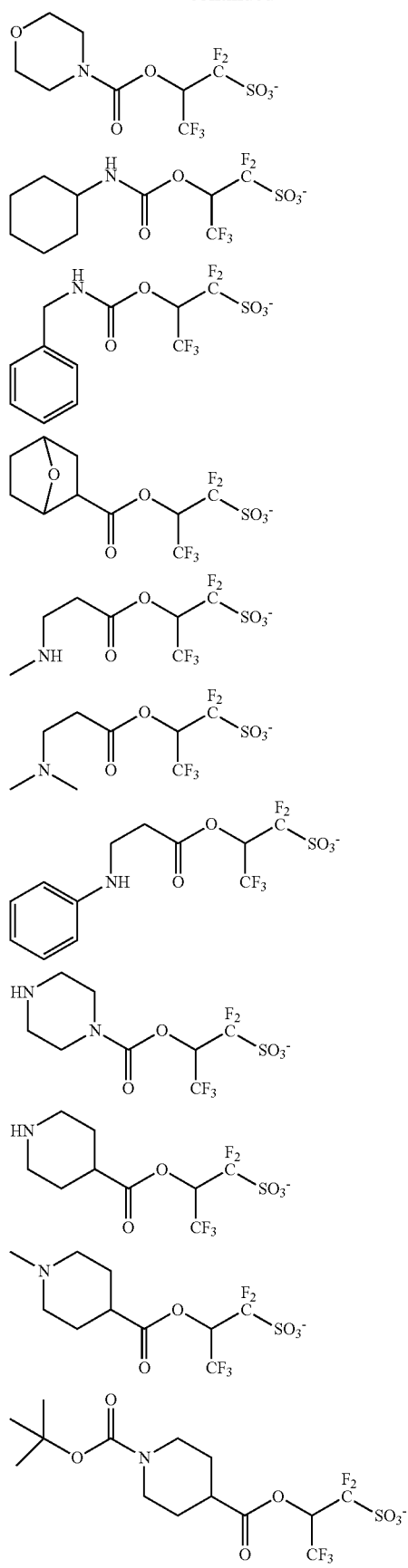
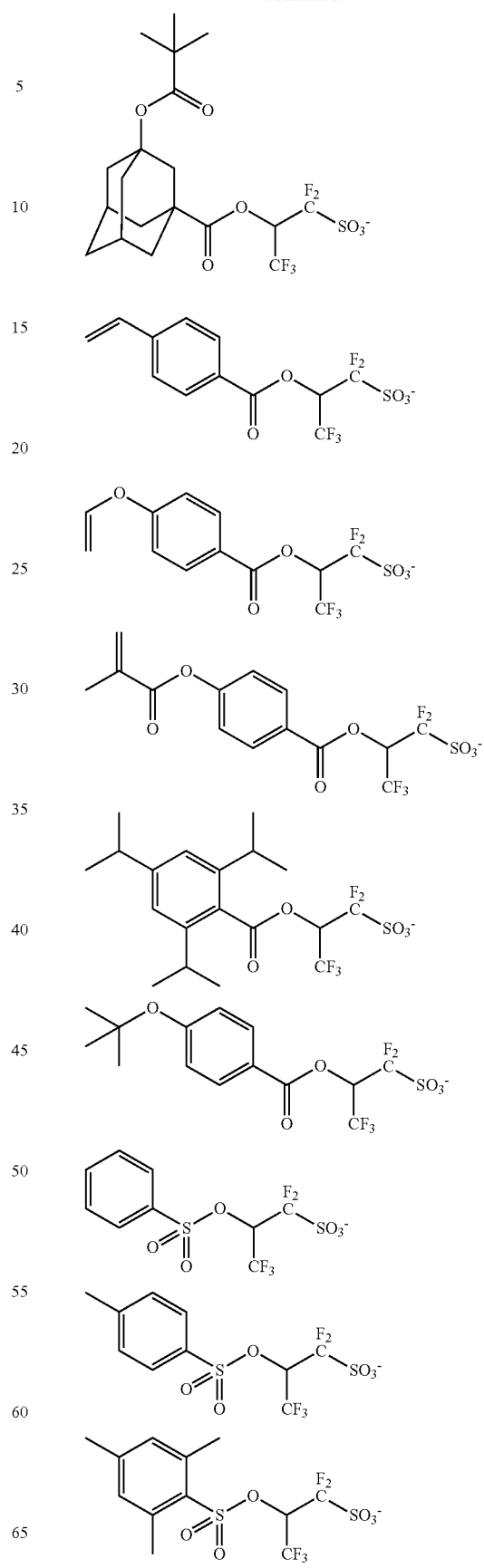

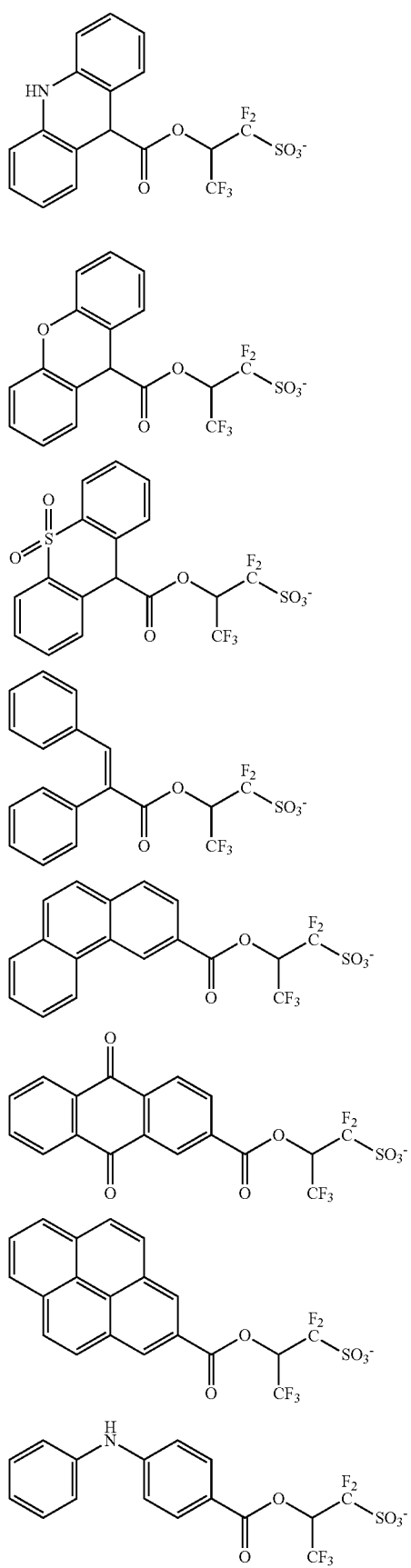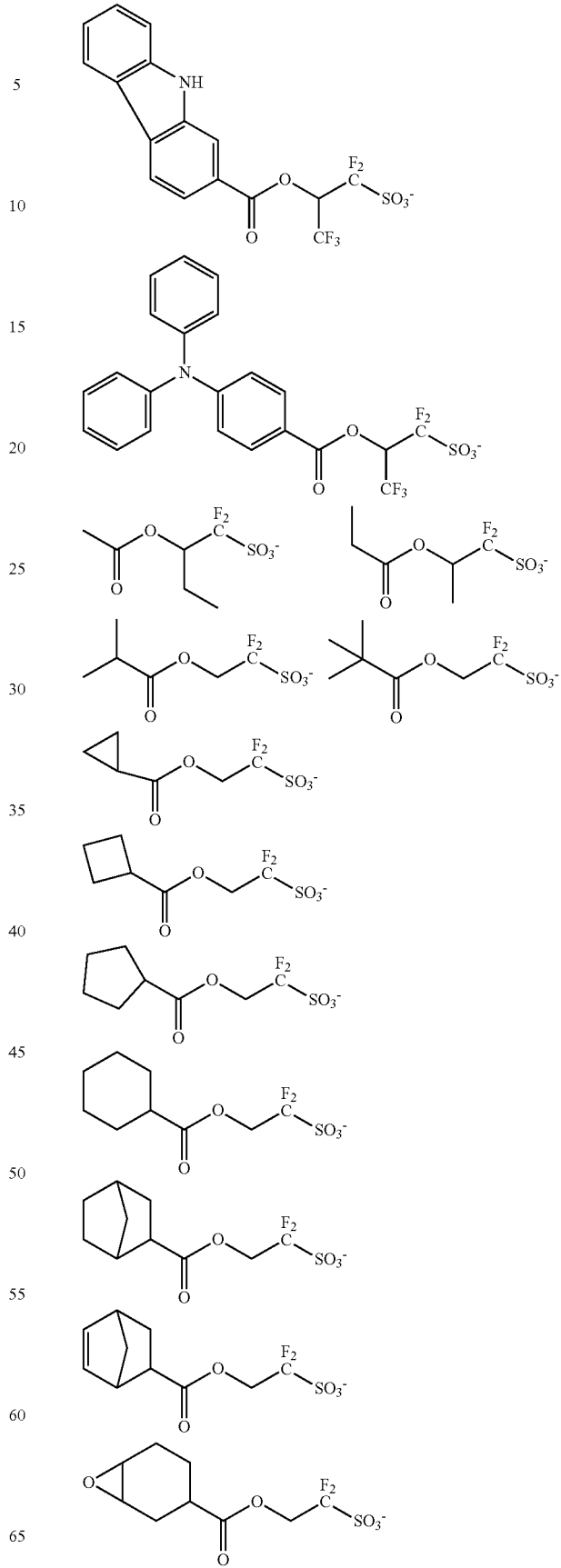

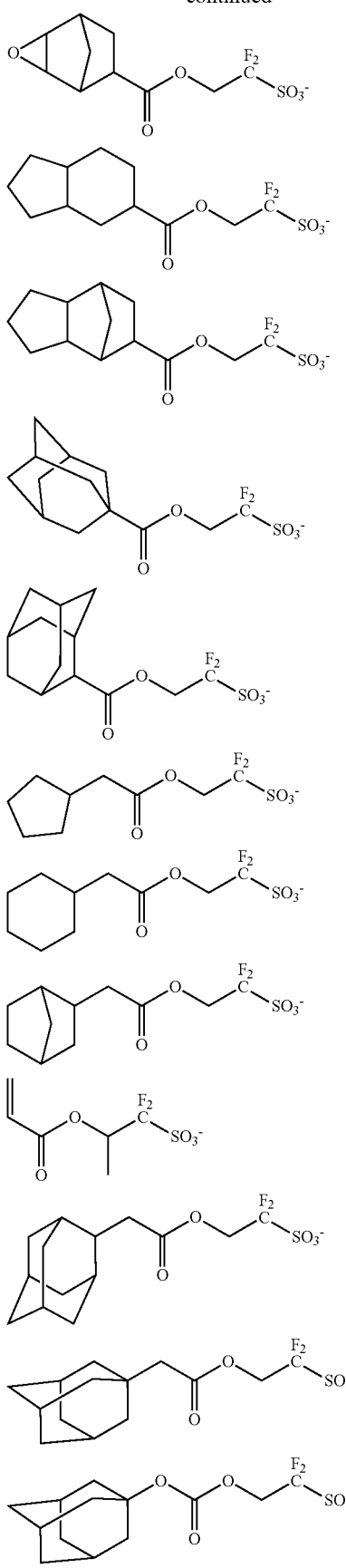
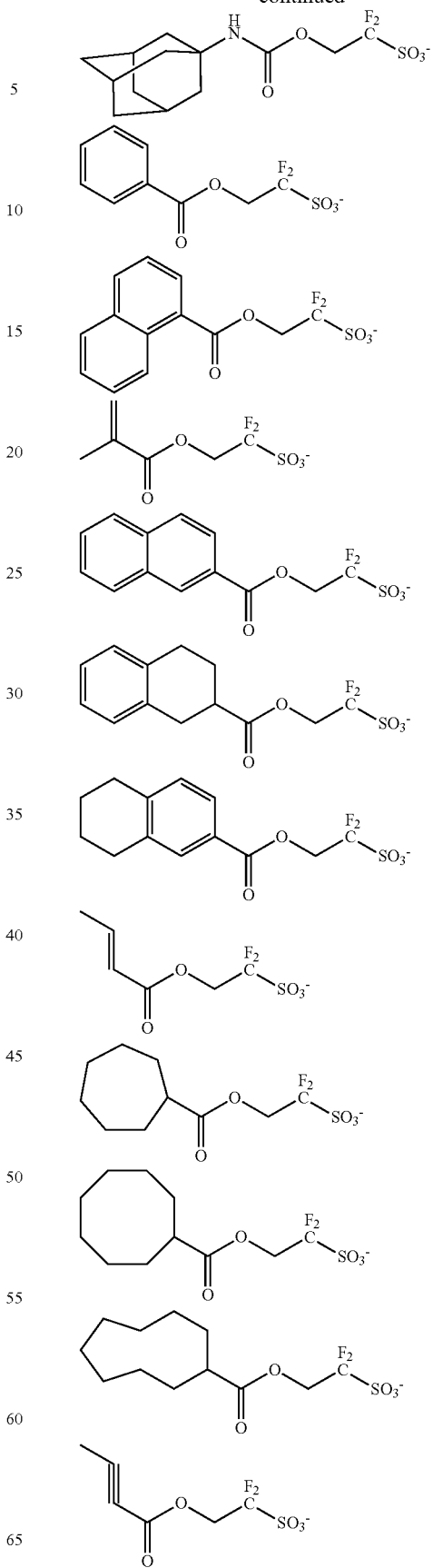

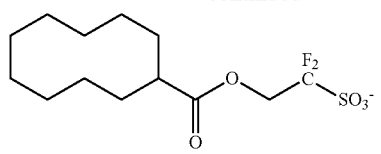
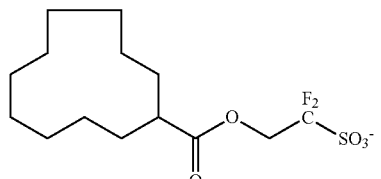
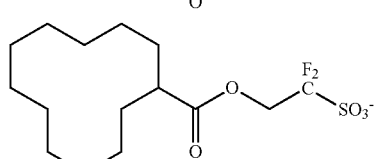
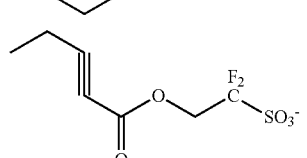
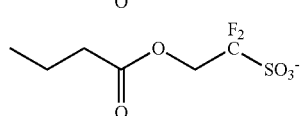
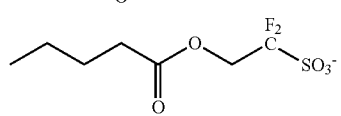
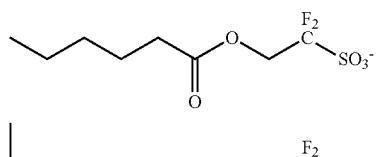
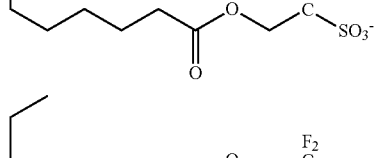
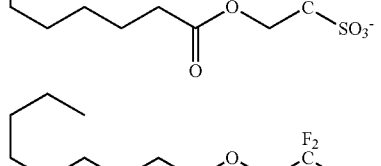
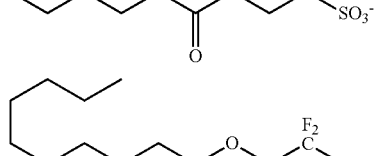
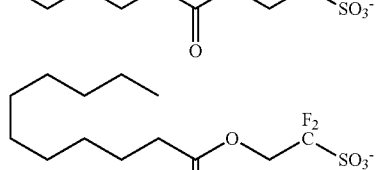
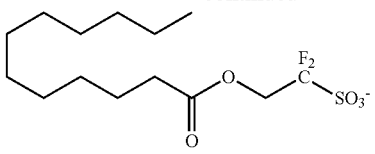
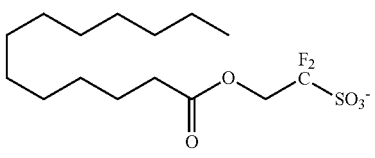
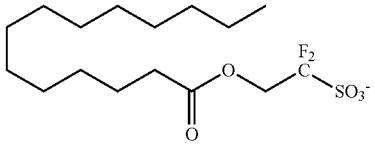
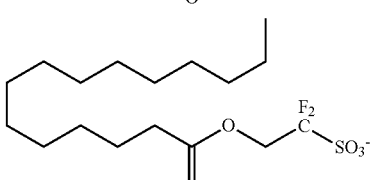
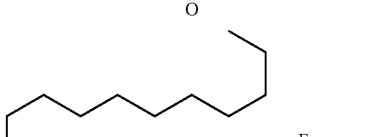
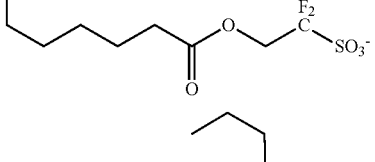
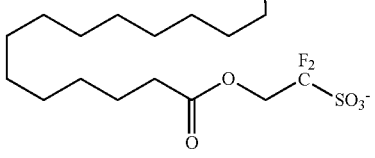
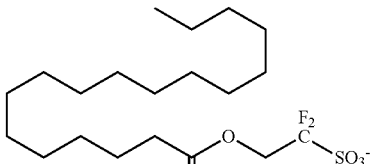
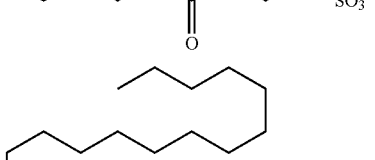
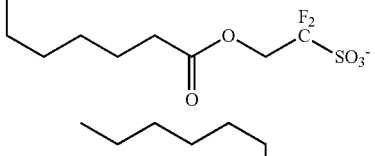
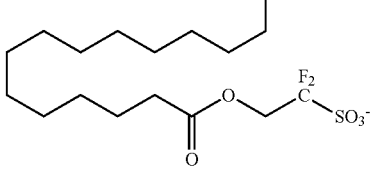

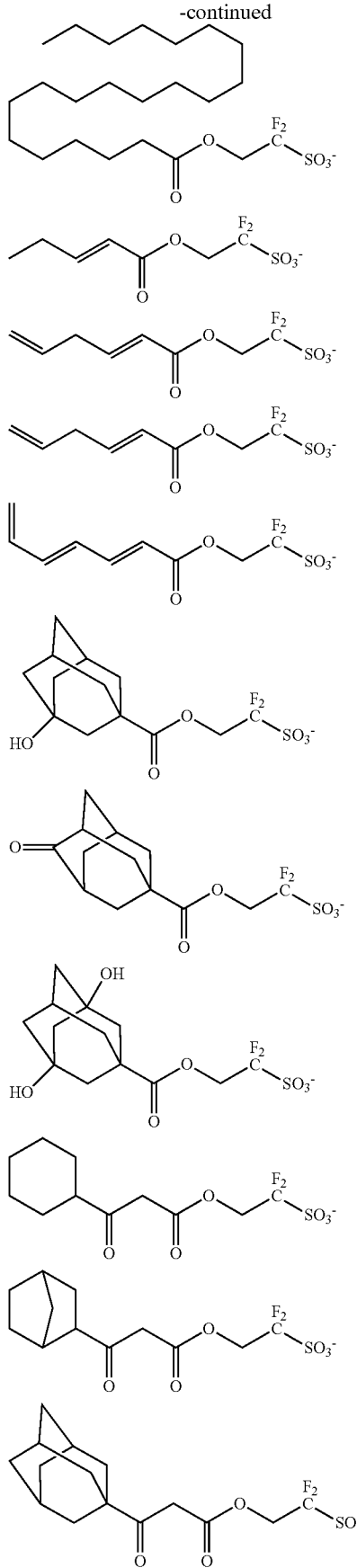
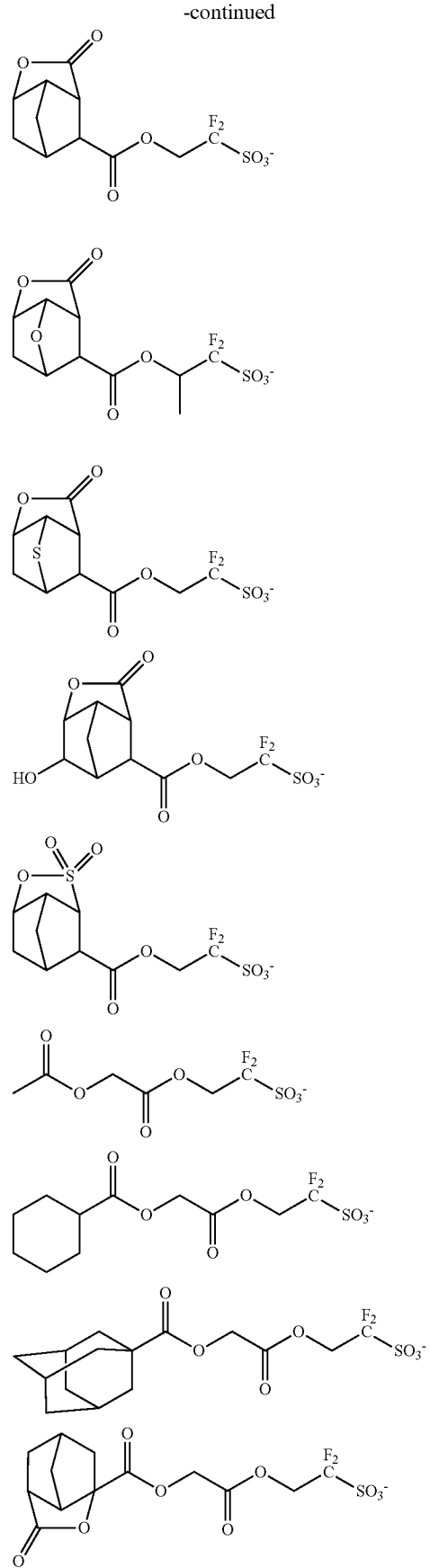

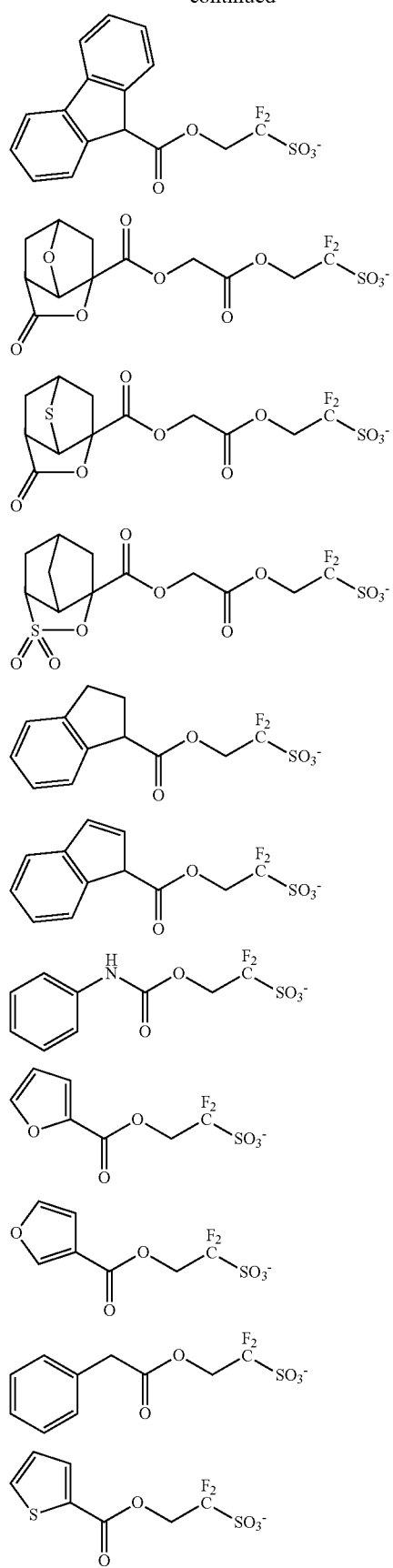
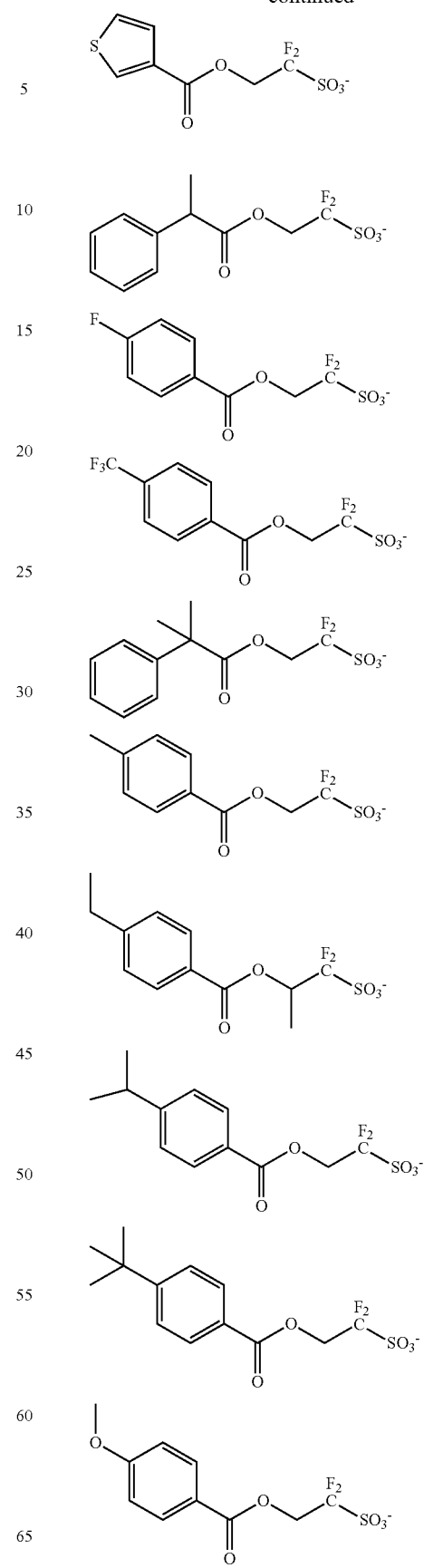

85
-continued
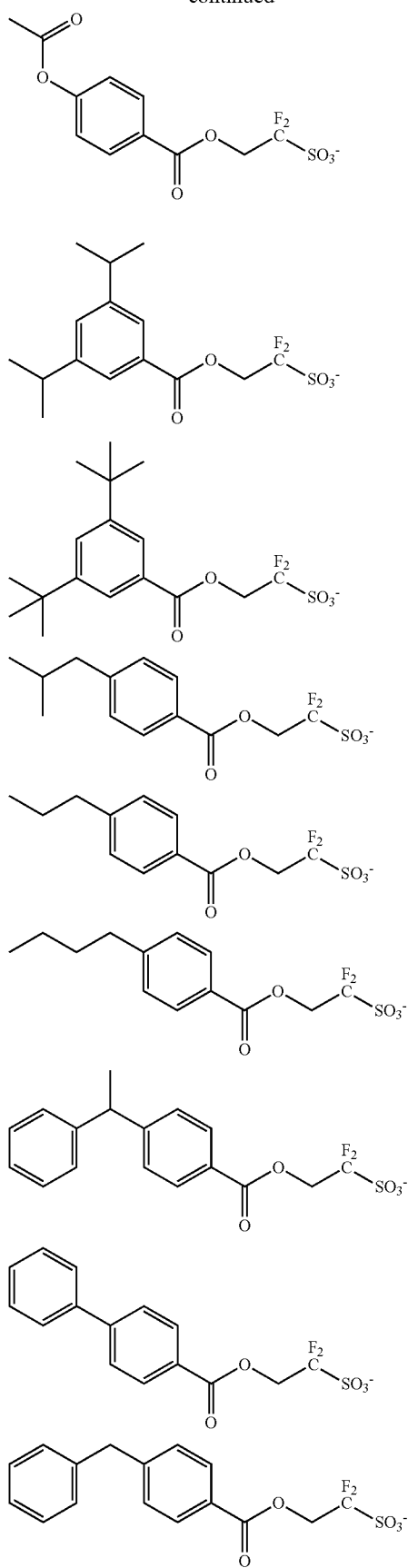
86
-continued
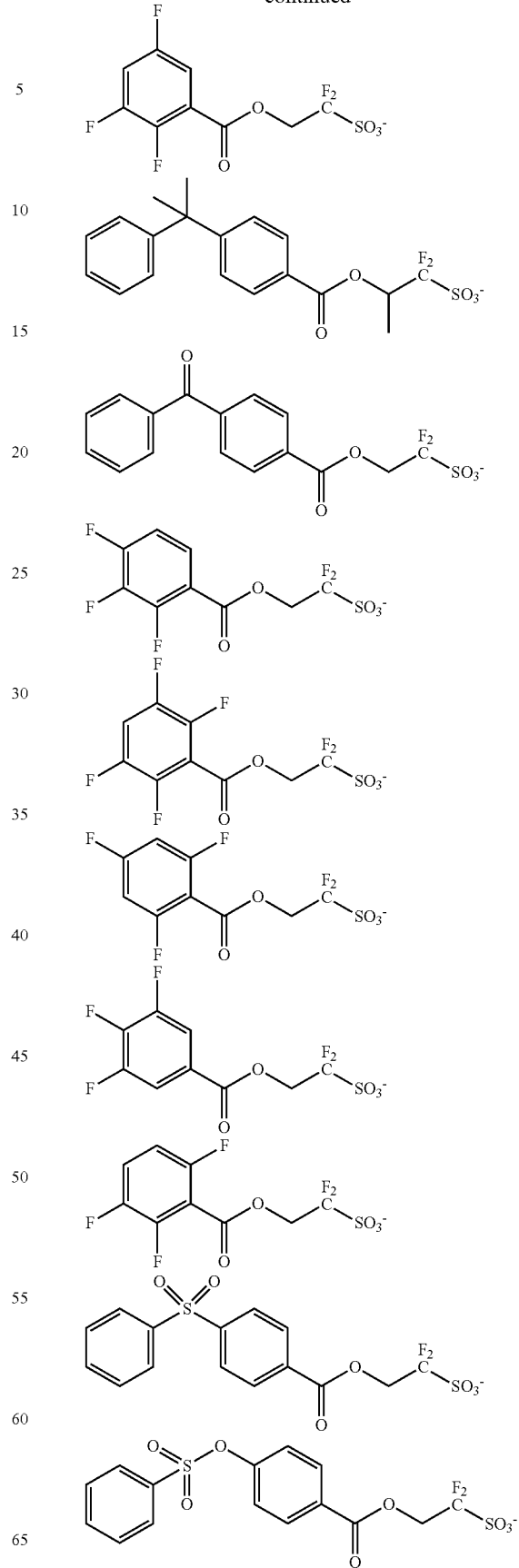

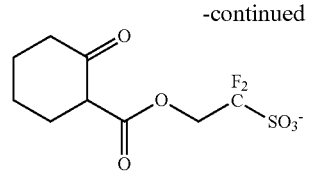
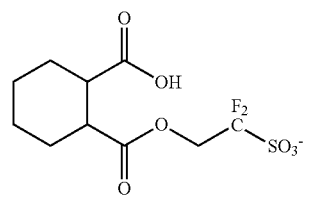
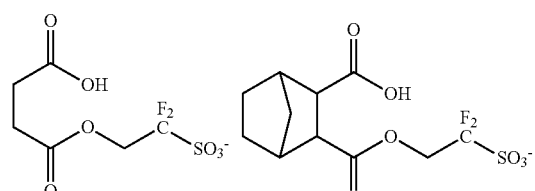
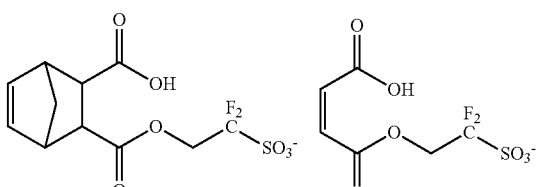
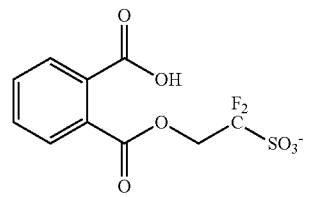
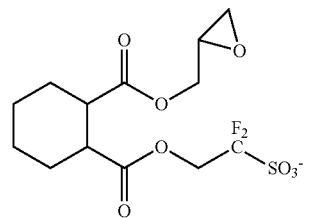
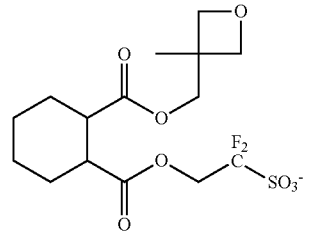
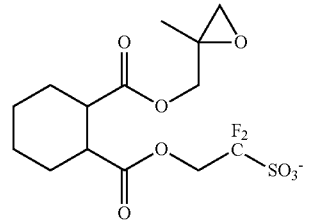
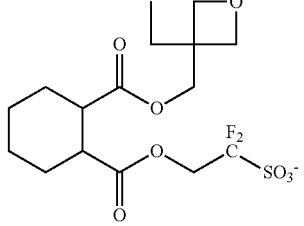
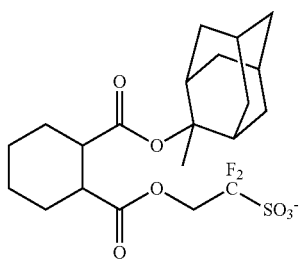
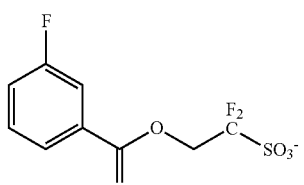
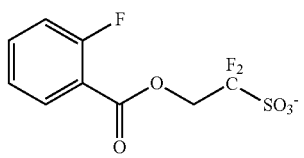
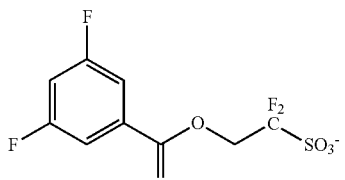
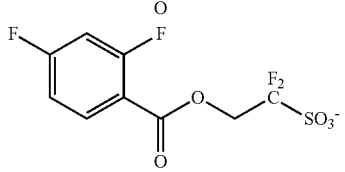
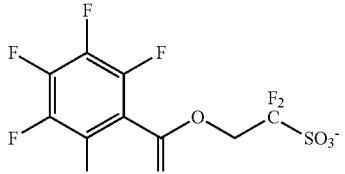
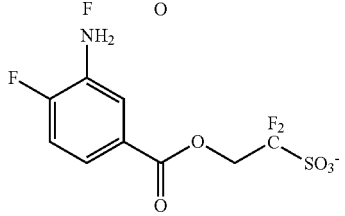

-continued
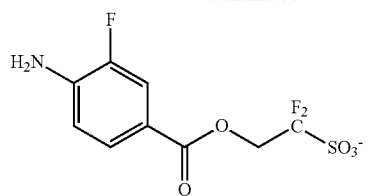
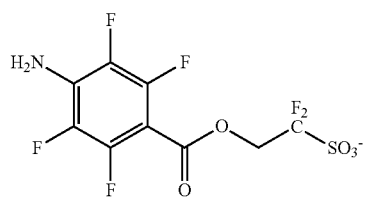
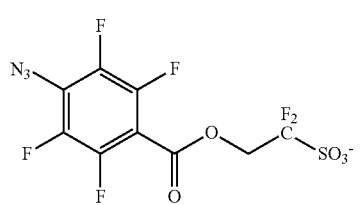
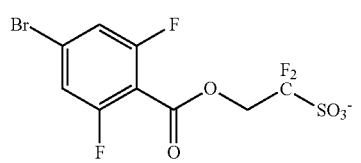
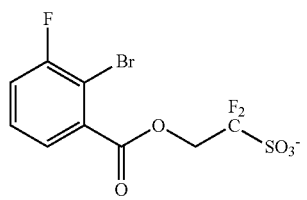
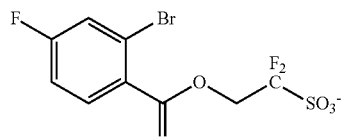
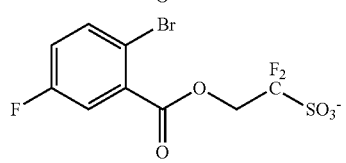
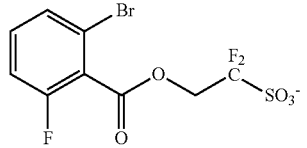
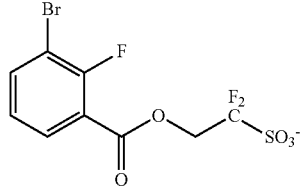
-continued
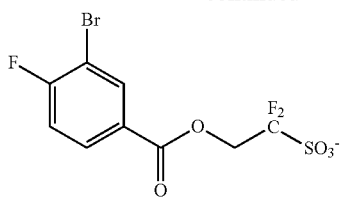
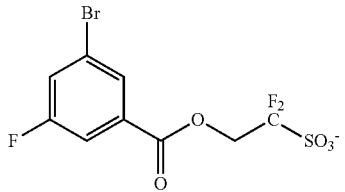
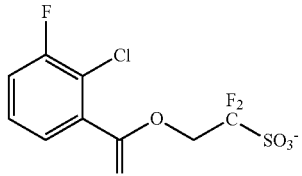
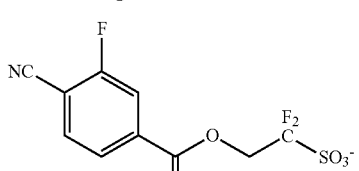
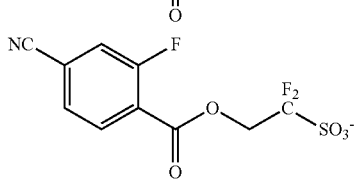
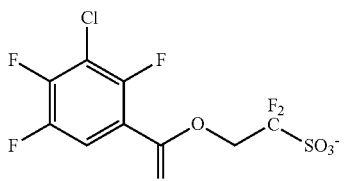
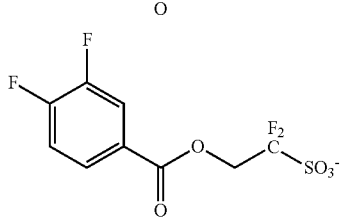
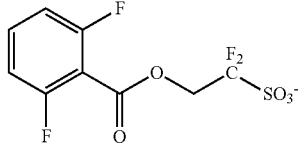
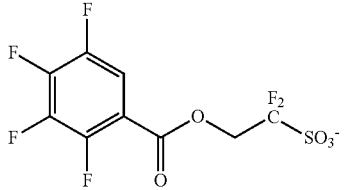

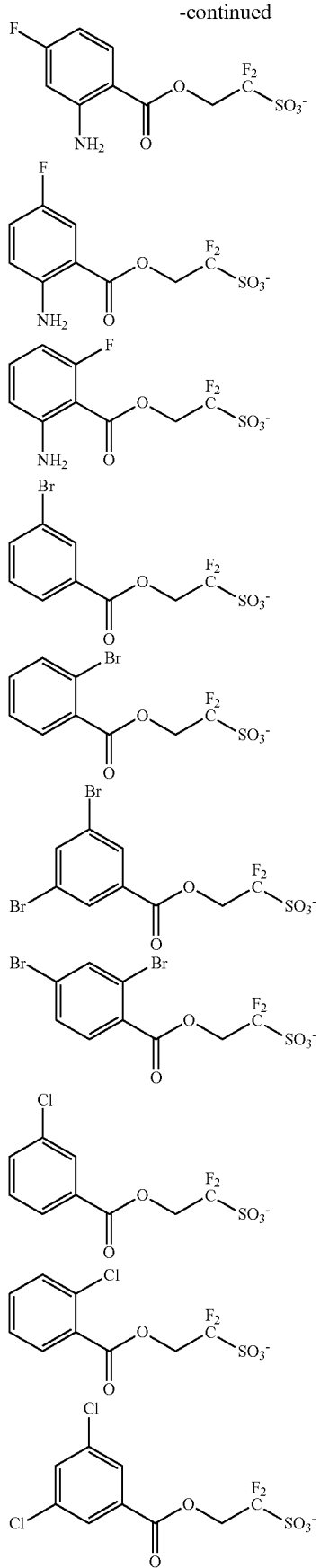
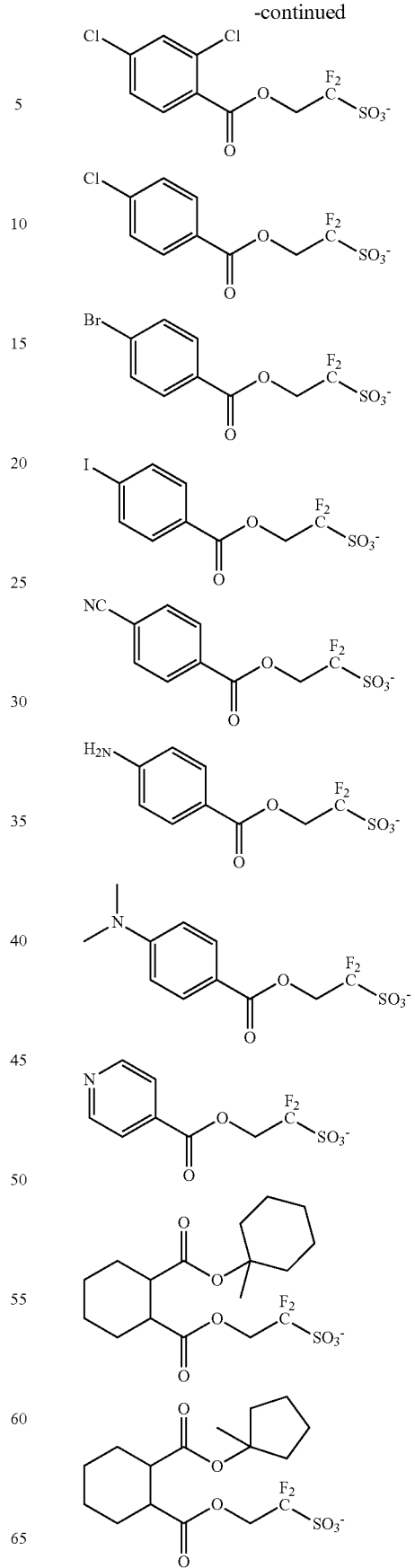

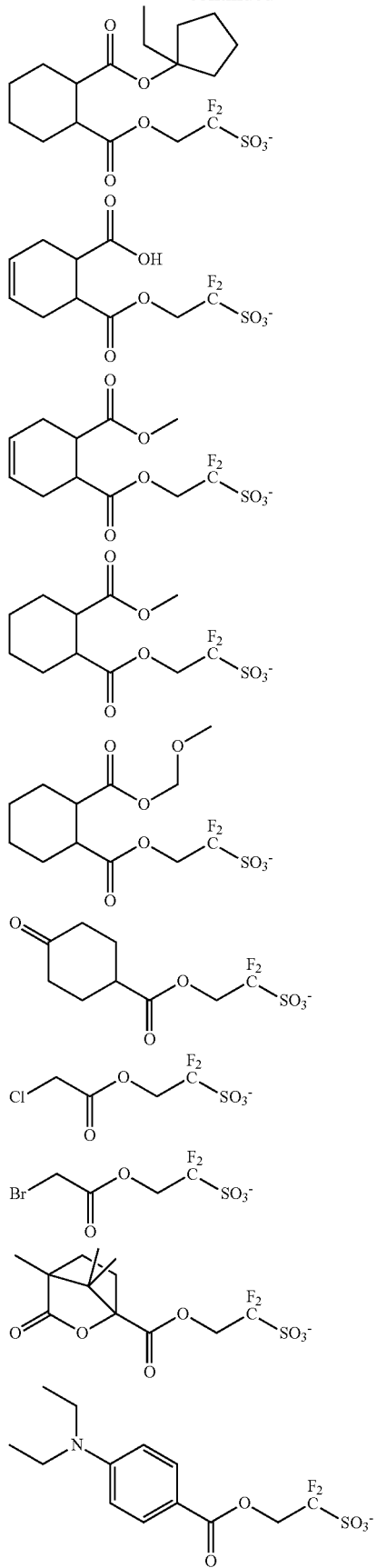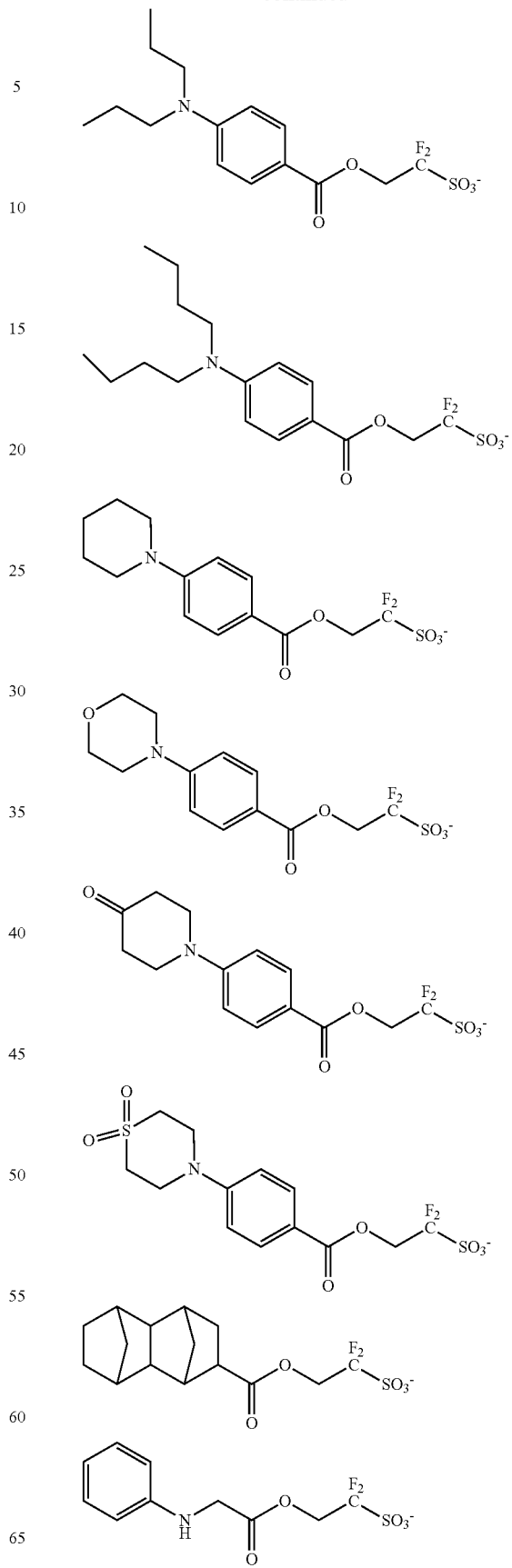

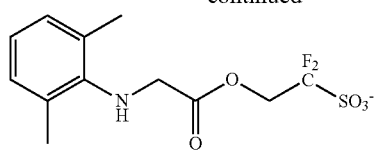
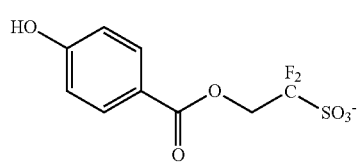
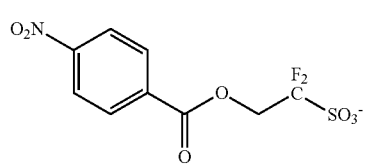
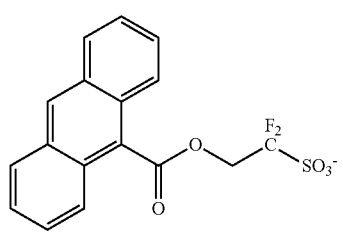
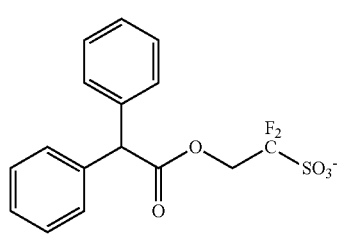
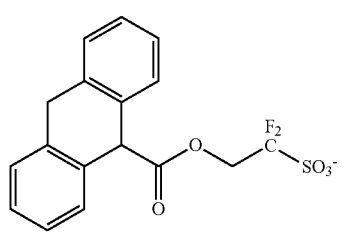
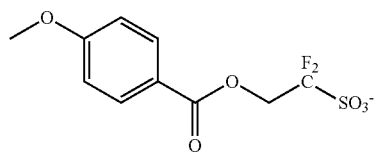
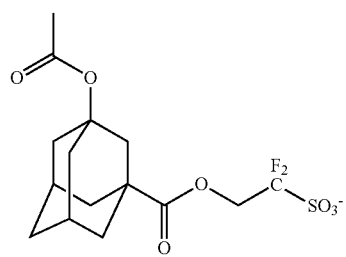
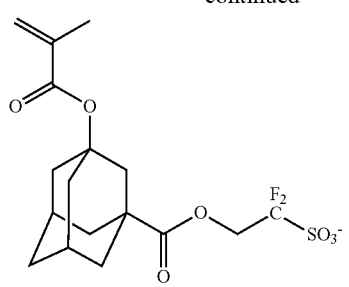
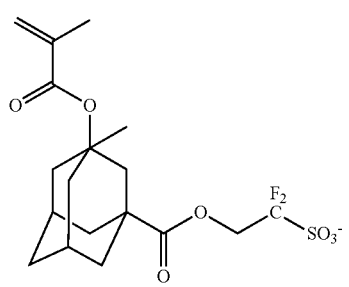
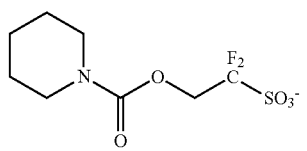
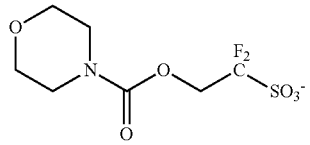
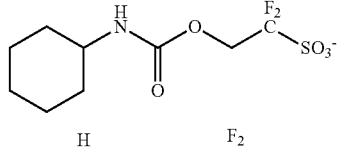
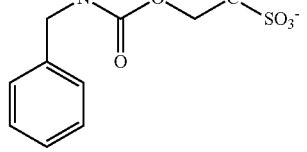
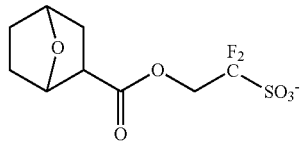
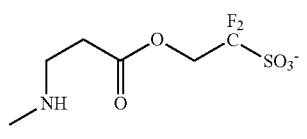
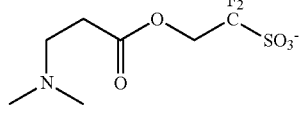

-continued

-continued

101
-continued
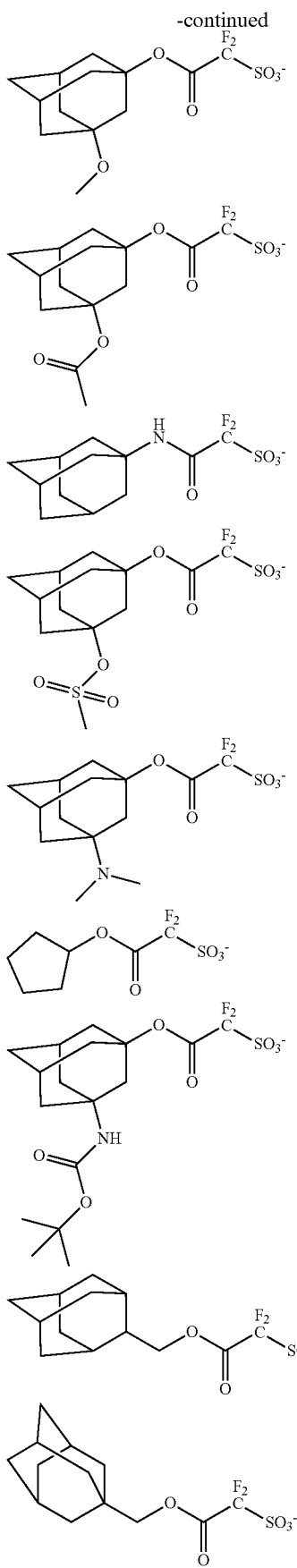
102
-continued
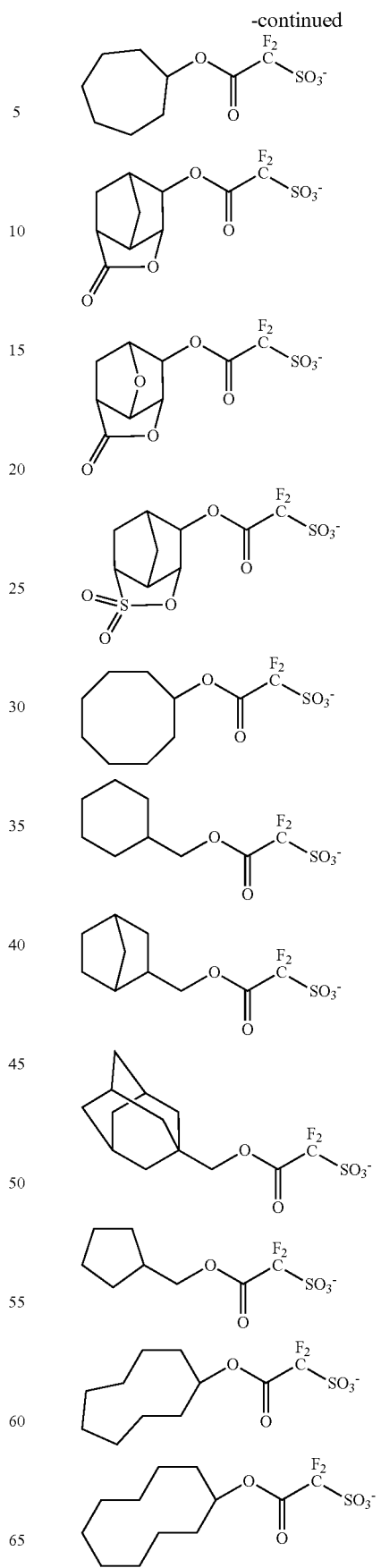

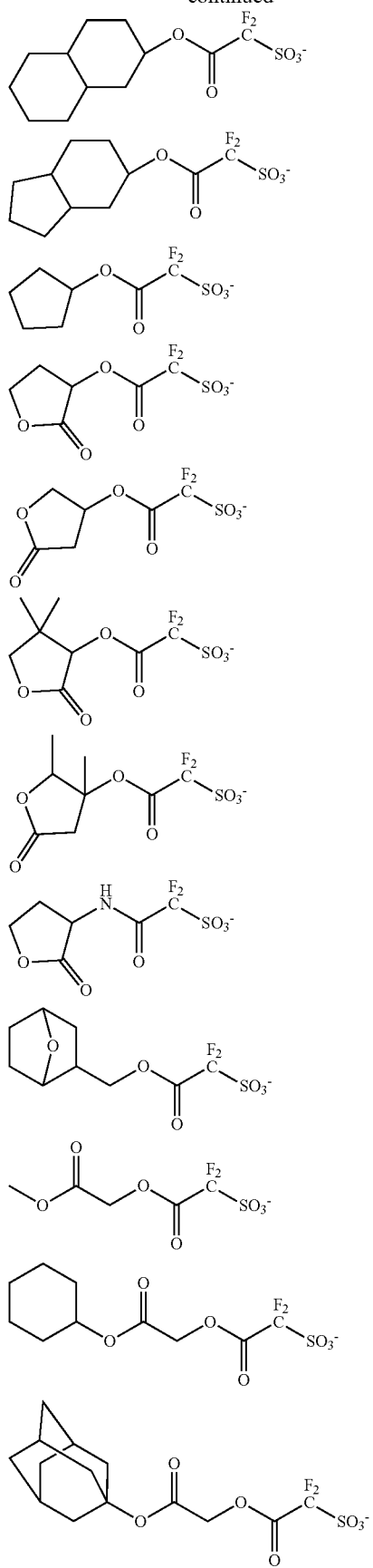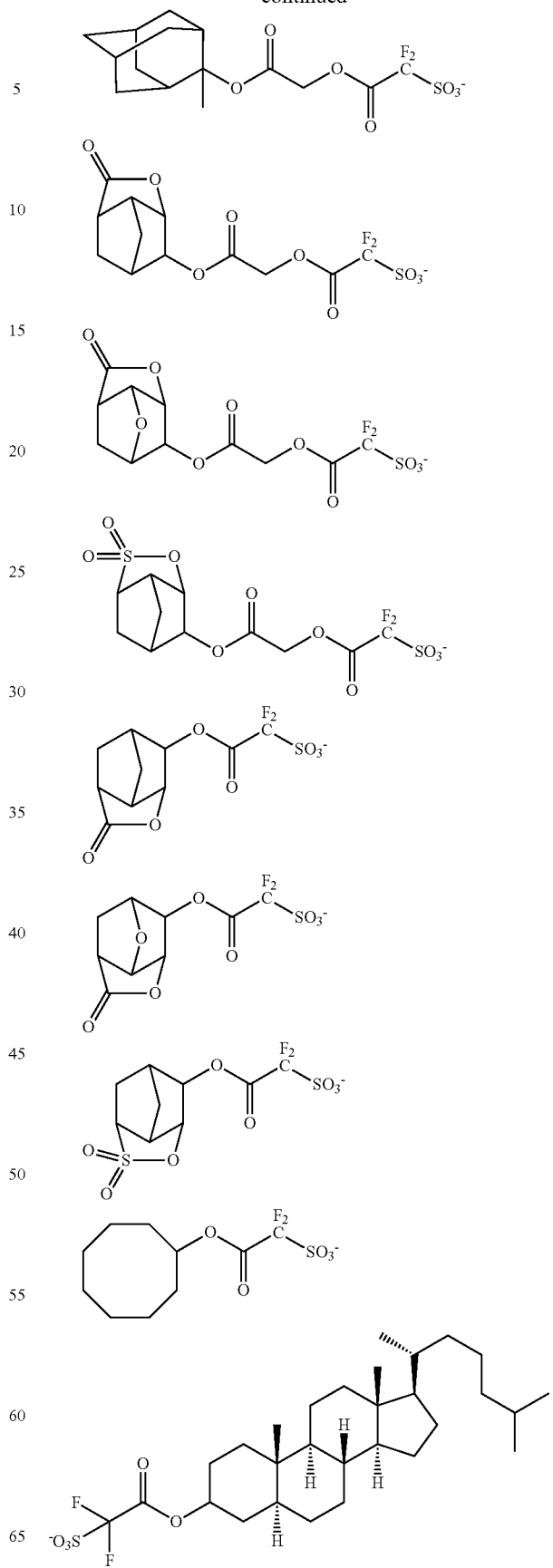

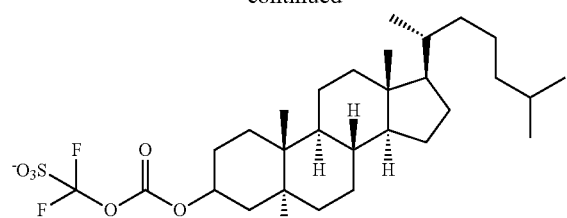
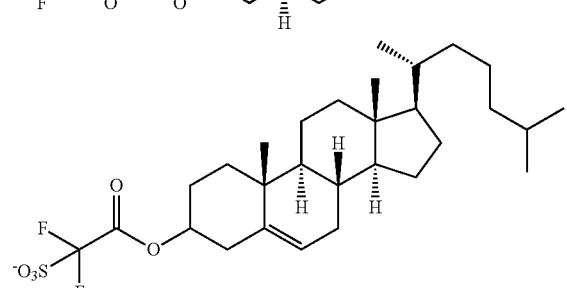
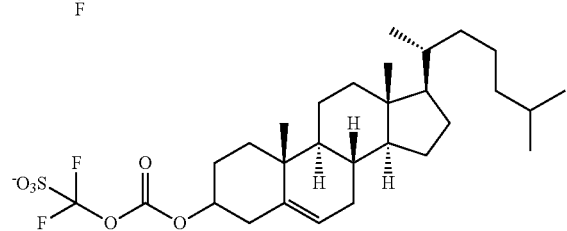
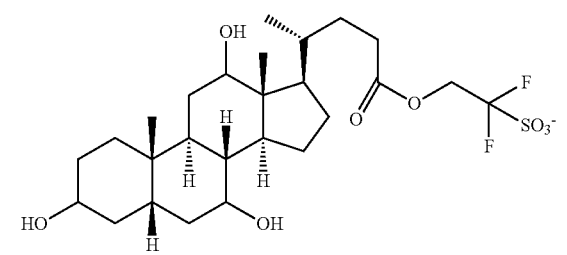
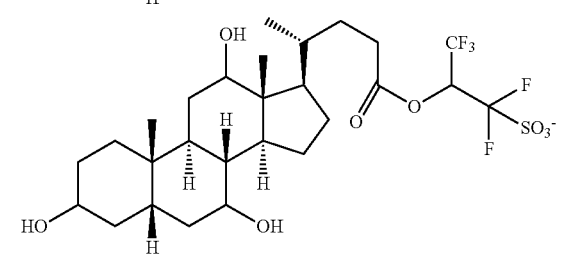
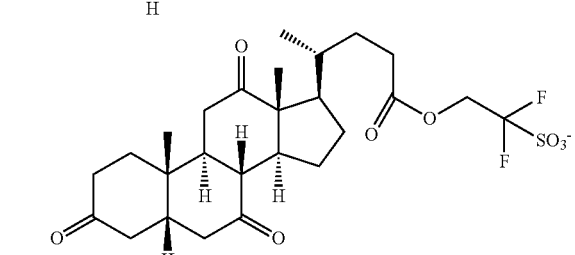
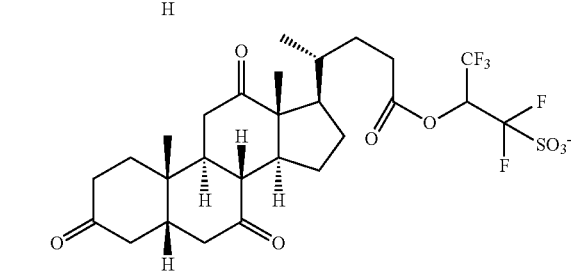
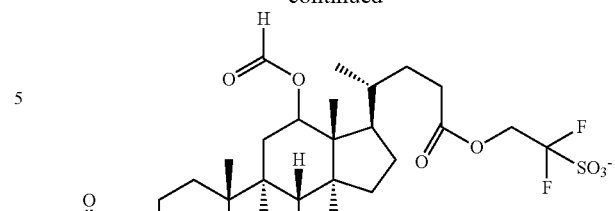
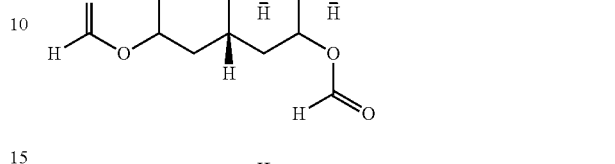
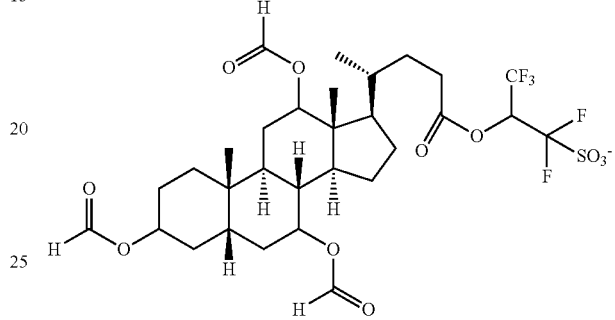
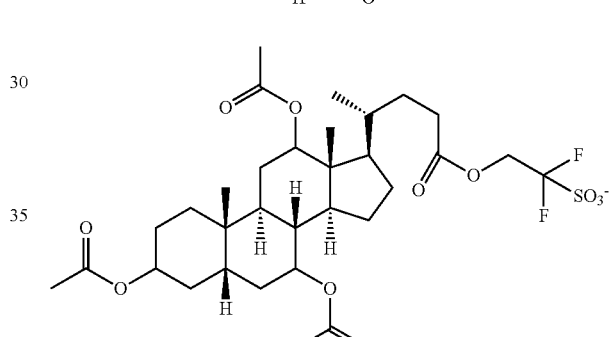
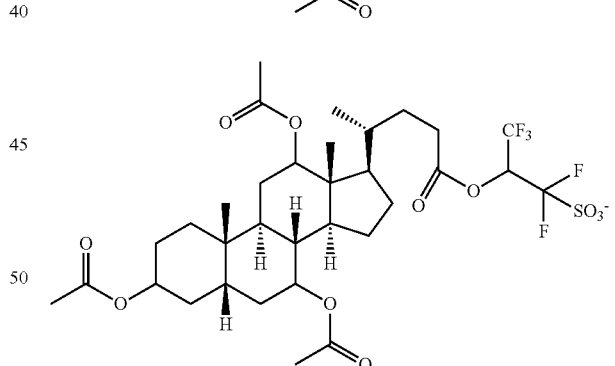
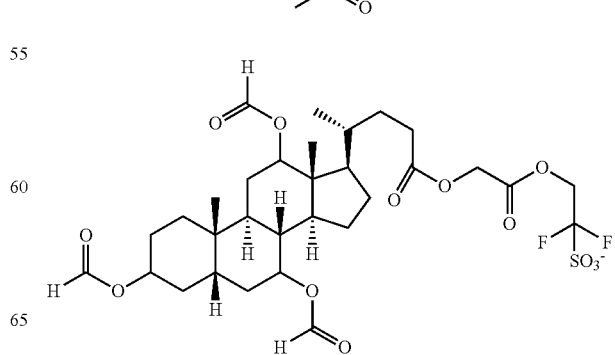

107
-continued
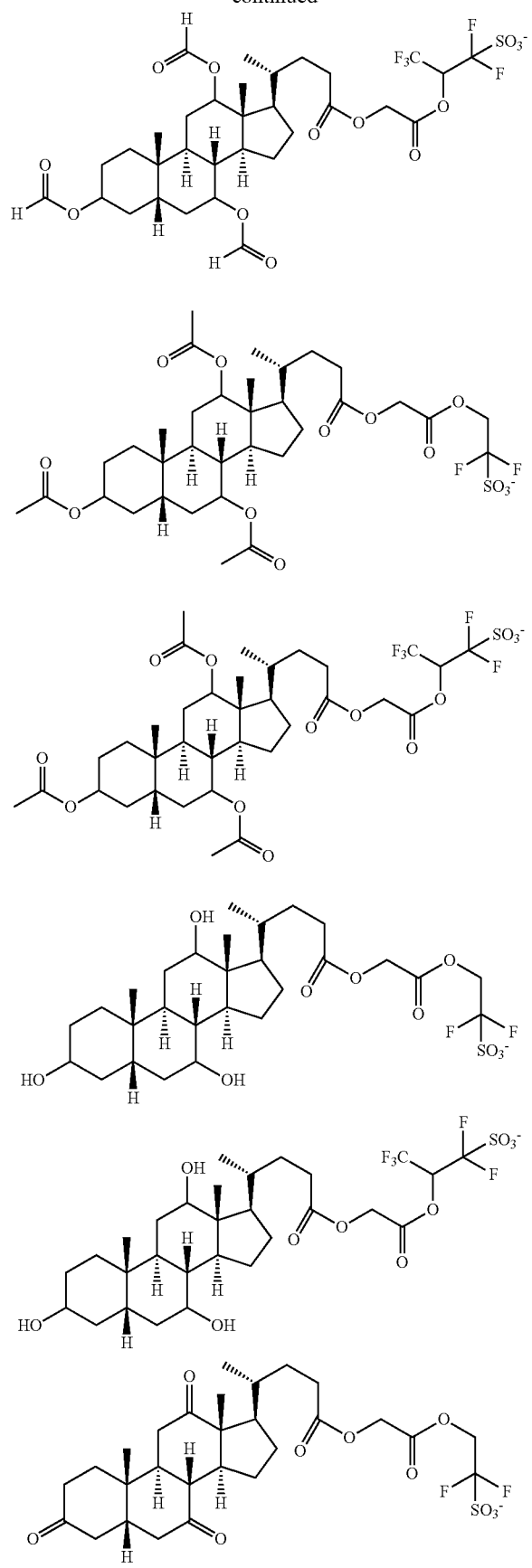
108
-continued
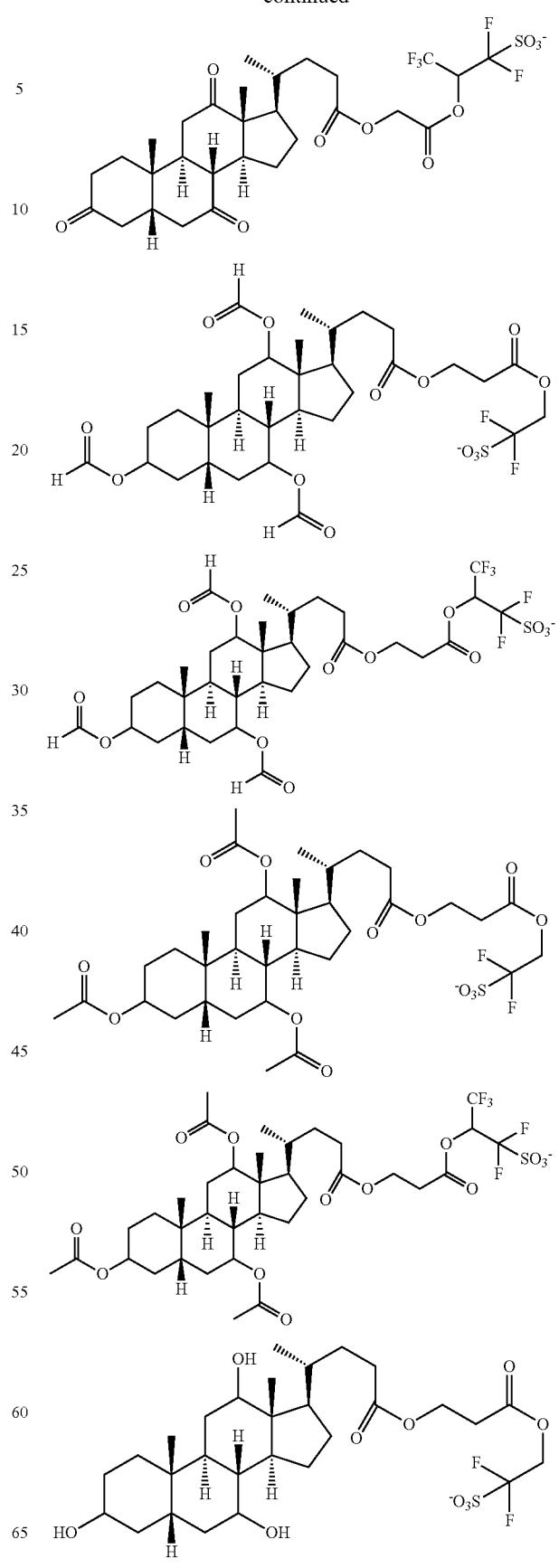

109
-continued
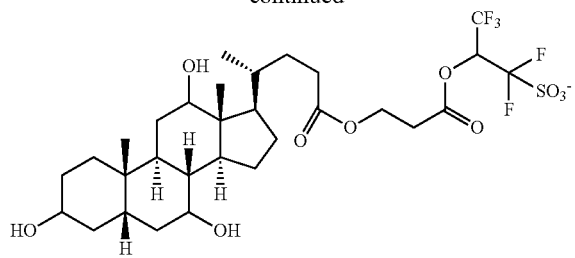
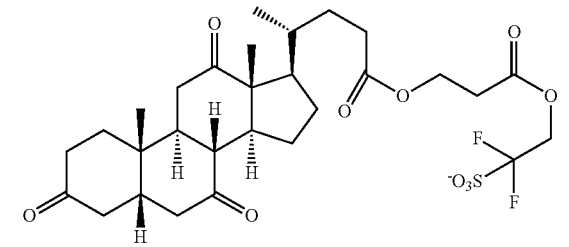
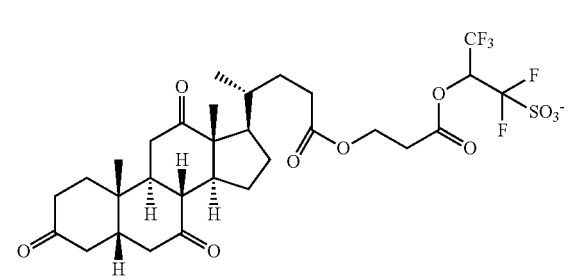
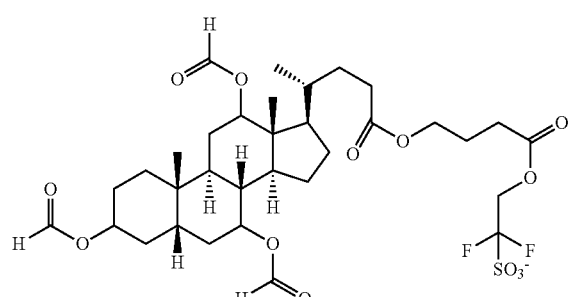
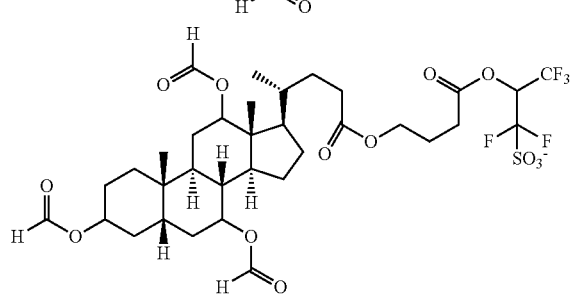
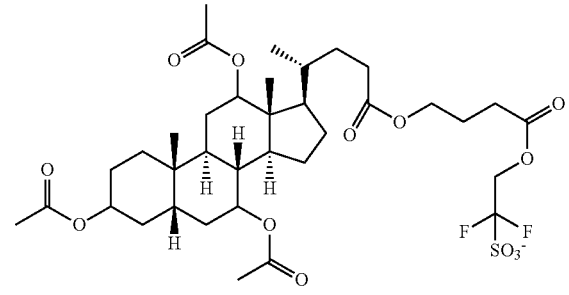
110
-continued
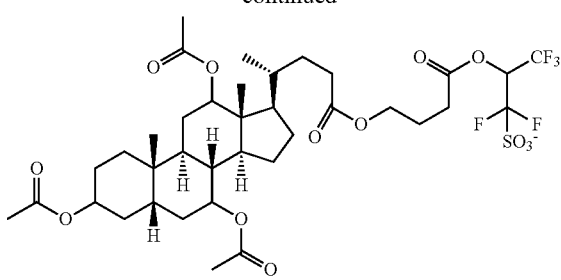
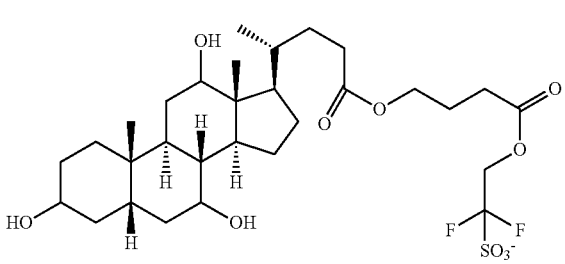
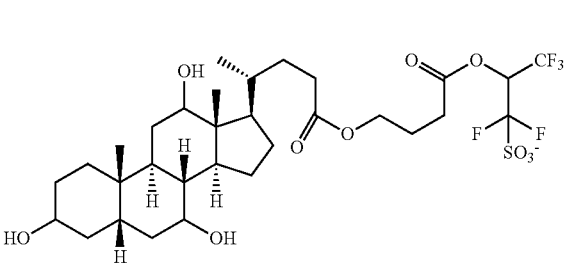
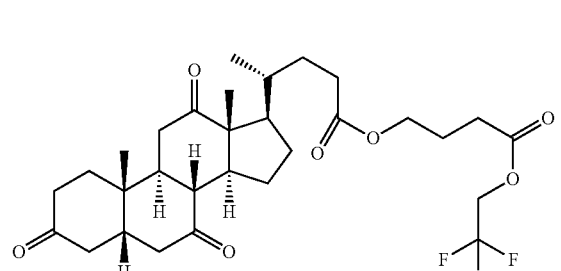
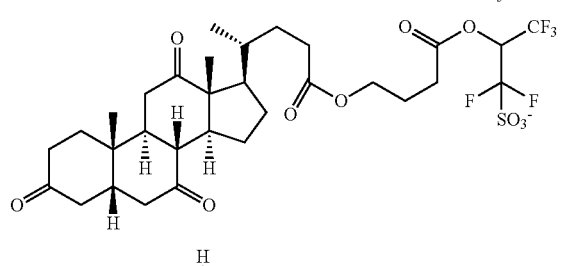
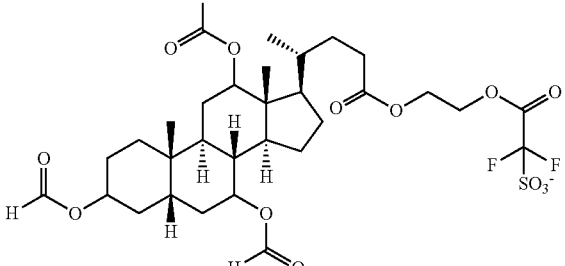

-continued

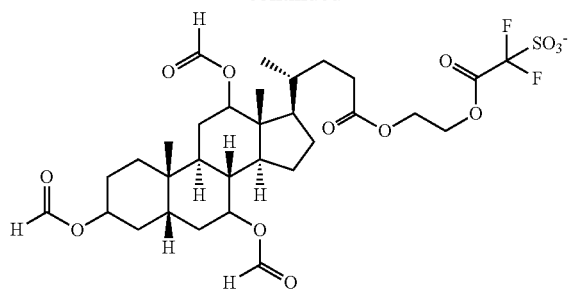

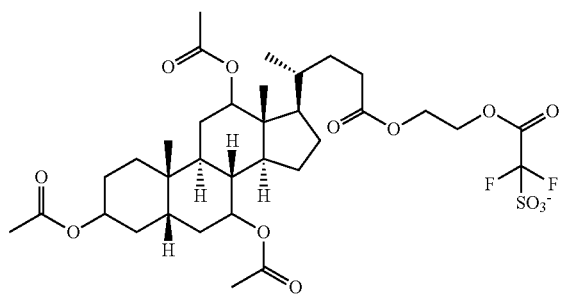

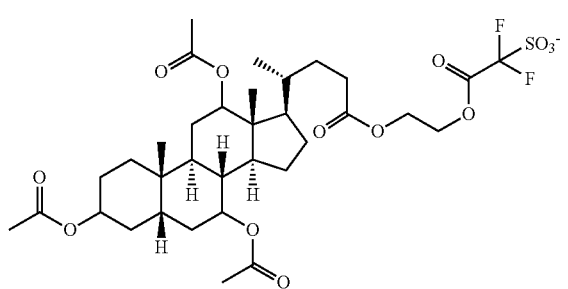

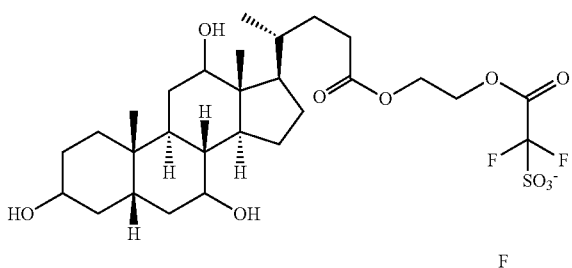

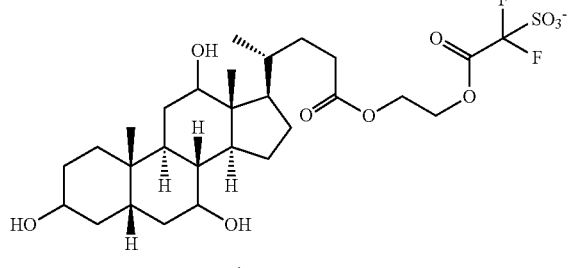

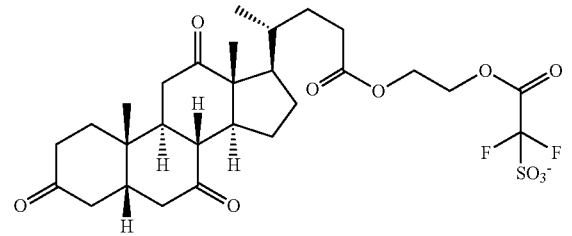

-continued

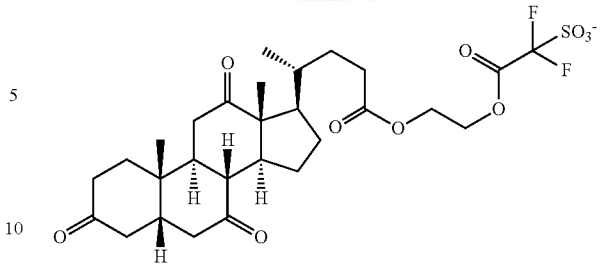

In the formula (B-1-2), $R^{2B}$ and $R^{3B}$ each independently represent a fluorine atom, a trifluoromethyl group, a pentafluoroethyl group, a trifluoroethyl group, an octafluorobutyl group, or a nonafluorobutyl group, and $R^{2B}$ and $R^{3B}$ are optionally bonded with each other to form a ring with —SO$_2$N$^-$SO$_2$—, in which case $R^{2B}$ and $R^{3B}$ are preferably bonded with each other to form —(CF$_2$)$_k$— (k is an integer of 2 to 5).

In the formula (B-1-3), $R^{4B}$, $R^{5B}$, and $R^{6B}$ each represent a fluorine atom, a trifluoromethyl group, a pentafluoroethyl group, a trifluoroethyl group, an octafluorobutyl group, or a nonafluorobutyl group.

The content of the sensitizer is preferably 0.01 to 100 parts by mass, more preferably 0.1 to 50 parts by mass relative to 100 parts by mass of the component (A). The sensitizer may be used alone or in combination of two or more kinds.

<Other Components>

The first resist material and the second resist material used for the present invention may further contain a solvent. The solvent used for the present invention is not particularly limited if it can dissolve each components other than the solvent, and is preferably the same one as the solvent finally added to prepare the thermosetting compound or the component (A). Illustrative examples thereof include butanediol monomethyl ether, propylene glycol monomethyl ether, ethylene glycol monomethyl ether, butanediol monoethyl ether, propylene glycol monoethyl ether, ethylene glycol monoethyl ether, butanediol monopropyl ether, propylene glycol monopropyl ether, ethylene glycol monopropyl ether, ethylene glycol monobutyl ether, diethylene glycol monomethyl ether, diethylene glycol monoethyl ether, diethylene glycol monopropyl ether, diethylene glycol monobutyl ether, propylene glycol monobutyl ether, 1-butanol, 2-butanol, 2-methyl-1-propanol, 4-methyl-2-pentanol, acetone, tetrahydrofuran, toluene, hexane, ethyl acetate, cyclohexanone, methyl pentyl ketone, propylene glycol dimethyl ether, diethylene glycol dimethyl ether, dipentyl ether, propylene glycol monomethyl ether acetate, propylene glycol monoethyl ether acetate, ethyl pyruvate, butyl acetate, methyl 3-methoxypropionate, ethyl 3-ethoxypropionate, tert-butyl acetate, tert-butyl propionate, propylene glycol mono-tert-butyl ether acetate, γ-butyrolactone, methyl isobutyl ketone, cyclopentyl methyl ether, etc.

When an organic solvent is contained, the amount is preferably 100 to 10,000 parts by mass, more preferably 500 to 7,000 parts by mass relative to 100 parts by mass of the thermosetting compound or the component (A). The organic solvent may be used alone or in combination of two or more kinds.

Additionally, the first resist material and the second resist material used for the present invention can contain a surfactant in accordance with needs. As such a material, specifically, a material described in paragraph [0129] of JP2009-126940A can be added.

[Steps (1) to (4)]

Hereinafter, each of the steps (1) to (4) of the inventive patterning process will be described more specifically, but the inventive patterning process is not limited thereto and can be applied to known lithography technologies used for producing various integrated circuits and masks, for example.

<Step (1)>

The step (1) is a step of coating a substrate to be processed with the first resist material containing a thermosetting compound having a hydroxy group and/or a carboxy group each protected by an acid-labile group, together with an acid generator, followed by baking treatment to form the first resist film, which is insoluble to an organic solvent.

For example, the first resist material containing the thermosetting compound used for the present invention is applied onto a substrate for producing an integrated circuit or a layer to be processed on the substrate (Si, $SiO_2$, SiN, SiON, TiN, WSi, BPSG, SOG, an organic antireflective film, etc.), alternatively, on a substrate for producing a mask circuit or a layer to be processed on the substrate (Cr, CrO, CrON, $MoSi_2$, $SiO_2$, etc.) by appropriate coating method such as spin coating, roll coating, flow coating, dip coating, spray coating, and doctor coating so as to have a coating thickness of 0.01 to 2.0 μm. This is subjected to pre-baking on a hot plate, for example, at 60 to 350° C. for 10 seconds to 30 minutes, preferably at 100 to 300° C. for 30 seconds to 20 minutes to form the first resist film (film of thermosetting compound).

<Step (2)>

The step (2) is a step of coating the first resist film with the second resist material containing a component (A) of at least one element selected from a metal compound as well as a hydrolysate, a condensate, and a hydrolysis condensate of the metal compound, together with the sensitizer, followed by baking treatment to form the second resist film.

The coating and the baking treatment can be performed under the same conditions as in the step (1).

<Step (3)>

The step (3) is a step of irradiating the first resist film and the second resist film with a high energy beam from a light source of an extreme ultraviolet ray with a wavelength of 3 to 15 nm or an electron beam to perform pattern exposure to deprotect the hydroxy group and/or the carboxy group in a pattern exposed portion of the first resist film and to form a crosslinked portion in which the component (A) and the deprotected hydroxy group and/or the deprotected carboxy group are crosslinked on the pattern exposed portion.

For example, the first resist film (film of thermosetting compound) and the second resist film are exposed to a high energy beam through a designated mask or directly to form an intended pattern. The high energy beam includes excimer laser of KrF, ArF, Xe, $F_2$, $Ar_2$, etc. as well as EUV and EB. The energy of exposure triggers elimination of the organic group (protective group) to generate an acid functional group in the first resist film, thereby causing crosslinking reaction with a metal compound applied thereon to enhance the insolubility in an organic solvent. In this way, the film functions as a negative resist material. In this case, the high energy beam is preferably EUV with a wavelength of 3 to 15 nm and EB with an acceleration voltage of 1 to 150 kV, more preferably EB with an acceleration voltage of 5 to 120 kV, still more preferably 50 kV or less, particularly low energy EB with an acceleration voltage of 10 kV or less. They have shorter wavelength than excimer laser and are preferably used because exposure to EUV or EB, which have higher energy density, brings higher efficiency for deprotecting reaction of a hydroxy group and/or a carboxy group. The exposure of high energy beam is preferably about 1 $mJ/cm^2$ to 1 $J/cm^2$, particularly 10 to 500 $mJ/cm^2$, or about 0.1 to 1 $mC/cm^2$, particularly 0.5 to 500 $\mu C/cm^2$.

The exposed first resist film and the second resist film may be subjected to baking (PEB) on a hot plate. The PEB treatment can be performed preferably at 60 to 350° C. for 10 seconds to 30 minutes, more preferably at 100 to 300° C. for 30 seconds to 20 minutes.

<Step (4)>

The step (4) is a step of developing the second resist film with a developer to give a metal film pattern composed of the crosslinked portion.

For example, development is performed by an ordinary method such as a dip method, a puddle method, and a spray method using an organic solvent developer preferably for 0.1 to 3 minutes, more preferably for 0.5 to 2 minutes to dissolve the unexposed portion to form a negative pattern on a substrate. Preferable examples of the developer include 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate (amyl acetate), butenyl acetate, isopentyl acetate (isoamyl acetate), propyl formate, butyl formate, isobutyl formate, pentyl formate (amyl formate), isopentyl formate (isoamyl formate), methyl valerate, methyl pentenoate, methyl crotonate, ethyl crotonate, methyl lactate, ethyl lactate, propyl lactate, butyl lactate, isobutyl lactate, pentyl lactate (amyl lactate), isopentyl lactate (isoamyl lactate), methyl 2-hydroxy-isobutyrate, ethyl 2-hydroxy-isobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, 2-phenylethyl acetate, etc.

After finishing the development, it is preferable to perform rinsing. The rinsing liquid is preferably a solvent that is compatible with the developer and does not dissolve the resist film. As such a solvent, it is preferable to use a solvent such as alcohol having 3 to 10 carbon atoms, an ether compound having 8 to 12 carbon atoms, as well as alkane, alkene, and alkyne each having 6 to 12 carbon atoms, and aromatic solvents.

Illustrative examples of the alcohol having 3 to 10 carbon atoms include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, 1-octanol, etc.

Illustrative examples of the ether compound having 8 to 12 carbon atoms include di-n-butyl ether, diisobutyl ether, di-sec-butyl ether, di-n-pentyl ether, di-isopentyl ether, di-sec-pentyl ether, di-tert-pentyl ether, di-n-hexyl ether, etc.

Illustrative examples of the alkane having 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, cyclononane, etc. Illustrative examples of the alkene having 6 to 12 carbon atoms include hexene, heptene, octene, cyclohexene, methylcyclohexene, dimethylcyclohexene, cycloheptene, cyclooctene, etc. Illustrative examples of the alkyne having 6 to 12 carbon atoms include hexyne, heptyne, octyne, etc.

Illustrative examples of the aromatic solvent include toluene, xylene, ethylbenzene, isopropylbenzene, tert-butylbenzene, mesitylene, etc.

EXAMPLE

Hereinafter, the present invention will be described specifically by showing Examples and Comparative Examples, but the present invention is not limited the following Examples. Incidentally, Mw is a value measured by GPC in terms of polystyrene using tetrahydrofuran (THF) as a solvent.

[1] Synthesis of Component (A)

Synthesis Example 1

To solution of 284 g of titanium tetraisopropoxide (manufactured by Tokyo Chemical Industry Co., Ltd.) in 500 g of 2-propanol (IPA), solution of 27 g of deionized water in 500 g of IPA was added dropwise at room temperature over 2 hours with stirring. To the obtained solution, 180 g of 2,4-dimethyl-2,4-octanediol was added, and this was stirred at room temperature for 30 minutes. This solution was concentrated at 30° C. under reduced pressure, then heated to 60° C., and kept heating under reduced pressure until a distillate was not obtained. After the distillate was not observed, 1,200 g of 4-methyl-2-pentanol (MIBC) was added, and this was heated at 40° C. under reduced pressure until the IPA distillate was not obtained to afford 1,000 g of solution of Titanium-containing compound A1 in MIBC (concentration of the compound: 25 mass %). The molecular weight thereof was measured in terms of polystyrene to find that Mw=1,200.

Synthesis Example 2

To solution of 284 g of titanium tetraisopropoxide (manufactured by Tokyo Chemical Industry Co., Ltd.) in 500 g of IPA, solution of 27 g of deionized water in 500 g of IPA was added dropwise at room temperature over 2 hours with stirring. To the obtained solution, 120 g of 2-methyl-2,4-pentanediol was added, and this was stirred at room temperature for 30 minutes. This solution was concentrated at 30° C. under reduced pressure, then heated to 60° C., and kept heating under reduced pressure until a distillate was not obtained. After the distillate was not observed, 1,200 g of MIBC was added, and this was heated at 40° C. under reduced pressure until the IPA distillate was not obtained to afford 1,000 g of solution of Titanium-containing compound A2 in MIBC (concentration of the compound: 20 mass %). The molecular weight thereof was measured in terms of polystyrene to find that Mw=1,100.

Synthesis Example 3

To solution of 40 g of titanium tetrabutoxide tetramer (manufactured by Tokyo Chemical Industry Co., Ltd.) in 10 g of 1-butanol (BuOH), 24 g of 2,4-dimethyl-2,4-hexanediol was added, and this was stirred at room temperature for 30 minutes. This solution was concentrated at 50° C. under reduced pressure, then heated to 60° C., and kept heating under reduced pressure until a distillate was not obtained. After the distillate was not observed, 200 g of propylene glycol monomethyl ether acetate (PGMEA) was added, and this was heated at 50° C. under reduced pressure until the BuOH distillate was not obtained to afford 160 g of solution of Titanium-containing compound A3 in PGMEA (concentration of the compound: 25 mass %). The molecular weight thereof was measured in terms of polystyrene to find that Mw=1,000.

Synthesis Example 4

To solution of 243 g of titanium tetrabutoxide tetramer (manufactured by Tokyo Chemical Industry Co., Ltd.) in 500 g of BuOH, 130 g of pinacol was added, and this was stirred at room temperature for 30 minutes. This solution was concentrated at 40° C. under reduced pressure, then heated to 60° C., and kept heating under reduced pressure until a distillate was not obtained. After the distillate was not observed, 1,200 g of PGMEA was added, and this was heated at 50° C. under reduced pressure until the BuOH distillate was not obtained to afford 1,000 g of solution of Titanium-containing compound A4 in PGMEA (concentration of the compound: 22 mass %). The molecular weight thereof was measured in terms of polystyrene to find that Mw=1,150.

[2] Preparation of Resist Material

The thermosetting compounds X1 to X4, photo-acid generator P1 and a solvent were mixed according to the compositions shown in Table 1 to prepare Resist materials 1-1 to 1-6 and Comparative resist materials 1-1 to 1-2 as the first resist materials. Titanium-containing compounds A1 to A4 as the component (A), metal salt sensitizer B1, and a solvent were mixed according to the compositions shown in Table 1, and this was filtered through a 0.1 μm filter made of fluorine resin to prepare Resist materials 2-1 to 2-6 and Comparative resist materials 2-1 to 2-3 as the second resist materials.

(X1)

(X2)

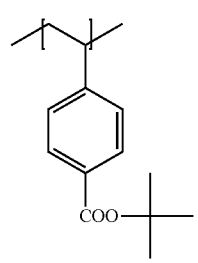

-continued

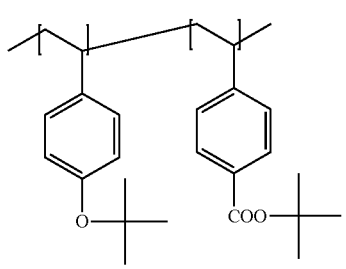
(X3)

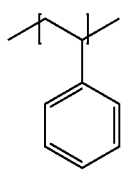
(X4)

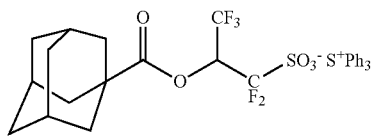
(P1)

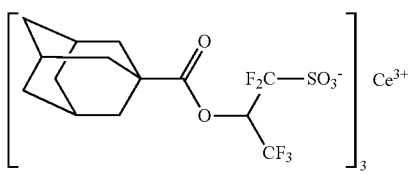
(B1)

[3] Surface Analysis (Elemental Analysis and Evaluation of Film Thickness of Pattern)

Examples 1-1 to 1-6, Comparative Examples 1-1 to 1-2

Onto an Si substrate with a diameter of 8 inches (200 mm), each of Resist materials 1-1 to 1-6 and Comparative resist materials 1-1 to 1-2 was applied by spin-coating using CLEAN TRACK ACT8 (manufactured by Tokyo Electron Limited.) and baked on a hot plate at 200° C. for 60 seconds to prepare the first resist film (film of thermosetting compound) with a thickness of 100 nm. Onto the formed film, each of Resist materials 2-1 to 2-6 and Comparative resist materials 2-1 to 2-2 was applied by spin-coating and baked at 150° C. for 60 seconds to prepare the second resist film (film of metal oxide-containing compound) with a thickness of 100 nm. This was exposed to EUV using NXE3300 (manufactured by ASML Holding), subjected to puddle development with butyl acetate for 20 seconds using CLEAN TRACK ACT8 to remove the soluble portion, and baked at 230° C. for 60 seconds. The obtained film was measured to calculate the ratio of elements on the surface using XPS K-ALPHA Surface Analysis (manufactured by Thermo Fisher Scientific K.K.). The film thickness of the metal pattern was calculated from the difference between the thicknesses of exposed portion and unexposed portion using AFM NX20 (manufactured by Park Systems). The results are shown in Table 2.

Comparative Example 1-3

Onto an Si substrate with a diameter of 8 inches (200 mm), Comparative resist material 2-3 was applied by spin-coating and baked at 150° C. for 60 seconds to prepare the second resist film (film of metal oxide-containing compound) with a thickness of 100 nm. This was exposed to EUV using NXE3300 (manufactured by ASML Holding), baked at 230° C. for 60 seconds, and then subjected to puddle development with butyl acetate for 20 seconds using CLEAN TRACK ACT8 to remove the soluble portion. The formed film was measured to calculate the ratio of elements on the surface using XPS K-ALPHA Surface Analysis (manufactured by Thermo Fisher Scientific K.K.). The film thickness of the metal pattern was calculated from the difference between the thicknesses of exposed portion and unexposed portion using AFM NX20 (manufactured by Park Systems). The results are shown in Table 2.

TABLE 1

| Resist material | Resist material 1 formulation (parts by mass) | | | Resist material | Resist material 2 formulation (parts by mass) | | |
|---|---|---|---|---|---|---|---|
| | Thermosetting compound | Acid generator | Solvent | | Component (A) | Sensitizer | Solvent |
| Resist material 1-1 | X1 (100) | P1 (1) | PGMEA (2000) | Resist material 2-1 | A1 (100) | B1 (1) | MIBC (2000) |
| Resist material 1-2 | X1 (100) | P1 (1) | PGMEA (2000) | Resist material 2-2 | A2 (100) | B1 (1) | MIBC (2000) |
| Resist material 1-3 | X1 (100) | P1 (1) | PGMEA (2000) | Resist material 2-3 | A3 (100) | B1 (1) | PGMEA (2000) |
| Resist material 1-4 | X1 (100) | P1 (1) | PGMEA (2000) | Resist material 2-4 | A4 (100) | B1 (1) | PGMEA (2000) |
| Resist material 1-5 | X2 (100) | P1 (1) | PGMEA (2000) | Resist material 2-5 | A3 (100) | B1 (1) | PGMEA (2000) |
| Resist material 1-6 | X3 (100) | P1 (1) | PGMEA (2000) | Resist material 2-6 | A3 (100) | B1 (1) | PGMEA (2000) |
| Comparative resist material 1-1 | X4 (100) | — | PGMEA (2000) | Comparative resist material 2-1 | A2 (100) | B1 (1) | PGMEA (2000) |
| Comparative resist material 1-2 | X4 (100) | P1 (1) | PGMEA (2000) | Comparative resist material 2-2 | A3 (100) | B1 (1) | PGMEA (2000) |
| | | | | Comparative resist material 2-3 | A3 (100) | B1 (1) | PGMEA (2000) |

TABLE 2

| | Resist material 1 | Resist material 2 | Atomic % Ti | Atomic % O | Atomic % C | Film thickness (nm) |
|---|---|---|---|---|---|---|
| Example 1-1 | Resist material 1-1 | Resist material 2-1 | 10.4 | 60.2 | 29.4 | 5.1 |
| Example 1-2 | Resist material 1-2 | Resist material 2-2 | 10.5 | 61.2 | 28.3 | 5.2 |
| Example 1-3 | Resist material 1-3 | Resist material 2-3 | 11.1 | 59.1 | 29.8 | 5.5 |
| Example 1-4 | Resist material 1-4 | Resist material 2-4 | 10.5 | 63.1 | 26.4 | 5.2 |
| Example 1-5 | Resist material 1-5 | Resist material 2-5 | 10.9 | 58.9 | 30.2 | 5.4 |
| Example 1-6 | Resist material 1-6 | Resist material 2-6 | 10.7 | 60.2 | 29.1 | 5.5 |
| Comparative Example 1-1 | Comparative resist material 1-1 | Comparative resist material 2-1 | 1.2 | 40.6 | 58.2 | 1.1 |
| Comparative Example 1-2 | Comparative resist material 1-2 | Comparative resist material 2-2 | 1.1 | 43.2 | 55.7 | 1.2 |
| Comparative Example 1-3 | — | Comparative resist material 2-3 | 10.6 | 58.3 | 31.1 | 1.1 |

[4] EB Drawing Evaluation (Patterning)

Examples 2-1 to 2-6, Comparative Examples 2-1 to 2-2

Onto an Si substrate with a diameter of 8 inches (200 mm) treated with HMDS vapor prime, each of Resist materials 1-1 to 1-6 and Comparative resist materials 1-1 to 1-2 was applied by spin-coating using CLEAN TRACK ACT8 and baked on a hot plate at 200° C. for 60 seconds to prepare the first resist film (film of thermosetting compound) with a thickness of 100 nm. Onto the formed film, each of Resist materials 2-1 to 2-6 and Comparative resist materials 2-1 to 2-2 was applied by spin-coating and baked at 150° C. for 60 seconds to prepare the second resist film (film of metal oxide-containing compound) with a thickness of 100 nm. This was subjected to drawing in a vacuum chamber with an acceleration voltage of 50 kV using JBX-9000MV (manufactured by JEOL Ltd.). After the drawing, this was subjected to paddle development with butyl acetate for 20 seconds using CLEAN TRACK ACT8 and baked on a hot plate at 230° C. for 60 seconds to form a negative pattern. The obtained resist pattern was evaluated as follows: the exposure dose to resolve a 100 nm line-and-space (LS) as 1:1 was defined as sensitivity, and at the exposure dose, the minimum size was defined as resolution, and the edge roughness of the 100 nm LS (LWR) was measured using SEM (manufactured by Hitachi High-Tech Fielding Corporation). The results are shown in Table 3.

Comparative Example 2-3

Onto an Si substrate with a diameter of 8 inches (200 mm) treated with HMDS vapor prime, Comparative resist material 2-3 was applied by spin-coating and baked at 150° C. for 60 seconds to prepare the second resist film (film of metal oxide-containing compound) with a thickness of 100 nm. This was subjected to drawing in a vacuum chamber with an acceleration voltage of 50 kV using JBX-9000MV (manufactured by JEOL Ltd.). After the drawing, this was baked on a hot plate at 230° C. for 60 seconds and subjected to paddle development with butyl acetate for 20 seconds using CLEAN TRACK ACT8 to form a negative pattern. The obtained resist pattern was evaluated as follows: the exposure dose to resolve a 100 nm line-and-space (LS) as 1:1 was defined as sensitivity, and at the exposure dose, the minimum size was defined as resolution, and the edge roughness of the 100 nm LS (LWR) was measured using SEM (manufactured by Hitachi High-Tech Fielding Corporation). The results are shown in Table 3.

TABLE 3

| | Resist material 1 | Resist material 2 | Sensitivity ($\mu C/cm^{-2}$) | Resolution (nm) | LWR (nm) |
|---|---|---|---|---|---|
| Example 2-1 | Resist material 1-1 | Resist material 2-1 | 230 | 65 | 2.2 |
| Example 2-2 | Resist material 1-2 | Resist material 2-2 | 240 | 60 | 2.1 |
| Example 2-3 | Resist material 1-3 | Resist material 2-3 | 200 | 60 | 2.4 |
| Example 2-4 | Resist material 1-4 | Resist material 2-4 | 230 | 65 | 2.2 |
| Example 2-5 | Resist material 1-5 | Resist material 2-5 | 200 | 60 | 2.3 |
| Example 2-6 | Resist material 1-6 | Resist material 2-6 | 200 | 60 | 2.4 |
| Comparative Example 2-1 | Comparative resist material 1-1 | Comparative resist material 2-1 | 390 | 85 | 2.2 |
| Comparative Example 2-2 | Comparative resist material 1-2 | Comparative resist material 2-2 | 400 | 85 | 2.3 |
| Comparative Example 2-3 | — | Comparative resist material 2-3 | 400 | 90 | 4.1 |

The results of Examples 1-1 to 1-6 revealed that the inventive patterning process makes it possible to form a metal film pattern in a form of thin film containing metal (Ti). Additionally, the results of Examples 2-1 to 2-6 revealed that the inventive patterning process achieves good processability of thin film, higher sensitivity, and sufficient resolution.

On the other hand, in Comparative Examples 1-1 and 1-2, the first resist material did not have a thermosetting compound having a hydroxy group or a carboxy group protected by an acid labile group, thereby being unable to form a crosslinked portion with the component (A) to fail to form a metal film pattern. In Comparative Example 1-3 without using the first resist material, it was possible to form a metal pattern, but impossible to obtain sufficient film thickness compared to those of Examples. In Comparative Examples 2-1 to 2-3, it was also impossible to obtain sufficient sensitivity and resolution compared to those of Examples.

The above results have revealed that the inventive patterning process achieves good processability of thin film, higher sensitivity, and sufficient resolution.

It is to be noted that the present invention is not limited to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A patterning process to form a metal film pattern on a coated film having an exposure pattern formed thereon, comprising the steps of:
   (1) coating a substrate to be processed with a first resist material containing an acid generator and a thermosetting compound having a hydroxy group and/or a carboxy group each protected by an acid-labile group, followed by baking treatment to form a first resist film being insoluble to an organic solvent;

(2) coating the first resist film with a second resist material containing a sensitizer and a component (A) of at least one element selected from the group consisting of a metal compound, a hydrolysate of the metal compound, a condensate of the metal compound, and a hydrolysis condensate of the metal compound, followed by baking treatment to form a second resist film;

(3) irradiating the first resist film and the second resist film with a high energy beam from a light source of an extreme ultraviolet ray with a wavelength of 3 to 15 nm or an electron beam to perform pattern exposure to deprotect the hydroxy group and/or the carboxy group in a pattern exposed portion of the first resist film and to form a crosslinked portion in which the component (A) and the deprotected hydroxy group and/or the deprotected carboxy group are crosslinked on the pattern exposed portion; and (4) developing the second resist film with a developer to give a metal film pattern composed of the crosslinked portion.

2. The patterning process according to claim 1, wherein the baking treatment in the step (1) and/or the step (2) is performed at a temperature of 50° C. or more.

3. The patterning process according to claim 2, wherein the component (A) is at least one element selected from the group consisting of a metal compound shown by the following general formula (A-1), a hydrolysate of the metal compound shown by the following general formula (A-1), a condensate of the metal compound shown by the following general formula (A-1), and a hydrolysis condensate of the metal compound shown by the following general formula (A-1), and/or at least one element selected from the group consisting of a condensate and a hydrolysis condensate of a metal compound shown by the following general formula (A-2) and the metal compound shown by the general formula (A-1):

$$M(OR^{14})_4 \quad (A-1)$$

wherein M represents Ti, Zr, or Hf; and $R^{14}$ represents a monovalent organic group having 1 to 20 carbon atoms and 0 or 1 hydroxy group;

$$M'X \quad (A-2)$$

wherein M' represents Ti, Zr, or Hf; and X represents a divalent or trivalent alcohol shown by the following general formula (A-3):

$$R^{24}(OH)_m \quad (A-3)$$

wherein $R^{24}$ represents an m-valent organic group having 2 to 20 carbon atoms and 0 or 1 hydroxy group; and "m" is an integer of 2 or 3.

4. The patterning process according to claim 3, wherein the sensitizer is one or more elements selected from sensitizers shown by the following general formula (B-1):

$$M'''^+(Y^-)_n \quad (B-1)$$

wherein $M'''^+$ represents an ion of a metal selected from Mg, Ca, Ce, Zn, Cu, In, Fe, Yb, Y, Tm, Sn, Ni, Sc, Hf, Nb, Ti, Zr, Ba, Ho, Tb, Lu, La, Ag, Eu, Dy, Gd, Rb, Sr, and Cs; $Y^-$ represents an alkylsulfonate ion, an arylsulfonate ion, an alkylsulfonimidate ion, or an alkylsulfonmethidate ion each having at least one fluorine atom; and "n" is an integer satisfying 1≤n≤4.

5. The patterning process according to claim 4, wherein $Y^-$ in the general formula (B-1) is shown by any of the following general formulae (B-1-1) to (B-1-3):

$$R^{1B}—SO_3^- \quad (B-1-1)$$

$$R^{2B}—SO_2—N^-—SO_2-R^{3B} \quad (B-1-2)$$

$$R^{4B}—SO_2—C^-—SO_2-R^{5B} \quad (B-1-3)$$
$$\phantom{R^{4B}—SO_2—}|$$
$$\phantom{R^{4B}—SO_2—}SO_2$$
$$\phantom{R^{4B}—SO_2—}|$$
$$\phantom{R^{4B}—SO_2—}R^{6B}$$

wherein $R^{1B}$ represents a linear, branched, or cyclic alkyl group, alkenyl group, or alkynyl group having 5 to 30 carbon atoms, or an aryl group or aralkyl group having 6 to 30 carbon atoms, each having at least one fluorine atom and optionally having a halogen atom, an ether group, a thiol group, an ester group, a carbonate group, a carbonyl group, an amide group, an amino group, an azide group, a carbamate group, a nitro group, a cyano group, a hydroxy group, a carboxy group, a sulfo group, a sulfonate ester group, a sultone group, a lactone ring, or a lactam ring; $R^{2B}$, $R^{3B}$, $R^{4B}$, $R^{5B}$, and $R^{6B}$ each represent a fluorine atom, a trifluoromethyl group, a pentafluoroethyl group, a trifluoroethyl group, an octafluorobutyl group, or a nonafluorobutyl group, and $R^{2B}$ and $R^{3B}$ are optionally bonded with each other to form a ring.

6. The patterning process according to claim 3, wherein the developer in the step (4) is an organic solvent.

7. The patterning process according to claim 6, wherein the organic solvent is one or more solvents selected from 2-octanone, 2-nonanone, 2-heptanone, 3-heptanone, 4-heptanone, 2-hexanone, 3-hexanone, diisobutyl ketone, methyl cyclohexanone, acetophenone, methylacetophenone, propyl acetate, butyl acetate, isobutyl acetate, amyl acetate, butenyl acetate, isoamyl acetate, propyl formate, butyl formate, isobutyl formate, amyl formate, isoamyl formate, methyl valerate, methyl pentenoate, methyl crotonate, ethyl crotonate, methyl lactate, ethyl lactate, propyl lactate, butyl lactate, isobuthyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

8. The patterning process according to claim 2, wherein the sensitizer is one or more elements selected from sensitizers shown by the following general formula (B-1):

$$M'''^+(Y^-)_n \quad (B-1)$$

wherein $M'''^+$ represents an ion of a metal selected from Mg, Ca, Ce, Zn, Cu, In, Fe, Yb, Y, Tm, Sn, Ni, Sc, Hf, Nb, Ti, Zr, Ba, Ho, Tb, Lu, La, Ag, Eu, Dy, Gd, Rb, Sr, and Cs; $Y^-$ represents an alkylsulfonate ion, an arylsulfonate ion, an alkylsulfonimidate ion, or an alkylsulfonmethidate ion each having at least one fluorine atom; and "n" is an integer satisfying 1≤n≤4.

9. The patterning process according to claim 8, wherein $Y^-$ in the general formula (B-1) is shown by any of the following general formulae (B-1-1) to (B-1-3):

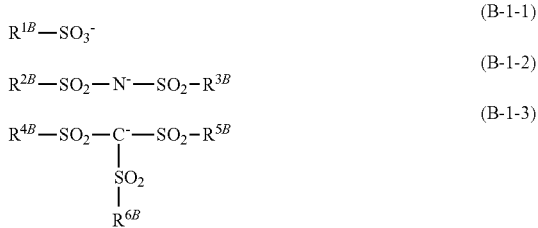

wherein $R^{1B}$ represents a linear, branched, or cyclic alkyl group, alkenyl group, or alkynyl group having 5 to 30 carbon atoms, or an aryl group or aralkyl group having 6 to 30 carbon atoms, each having at least one fluorine atom and optionally having a halogen atom, an ether group, a thiol group, an ester group, a carbonate group, a carbonyl group, an amide group, an amino group, an azide group, a carbamate group, a nitro group, a cyano group, a hydroxy group, a carboxy group, a sulfo group, a sulfonate ester group, a sultone group, a lactone ring, or a lactam ring; $R^{2B}$, $R^{3B}$, $R^{4B}$, $R^{5B}$, and $R^{6B}$ each represent a fluorine atom, a trifluoromethyl group, a pentafluoroethyl group, a trifluoroethyl group, an octafluorobutyl group, or a nonafluorobutyl group, and $R^{2B}$ and $R^{3B}$ are optionally bonded with each other to form a ring.

10. The patterning process according to claim 2, wherein the developer in the step (4) is an organic solvent.

11. The patterning process according to claim 10, wherein the organic solvent is one or more solvents selected from 2-octanone, 2-nonanone, 2-heptanone, 3-heptanone, 4-heptanone, 2-hexanone, 3-hexanone, diisobutyl ketone, methyl cyclohexanone, acetophenone, methylacetophenone, propyl acetate, butyl acetate, isobutyl acetate, amyl acetate, butenyl acetate, isoamyl acetate, propyl formate, butyl formate, isobutyl formate, amyl formate, isoamyl formate, methyl valerate, methyl pentenoate, methyl crotonate, ethyl crotonate, methyl lactate, ethyl lactate, propyl lactate, butyl lactate, isobuthyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

12. The patterning process according to claim 1, wherein the component (A) is at least one element selected from the group consisting of a metal compound shown by the following general formula (A-1), a hydrolysate of the metal compound shown by the following general formula (A-1), a condensate of the metal compound shown by the following general formula (A-1), and a hydrolysis condensate of the metal compound shown by the following general formula (A-1), and/or at least one element selected from the group consisting of a condensate and a hydrolysis condensate of a metal compound shown by the following general formula (A-2) and the metal compound shown by the general formula (A-1):

wherein M represents Ti, Zr, or Hf; and $R^{1A}$ represents a monovalent organic group having 1 to 20 carbon atoms and 0 or 1 hydroxy group;

wherein M' represents Ti, Zr, or Hf; and X represents a divalent or trivalent alcohol shown by the following general formula (A-3):

$$R^{2A}(OH)_m \quad (A-3)$$

wherein $R^{2A}$ represents an m-valent organic group having 2 to 20 carbon atoms and 0 or 1 hydroxy group; and "m" is an integer of 2 or 3.

13. The patterning process according to claim 12, wherein the sensitizer is one or more elements selected from sensitizers shown by the following general formula (B-1):

$$M'^{n+}(Y^-)_n \quad (B-1)$$

wherein represents an ion of a metal selected from Mg, Ca, Ce, Zn, Cu, In, Fe, Yb, Y, Tm, Sn, Ni, Sc, Hf, Nb, Ti, Zr, Ba, Ho, Tb, Lu, La, Ag, Eu, Dy, Gd, Rb, Sr, and Cs; $Y^-$ represents an alkylsulfonate ion, an arylsulfonate ion, an alkylsulfonimidate ion, or an alkylsulfonmethidate ion each having at least one fluorine atom; and "n" is an integer satisfying $1 \leq n \leq 4$.

14. The patterning process according to claim 13, wherein $Y^-$ in the general formula (B-1) is shown by any of the following general formulae (B-1-1) to (B-1-3):

wherein $R^{1B}$ represents a linear, branched, or cyclic alkyl group, alkenyl group, or alkynyl group having 5 to 30 carbon atoms, or an aryl group or aralkyl group having 6 to 30 carbon atoms, each having at least one fluorine atom and optionally having a halogen atom, an ether group, a thiol group, an ester group, a carbonate group, a carbonyl group, an amide group, an amino group, an azide group, a carbamate group, a nitro group, a cyano group, a hydroxy group, a carboxy group, a sulfo group, a sulfonate ester group, a sultone group, a lactone ring, or a lactam ring; $R^{2B}$, $R^{3B}$, $R^{4B}$, $R^{SB}$, and $R^{6B}$ each represent a fluorine atom, a trifluoromethyl group, a pentafluoroethyl group, a trifluoroethyl group, an octafluorobutyl group, or a nonafluorobutyl group, and $R^{2B}$ and $R^{3B}$ are optionally bonded with each other to form a ring.

15. The patterning process according to claim 12, wherein the developer in the step (4) is an organic solvent.

16. The patterning process according to claim 15, wherein the organic solvent is one or more solvents selected from 2-octanone, 2-nonanone, 2-heptanone, 3-heptanone, 4-heptanone, 2-hexanone, 3-hexanone, diisobutyl ketone, methyl cyclohexanone, acetophenone, methylacetophenone, propyl acetate, butyl acetate, isobutyl acetate, amyl acetate, butenyl acetate, isoamyl acetate, propyl formate, butyl formate, isobutyl formate, amyl formate, isoamyl formate, methyl valerate, methyl pentenoate, methyl crotonate, ethyl crotonate, methyl lactate, ethyl lactate, propyl lactate, butyl lactate, isobuthyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

17. The patterning process according to claim 12, wherein one or more tertiary alcohol structure be contained in either or both of the metal compound shown by the formula (A-1) and the divalent or trivalent alcohol shown by the formula (A-3).

18. The patterning process according to claim 12, wherein the divalent or trivalent alcohol shown by the general formula (A-3) is any of the alcohols shown by the following formula (T):

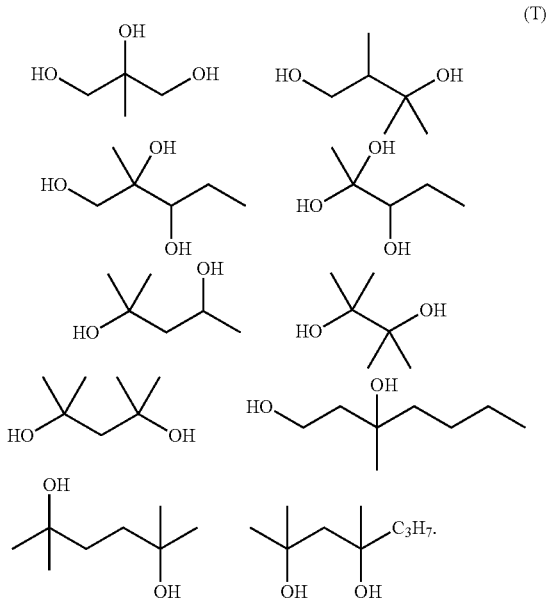

(T)

19. The patterning process according to claim 1, wherein the sensitizer is one or more elements selected from sensitizers shown by the following general formula (B-1):

(B-1)

wherein $M^{m+}$ represents an ion of a metal selected from Mg, Ca, Ce, Zn, Cu, In, Fe, Yb, Y, Tm, Sn, Ni, Sc, Hf, Nb, Ti, Zr, Ba, Ho, Tb, Lu, La, Ag, Eu, Dy, Gd, Rb, Sr, and Cs; $Y^-$ represents an alkylsulfonate ion, an arylsulfonate ion, an alkylsulfonimidate ion, or an alkylsulfonmethidate ion each having at least one fluorine atom; and "n" is an integer satisfying $1 \leq n \leq 4$.

20. The patterning process according to claim 19, wherein $Y^-$ in the general formula (B-1) is shown by any of the following general formulae (B-1-1) to (B-1-3):

 (B-1-1)

 (B-1-2)

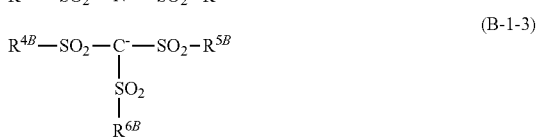 (B-1-3)

wherein $R^{1B}$ represents a linear, branched, or cyclic alkyl group, alkenyl group, or alkynyl group having 5 to 30 carbon atoms, or an aryl group or aralkyl group having 6 to 30 carbon atoms, each having at least one fluorine atom and optionally having a halogen atom, an ether group, a thiol group, an ester group, a carbonate group, a carbonyl group, an amide group, an amino group, an azide group, a carbamate group, a nitro group, a cyano group, a hydroxy group, a carboxy group, a sulfo group, a sulfonate ester group, a sultone group, a lactone ring, or a lactam ring; $R^{2B}$, $R^{3B}$, $R^{4B}$, $R^{5B}$, and $R^{6B}$ each represent a fluorine atom, a trifluoromethyl group, a pentafluoroethyl group, a trifluoroethyl group, an octafluorobutyl group, or a nonafluorobutyl group, and $R^{2B}$ and $R^{3B}$ are optionally bonded with each other to form a ring.

21. The patterning process according to claim 1, wherein the developer in the step (4) is an organic solvent.

22. The patterning process according to claim 21, wherein the organic solvent is one or more solvents selected from 2-octanone, 2-nonanone, 2-heptanone, 3-heptanone, 4-heptanone, 2-hexanone, 3-hexanone, diisobutyl ketone, methyl cyclohexanone, acetophenone, methylacetophenone, propyl acetate, butyl acetate, isobutyl acetate, amyl acetate, butenyl acetate, isoamyl acetate, propyl formate, butyl formate, isobutyl formate, amyl formate, isoamyl formate, methyl valerate, methyl pentenoate, methyl crotonate, ethyl crotonate, methyl lactate, ethyl lactate, propyl lactate, butyl lactate, isobuthyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

* * * * *